United States Patent
Seki et al.

(10) Patent No.: US 7,220,827 B2
(45) Date of Patent: May 22, 2007

(54) COMPOUND BINDING TO LEUKOCYTES AND MEDICINAL COMPOSITION CONTAINING THE COMPOUND IN LABELED STATE AS THE ACTIVE INGREDIENT

(75) Inventors: Ikuya Seki, Sodegaura (JP); Takayoshi Kawaguchi, Sodegaura (JP); Yoshifumi Shirakami, Sodegaura (JP)

(73) Assignee: Nihon Medi-Physics Co., Ltd., Hyogo-ken (JP)

( * ) Notice: Subject to any disclaimer, the term of this patent is extended or adjusted under 35 U.S.C. 154(b) by 0 days.

(21) Appl. No.: 10/528,771

(22) PCT Filed: Sep. 26, 2003

(86) PCT No.: PCT/JP03/12362

§ 371 (c)(1),
(2), (4) Date: Mar. 23, 2005

(87) PCT Pub. No.: WO2004/029080

PCT Pub. Date: Apr. 8, 2004

(65) Prior Publication Data

US 2006/0057064 A1 Mar. 16, 2006

(30) Foreign Application Priority Data

Sep. 27, 2002 (JP) .............................. 2002-282229

(51) Int. Cl.
*A61K 38/04* (2006.01)

(52) U.S. Cl. ................. 530/328; 530/327; 530/329; 530/330; 514/14; 514/15; 514/16; 514/17; 435/7.1; 427/47

(58) Field of Classification Search ............ 514/14–17; 530/327, 328, 329, 330; 435/7.1; 427/47
See application file for complete search history.

(56) References Cited

U.S. PATENT DOCUMENTS

| | | | |
|---|---|---|---|
| 6,808,877 B2 * | 10/2004 | Wang et al. | 435/5 |
| 6,830,893 B2 * | 12/2004 | Wang et al. | 435/7.1 |
| 6,955,884 B2 * | 10/2005 | Lund et al. | 435/7.1 |

FOREIGN PATENT DOCUMENTS

| | | |
|---|---|---|
| WO | WO 90/10463 A1 | 9/1990 |
| WO | WO 90/13317 A1 | 11/1990 |
| WO | WO 95/11045 A1 | 4/1995 |
| WO | WO 97/14443 A1 | 4/1997 |

OTHER PUBLICATIONS

D.S. Edwards, et al. "RP463: a stabilized technetium-99m complex of a hydrazino nicotinamide derivatized chemotactic peptide for infection imaging." *Bioconjugate Chemistry* 1999, vol. 10, No. 5, pp. 884-891.

(Continued)

*Primary Examiner*—David Lukton
(74) *Attorney, Agent, or Firm*—Sughrue Mion, PLLC

(57) ABSTRACT

A compound that comprises Met-Leu-Phe or Nle-Leu-Phe serving as the leukocyte-binding site of a formyl peptide receptor (FPR), a binding part comprising Ser or Thr that increases the binding ratio to monocytes and lymphocytes in all leukocytes, a group that can be labeled with a radioactive metal or a paramagnetic metal, and spacers binding the three moieties together shows binding properties specific to all leukocytes, i.e., neutrophils, monocytes and lymphocytes both in vivo and in vitro. Owing to this characteristic, this compound is highly useful in SPECT image diagnosis, PET image diagnosis, MRI image diagnosis and the like, for imaging sites of inflammation.

11 Claims, 21 Drawing Sheets

HPLC CHROMATOGRAM OF Tc-99m-PEPTIDE 4

OTHER PUBLICATIONS

K. Verbeke, et al. "Influence of the bifunctional chelate on the biological behavior of 99mTc-labeled chemotactic peptide conjugates." *Nuclear Medicine & Biology*, 2000, vol. 27, No. 8, pp. 769-779.

Baidoo, K.E., et al., *High-Affinity No-Carrier-Added 99mTc-Labeled Chemotactic Peptides for Studies of Inflammation in Vivo*, Bioconjugate Chem. Mar.-Apr.; 9(2): 1998 208-17.

Baidoo, K.E., et al., Bioconjug. Chem. Mar.-Apr.; 9(2): 1998 208-17.

* cited by examiner

HPLC CHROMATOGRAM OF Tc-99m-PEPTIDE 4

HPLC CHROMATOGRAM OF Tc-99m-PEPTIDE 6

2 HRS. AFTER ADMINISTRATION  22 HRS. AFTER ADMINISTRATION

IMAGE OF Tc-99m-PEPTIDE 3 IN MODEL RABBIT WITH INFECTIOUS DISEASE

2 HRS. AFTER ADMINISTRATION  22 HRS. AFTER ADMINISTRATION

IMAGE OF Tc-99m-PEPTIDE 4 IN MODEL RABBIT WITH INFECTIOUS DISEASE

IMAGE OF Tc-99m-PEPTIDE 6 IN MODEL RABBIT WITH INFECTIOUS DISEASE

IMAGE OF Tc-99m-PEPTIDE 8 IN MODEL RABBIT WITH INFECTIOUS DISEASE

2 HRS. AFTER ADMINISTRATION

5 HRS. AFTER ADMINISTRATION

IMAGE OF Tc-99m-PEPTIDE 9 IN MODEL RABBIT WITH INFECTIOUS DISEASE

2 HRS. AFTER ADMINISTRATION

22 HRS. AFTER ADMINISTRATION

IMAGE OF Tc-99m-PEPTIDE 12 IN MODEL RABBIT WITH INFECTIOUS DISEASE

IMAGE OF Tc-99m-PEPTIDE 13 IN MODEL RABBIT WITH INFECTIOUS DISEASE

IMAGE OF Tc-99m-PEPTIDE 14 IN MODEL RABBIT WITH INFECTIOUS DISEASE

IMAGE OF Tc-99m-PEPTIDE 15 IN MODEL RABBIT WITH INFECTIOUS DISEASE

IMAGE OF Tc-99m-PEPTIDE 16 IN MODEL RABBIT WITH INFECTIOUS DISEASE

IMAGE OF Tc-99m-PEPTIDE 17 IN MODEL RABBIT WITH INFECTIOUS DISEASE

IMAGE OF Tc-99m-PEPTIDE 18 IN MODEL RABBIT WITH INFECTIOUS DISEASE

TIME COURSE CHANGE OF URINARY EXCRETION OF Tc-99m-PEPTIDES IN NORMAL RATS

TIME COURSE CHANGE OF ACCUMULATION OF Tc-99m-PEPTIDES IN SMALL INTESTINE ON NORMAL RATS

DISTRIBUTION OF Tc-99m-PEPTIDE IN HUMAN BLOOD

DISTRIBUTION OF Tc-99m LABELED PEPTIDE IN BLOOD OF MODEL RAT WITH COLITIS

30 MIN. AFTER ADMINISTRATION

120 MIN. AFTER ADMINISTRATION

IMAGE OF Tc-99m LABELED PEPTIDE 3 IN MODEL RAT WITH COLITIS

30 MIN. AFTER ADMINISTRATION

120 MIN. AFTER ADMINISTRATION

IMAGE OF Tc-99m LABELED PEPTIDE 6 IN MODEL RAT WITH COLITIS

IMAGE OF Tc-99m LABELED LEUKOCYTES IN MODEL RAT WITH COLITIS (AUTORADIOGRAPHY)    (IMMUNOSTAINING OF GRANULOCYTE ANTIBODY)    (IMMUNOSTAINING OF MONOCYTE ANTIBODY)

IMAGES OF PEPTIDE 6 ON AUTORADIOGRAPHY AND IMMUNO-STAINING OF RAT WITH COLITIS (AUTORADIOGRAPHY)    (IMMUNOSTAINING OF GRANULOCYTE ANTIBODY)    (IMMUNOSTAINING OF MONOCYTE ANTIBODY)

IMAGES OF PEPTIDE 14 ON AUTORADIOGRAPHY AND IMMUNO-STAINING OF RAT WITH COLITIS (AUTORADIOGRAPHY)    (IMMUNOSTAINING OF GRANULOCYTE ANTIBODY)    (IMMUNOSTAINING OF MONOCYTE ANTIBODY)

IMAGES OF Tc-99m LABELED LEUKOCYTES ON AUTORADIOGRAPHY AND IMMUNO-STAINING OF RAT WITH COLITIS

INFLAMMATION/NORMAL TISSUE RATIO OF AUTORADIOGRAPHY OF RAT WITH COLITIS USING Tc-99m LABELED PEPTIDE AND Tc-99m LABELED LEUKOCYTES

INHIBITION RATE OF PEPTIDES FOR BINDING BETWEEN RECOMBINANT HUMAN RECEPTOR AND [3H]-FMLP

IMAGE OF Tc-99m-PEPTIDE 6 IN MODEL RABBIT WITH INFECTIOUS
DISEASE WITHOUT INHIBITOR OF FMLP

IMAGE OF Tc-99m-PEPTIDE 6 IN MODEL RABBIT WITH INFECTIOUS DISEASE WITH INHIBITION OF FMLP

```
                         SEQUENCE LISTING

<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 1

Xaa Leu Phe Xaa Tyr Lys Ser Cys Gly Asn
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 2

Xaa Leu Phe Xaa Tyr Lys Ser Cys Asp Asp
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Leukocyte Binding Peptide
```

-continued

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 3

Xaa Leu Phe Xaa Tyr Lys Ser Cys Gly Asp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 4

Xaa Leu Phe Xaa Tyr Lys Ser Arg Asp Cys Asp Asp
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (7)..(7)
<223> OTHER INFORMATION: BLOCKED
```

```
<400> SEQUENCE: 5

Xaa Leu Phe Xaa Tyr Lys Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (11)..(11)
<223> OTHER INFORMATION: BLOCKED

<400> SEQUENCE: 6

Xaa Leu Phe Lys Ser Ser Asn Arg Cys Asp Asp
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (8)..(8)
<223> OTHER INFORMATION: BLOCKED

<400> SEQUENCE: 7

Xaa Leu Phe Xaa Tyr Lys Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (7)..(7)
<223> OTHER INFORMATION: BLOCKED

<400> SEQUENCE: 8

Xaa Leu Phe Xaa Tyr Lys Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (9)..(9)
<223> OTHER INFORMATION: BLOCKED

<400> SEQUENCE: 9

Xaa Leu Phe Xaa Tyr Lys Ser Arg Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
```

```
<222> LOCATION: (9)..(9)
<223> OTHER INFORMATION: BLOCKED

<400> SEQUENCE: 10

Xaa Leu Phe Xaa Tyr Lys Ser Ser Asn
1               5

<210> SEQ ID NO 11
<211> LENGTH: 12
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 11

Xaa Leu Phe Xaa Tyr Lys Ser Arg Asp Cys Asp Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 12

Xaa Leu Phe Xaa Tyr Lys Ser Arg Asp Cys Asp Asp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Leukocyte Binding Peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 13

Xaa Leu Phe Xaa Tyr Lys Ser Arg Asp Cys Asp Asp
1               5                   10
```

COMPOUND BINDING TO LEUKOCYTES AND MEDICINAL COMPOSITION CONTAINING THE COMPOUND IN LABELED STATE AS THE ACTIVE INGREDIENT

This is a National Stage of application Ser. No. PCT/JP03/12362 filed Sep. 26, 2003 which claims priority to JP 2002-282229, filed Sep. 27, 2002.

TECHNICAL FIELD

The present invention relates to a compound binding to leukocytes and a medicinal composition containing the compound in labeled state as the active ingredient which can be used for targeting abnormal site as well as for understanding precisely a state of disease activity when a disease of an individual associated with immune reaction is to be diagnosed and/or treated. More in detail, the present invention relates to a novel compound having binding properties specific to leukocytes both in vivo and in vitro and can be labeled with a radioactive metal or a paramagnetic metal, which is useful for pathological imaging of a seat of disease including infectious diseases, inflammation, tumor and atheroscrelosis in the body of mammals. Also, the present invention relates to a medicinal composition containing said compound in labeled state as the active ingredient which is useful for radioisotope diagnosis, SPECT image diagnosis, PET image diagnosis, MRI image diagnosis or radiotherapy.

PRIOR ART

Animals including human are always influenced by the factors that may affect on the life supporting systems of an individual from the surrounding environment. These include, for example, factors with positive effects such as air, sunlight and foods, and factors with negative effects such as invasion of microorganisms, hazardous chemical substances, heat and radiation. Against the factors with such negative effects, the individuals brings various protecting systems into action to keep their lives.

This self-protecting system is defined biologically as immunity, and a biological reaction in relation to the immunity is referred to as immune reaction. As the factors bringing on such reactions, for example, microorganisms such as bacteria and mycoplasma, viruses, heterografts of tissue or organ, hazardous chemical compounds, heat of high temperature, excessive cooling, nuclear radiation with high energy, and electric or physical injury of tissue are known. The immune reaction including inflammation reaction is a biological reaction in response to the recognition of "self" or "not self" for the individual, which is an action of the protection system in a broad sense such as fever, leukocytes activation and migration, elimination of all of the factors except "self". Inflammation reaction is a phenomenon appeared as a part of results of the immune reactions such as removal of extraneous substances infiltrated into an individual, demolition of invaded tissue and restoration of injured tissue.

Leukocytes are included as one of important factors in the immune reactions. Tissues produce various mediators which specify the species of infiltrating leukocytes and control its level and duration, and also have, on the surface of cell membrane, various receptors which may respond by binding to mediators and other molecules existing in the body fluid including blood. The receptor activates leukocytes by binding to the corresponding mediator, and different types of receptors are expressed specifically depending on the species of leukocyte. Therefore, the species of leukocytes which infiltrate into the tissue is governed by the existing mediator.

Generally, in a local immune response such as inflammation, after getting something stimulus of tissue demolition, proteins relating to immunity such as complements take place to remove the stimulus for several hours. After that, mediators like the decomposed complements and/or cytokines are released from the demolished tissue into body fluid such as blood, and granulocytes mainly composed of neutrophils are activated thereby through the receptor, so that the leukocyte infiltration into the tissue takes place according to a density gradient of the mediator. In such case, the mediator is generally referred to as a chemotactic factor. Normally, infiltration of tissue by granulocytes reaches to a peak at over ten hours after initial stimulus. Also, infiltration by macrophages mainly composed of monocytes increases gradually to remove the cause substance of the stimulus in collaboration with granulocytes. Cytokine and the like are released from activated granulocytes and macrophages as well as from injured tissue, and thereby, infiltration of tissue by lymphocytes consisted of T-cells and B-cells which can efficiently perform immune reactions such as production of antibody, or repairing the demolished tissue, or regulating the reaction for immune response, is enhanced. Infiltration by lymphocytes reaches to a peak in dozens of hours after the initial stimulus.

The immune reaction is a quite important action for maintaining the biosis of an individual. However, since the regulation of the reaction in an individual is imperfect with respect to the purpose of maintaining its biosis, the reaction may sometime cause crucial negative effects. Typical phenomena of such negative effects are development of disorders referred to as autoimmune diseases. As a group of this kind of disorders, for example, atopic dermatitis, rheumatoid arthritis, Behcet's syndrome, systemic lupus erythematosus, ulcerative colitis, Crohn's disease, chronic thyroiditis and other collagen diseases are known. In the case of inflammations caused, for example, by invasion of extraneous substance such as infection, or by tissue demolition such as burn injury, the causes of the inflammation may be identified. However, in the case of autoimmune diseases, there is no specific cause factor, or the factor has not been identified. Thus, the autoimmune disease is an intractable disease with unknown cause. However, it is well known that the phenomenon commonly observed in this group of disorders is disease-specific infiltration of the tissue by leukocytes, in particular, by lymphocytes, monocytes and macrophages.

Thus, in autoimmune diseases and chronic state of inflammation and infection, lymphocytes and monocytes play universally a central role in the immune reaction through leukocyte infiltration. Therefore, search or detection of leukocyte infiltration by lymphocytes, monocytes and neutrophils, and determination of their precise levels are quite important to perform an effective medical treatment, which may keep patients away from inappropriate medication and relieve mental distress and expense for the treatment, and may contribute to reduce the cost of health insurance.

Thus, since the diagnostic imaging is a useful tool for searching and detecting leukocyte infiltration and determination its precise level, various radioactive agents and its application have been investigated in the field of nuclear medicine.

Gallium-67 ($^{67}$Ga) citrate has long been used as an agent for scintigraphy of inflammation (see, for example, Ebright, Jr. et al., Arch. Int. Med., 142, 246–254 (1982)). However, this agent has no specificity for infection site or inflammation site in addition, the radiation energy of gamma ray from $^{67}$Ga is insufficient and not suitable for obtaining a good photographic image by a common gamma camera. Further, it requires waiting time for about 72 hours from injection of the agent to complete imaging.

In the next place, as a method for imaging the infection site by nuclear medicine, leukocyte labeled with Indium-111 (hereinafter designated as $^{111}$In-leukocyte) was used (see, for example, Peters, A M. et al., J. Nucl. Med., 33, 65–67 (1992)). Thakur et al. have reported on in vitro labeling of neutrophils with radioactive nuclides, and analyzed widely and discussed on its utility (Thakur et al., Sem. Nucl. Med., 14, 10–17 (1984)). In this method, neutrophils of an individual were labeled in vitro with Indium-111 (hereinafter designated as In-111), and the labeled neutrophils were used for in vitro kinetic studies. Also, the labeled neutrophils were able to be used for imaging inflammatory focus in an acute phase of an individual.

However, when $^{111}$In-leukocyte is utilized, preparation of a radioactive labeled compound requires steps of aseptic withdrawal of autologous blood, aseptic isolation of leukocytes from the blood, aseptic labeling of leukocytes, and back injection of leukocytes labeled with radioactive nuclide to the patient, and takes a considerable time for more than 2 hours. Also, it is considered that 12 to 48 hours of waiting period from back injection of the labeled leukocytes is required to obtain an optimal pictorial image. Further, radioactivity of 200 μCi per $1 \times 10^7$ cells of leukocytes which is normally used for imaging studies is hazardous for leukocytes when In-111 is employed because of its high radioactive energy. Under the above condition, granulocytes mainly composed of neutrophils in leukocytes survive the labeling, but lymphocytes and the like die out immediately after labeling (Chianelli, M. et al., Nucl. Med. Comm., 18, 437–455 (1997)). Therefore, it is difficult to monitor dynamic states of lymphocytes and monocytes using In-111 labeled leukocytes. Furthermore, from the viewpoint of the safe radiation dosage, an administration quantity of radioactivity is limited, in many cases resulting in deterioration of pictorial image quality.

Leukocytes labeled with technetium-99m (Tc-99m) developed in the next place are able to cut down the waiting time for imaging which had been a problem with $^{111}$In-leukocytes, and able to monitor dynamic states of lymphocytes and monocytes, and further able to administer a considerably larger quantity of radioactivity compared to In-111 (see, for example, Vorne, M. et al., J. Nucl. Med., 30, 1332–1336 (1989)). However, since the labeling stability of Tc-99m is not good enough, accumulation in a non-target metabolic organ becomes a problem accordingly. In the problems of long preparation time and handling of blood sample, this method is similar to those of $^{111}$In-leukocytes (Chianelli, M. et al., Nucl. Med. Comm., 18, 437–455 (1997)).

Trial of developing labeled monoclonal and polyclonal antibodies with radioactive nuclides having binding property to human leukocytes including monocytes, neutrophils, granulocytes and the like have been carried out. For example, $^{99m}$Tc-labeled anti-granulocyte monoclonal antibody (refer for example, Lind, P. et al., J. Nucl. Med., 31, 417–473 (1990)) and $^{111}$In-labeled non-specific human immunoglobulin ($^{111}$In-HIG, see, for example, LaMuraglia, G M. et al., J. Vasc. Surg., 10, 20–28 (1989)) have been studied for detection of inflammation site caused by infection. However, $^{111}$In-HIG has similar drawback with respect to the waiting period of 24 to 48 hours from administration for obtaining optimal pictorial image.

In addition, $^{111}$In-HIG has been considered to accumulate in the inflammation site and enables to depict the site (see, for example, Rubin, R. et al., J. Nucl. Med., 29, 651–656 (1988)), however in this regard, there are two hypothesis on the mechanism of accumulation. One idea is that accumulation of $^{111}$In-HIG in the inflammation site proceeds by binding to Fc-receptor on the surface of leukocytes which infiltrate into the inflammation site (Fischman, A. et al., J. Nucl. Med., 31, 1199–1205 (1990)), and the other is that, besides the leukocyte infiltration, local diapedesis of $^{111}$In-HIG from blood vessel occurred by enhanced permeability through blood vessel, which is observed similarly for proteins like albumin (Morrel, E. et al., J. Nucl. Med., 30, 1538–1545 (1989)).

Until now, studies on the biomolecules having binding property to leukocytes using other proteins have been reported.

Van der Laken, C J. et al. have reported on labeled interleukin 1 of inflammatory cytokine with radioactive iodine (van der Laken, C J. et al., European J. Nucl. Med., 22, 1249–1255 (1995)).

Signore et al. have reported on the chronic inflammatory disease using labeled interleukin 2 of inflammatory cytokine with radioactive iodine (Signore, A. et al., Nucl. Med. Comm., 13, 713–722 (1992)).

Hay, R V. et al. have reported on the chemically induced inflammation using labeled interleukin 8 of inflammatory cytokine with radioactive iodine (Hay, R V. et al., Nucl. Med. Comm., 18, 367–378 (1997)).

These radiolabeled compounds have successfully depicted images of acute inflammation such as infection, or chronic inflammation such as autoimmune diseases.

However, from the viewpoint that these proteins including antibodies have large molecular weights, the diapedesis of these proteins with blood components may cause problems in acute inflammation which with enhanced vascular permeability (Roitt, I. et al., Essential Immunology, $8^{th}$ edn. Oxford, Blackwell Scientific (1994)). Molecules with a molecular weight of around 2000 do not remain at the same site of diapedesis for long time even if these are leaked out, but proteins like albumin (molecular weight: about 64000) tend to remain at the same site compared to compounds with low molecular weights because of their large molecular sizes. Threfore, it is difficult to judge whether the accumulation is inflammation specific or not (Morrel, E. et al., J. Nucl. Med., 30, 1538–1545 (1989)).

Small and easily synthesizable molecules are preferable to be used routinely as a radioactive medicinal agent. Peptides labeled with radioactive nuclides are considered suitable as a synthetic compound with low molecular weight, which can bind selectively to leukocytes in the whole blood and can be injected directly into patients, enabling to image the seat of disease of infection and inflammation by determining the site of leukocytes accumulation.

For example, Moyer et al. have reported on the cumulative characteristics of Tc-99m-labeled peptide compounds derived from a carboxyl terminal sequence of platelet factor 4 (PF-4) having binding property to multi-sulfated glycans such as heparin (Moyer, B R. et al., J. Nucl. Med., 37, 673–679 (1996)). This compound (PF-4 peptide-heparin) is a complex of peptide with 23 amino acid residues containing Tc-99m chelated amino acid sequence (molecular weight: about 2600) and heparin (molecular weight: about 7000 to 25000), constructing a single molecule with molecular weight of about 10000 to 30000.

Heparin bound PF-4 peptide cannot be an agent indicative of only accumulation to the site of leukocyte infiltration because of its large molecular weight like proteins. Therefore, an agent consisting of a compound with low molecular weight showing little non-specific accumulation by enhanced capillary permeability which indicates true infiltrated leukocytes has been needed. In addition, use of heparin has sometime to be limited because of its physiological activity.

Dahlman, T. et al. and Ringe, J D. et al. have reported on the risk of side effects of heparin that administration of heparin may induce reduction of bone density and long-term administration may cause osteoporosis (Dahlman, T. et al., Br. J. Obsted Gynaecol., Mar, 97, 3, 221–228 (1990); Ringe, J D. et al., Geburtshilfe Frauenheilkd., 52, 7, 426–429 (1992)). In addition to this, there may be a risk of side effects brought by physiological function of heparin including, for example, antithrombin activity, inhibition of thromboplastin production, and inhibition of platelet aggregation, or careful treatment is required when the patient has hemorrhagic disease or a potential to become hemorrhagic or severe liver disease and kidney disease. As stated above, heparin has many cautious points for its use.

As to other peptides labeled with radioactive nuclides, formyl-methionyl-leucyl-phenylalanyl (fMLF)-containing peptides have been reported in the prior art.

Day et al. have reported on the $^{125}$I labeling of chemotactic formylated peptide (fMLF) (Day, A R. et al., FEBS Lett., 77, 291–294 (1977)).

Jiang et al. have reported on in vivo accumulation of $^{125}$I-labeled chemotactic formylated peptide (fMLF) in inflammation site (see, for example, Jiang, M S. et al., Nuklearmedizin, 21, 110–113 (1982)).

Fisherman et al. have disclosed $^{111}$In labeling of chemotactic formylated peptide (fMLF) linked through DTPA (see JP 2931097).

Verbeke et al. have reported on Tc-99m labeling of chemotactic formylated peptide (fMLF) linked through mercaptoacetyl-glycyl-glycine (see, for example, Verbeke, K. et al., Nuclear Medicine & Biology, 27, 769–779 (2000)).

Baidoo et al. have reported on Tc-99m labeling of chemotactic formylated peptide (fMLF) linked through diaminodithiol compound (refer, Baidoo, K. E. et al., Bioconjugate Chemistry, 9, 208–217 (1998)).

Additionally, there are reports on use of the chemotactic formylated peptides (fMLF) labeled with radioactive nuclides for in vitro labeling of leukocytes with radioactive nuclides through photo-affinity thereof (see, for example, U.S. Pat. No. 4,986,979).

Also, there are reports on chemotactic formylated peptides (fMLF) capable of being labeled with radioactive nuclides (see, for example, U.S. Pat. No. 5,792,444).

Chemotactic formylated peptide (fMLF) is considered to bind to leukocytes through formylated peptide receptor (hereinafter designated as receptor FPR) (Niedel, J. E. et al., Science, 205, 4413, 1412–1414 (1979)), and the leukocytes expressing receptor FPR are neutrophils and monocytes (Lewis, S L. et al., Inflammation, 4, 363–375 (1983)).

Normal composition of leukocytes present in human blood is composed of about 50% of neutrophils and 10% of monocytes. It has been reported that most of leukocytes bound with some analogues of known chemotactic formylated peptides are neutrophils because the population of monocytes in blood is only one fifth or less of neutrophils, and the binding of the peptides to lymphocytes and monocytes is not strong (Verbeke, K. et al., Nucl. Med. Biol., 27, 769–779 (2000)).

Also, accumulation of formylated peptide labeled with a radioactive nuclide is observed in acute inflammation such as infectious diseases of bacteria with neutrophils infiltration (see, Babich, J W. et al., J. Nucl. Med., 34, 2176–2181 (1993)), but there is no report on the accumulation of said peptide to the disease diagnosed as chronic inflammation.

Further, in clinical diagnosis, diseases having a need of image diagnosis including nuclear medicine testing or MRI (magnetic resonance imaging) testing are mostly used in diseases having difficulty in identifying a lesion by primary diagnosis such as in vitro testing or the cases of diseases in chronic state. In such case, medical treatments for inhibiting immune reaction and leukocyte infiltration by administration of steroid drug and leukocytes reducing treatment have frequently been applied. Therefore, an agent with low molecular weight which is unsusceptible to enhanced vascular permeability and which enables to visualize immune reaction and leukocyte infiltration to perform image diagnosis of the diseases accompanied by an inflammation of immune reaction including chronic inflammation has been needed.

The method for labeling peptides and polypeptides with Tc-99m is well known art (see, for example, JP-A-8-231587).

SUMMARY OF THE INVENTION

In consideration of the circumstances of prior art, an object of the present invention is to provide a compound having binding properties specific to leukocytes, i.e., neutrophils, monocytes and lymphocytes both in vivo and in vitro and capable to be labeled with a radioactive metal or a paramagnetic metal, and a medicinal composition containing said compound in labeled state as the active ingredient which is useful for SPECT image diagnosis, PET image diagnosis, MRI image diagnosis, radioactive treatment and so on, wherein imaging is performed in a site with vigorous leukocyte infiltration accompanied by an immune reaction in an individual.

Namely, the present invention relates to a compound binding to loeucocytes represented by the following formula (1):

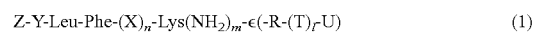

$$Z\text{-}Y\text{-}Leu\text{-}Phe\text{-}(X)_n\text{-}Lys(NH_2)_m\text{-}\epsilon(\text{-}R\text{-}(T)_l\text{-}U) \qquad (1)$$

wherein, in the formula (1), Z represents a protecting group for an amino group; Y represents Met or Nle; in $(X)_n$, X represents a spacer consisting of one or more of amino acids and/or synthetic organic compounds, and n represents 1 or 0; in $(NH_2)_m$, $NH_2$ represents an amide group as a protecting group for a carboxyl group in the α position of Lys, and m represents 1 or 0; in $\epsilon(\text{-}R\text{-}(T)_l\text{-}U)$, R represents Ser or Thr binding to an ε-amino group of Lys through an amide bond, T represents a spacer consisting of one or more of amino acids and/or synthetic organic compounds, l represents 1 or 0, and U represents a group which can be labeled with a metal; with the proviso that said X and T may be the same or different from each other).

Furthermore, the present invention relates to a medicinal composition containing the compound binding to leukocytes represented by the above formula (1) in labeled state with a radioactive metal or a paramagnetic metal as the active ingredient.

BEST MODE FOR CARRYING OUT OF THE INVENTION

Figure 1:
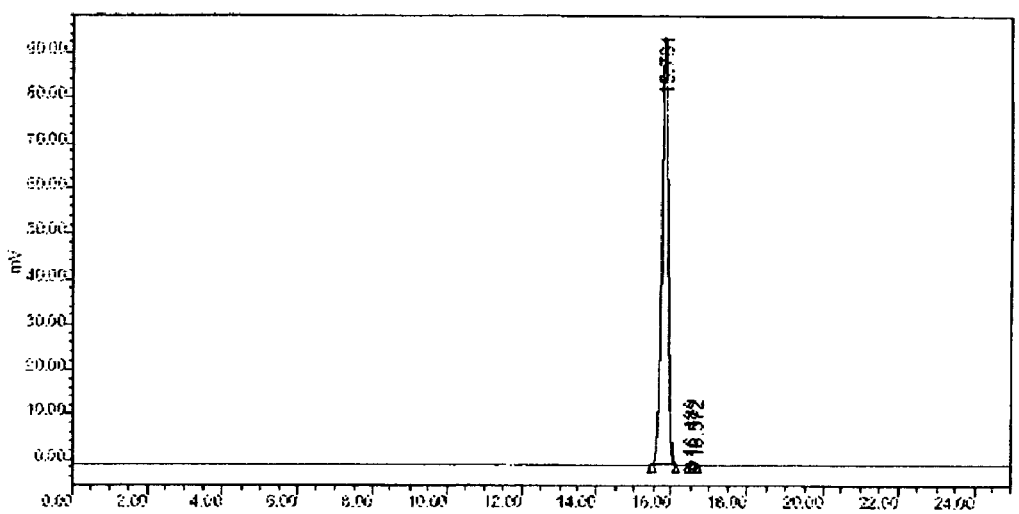
FIG. 1 shows a HPLC chromatogram of Tc-99m-peptide 4.

Hereinbelow, mode for carrying out of the present invention will be described. All amino acids used in the present specification are denoted by single or three characters expression, and unless otherwise noted, the left hand shows the N-terminal side and the right hand shows the C-terminal side. Inside of the parentheses following an amino acid expresses, unless otherwise noted, a peptide or an organic compound bound to the side chain. Also, an amino acid sequence in the parenthesis is expressed in such a manner as the right hand for the N-terminal side and the left hand for the C-terminal side to make easy for understanding the whole structure. Further, in the present specification, an amino acid with D-configuration is designated as D-amino acid.

A compound binding to leukocytes of the present invention is represented by the following formula (1):

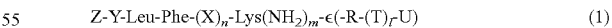

Z-Y-Leu-Phe-(X)$_n$-Lys(NH$_2$)$_m$-ε(-R-(T)$_l$-U)     (1)

Namely, said formula (1) comprises a binding site Z-Y-Leu-Phe- to the receptor FPR of leukocytes; a binding part -R- consisting of Ser or Thr which elevates the binding ratio to monocytes and lymphocytes of the whole leukocytes; a structure -U- which can be labeled with a radioactive metal or a paramagnetic metal; and spacers -(X)$_n$-, -Lys(NH$_2$)$_m$- and -(T)$_l$- which bind these groups together.

More specifically, the following compounds binding to leukocytes are exemplified as preferred embodiments.

formyl-Nle-Leu-Phe-Nle-Tyr-Lys(NH$_2$)-ε-(-Ser-Cys-Gly-Asn);

formyl-Nle-Leu-Phe-Nle-Tyr-Lys(NH$_2$)-ε-(-Ser-Cys-Asp-Asp);

formyl-Nle-Leu-Phe-Nle-Tyr-Lys(NH$_2$)-ε-(-Ser-Cys-Gly-Asp);

formyl-Nle-Leu-Phe-Nle-Tyr-Lys(NH$_2$)-ε-(-Ser-D-Arg-Asp-Cys-Asp-Asp);

formyl-Nle-Leu-Phe-Nle-Tyr-Lys(NH$_2$)-ε-(-Ser-1,4,8,11-tetraazacyclotetradecane-1,4,8,11-tetraacetic acid);

formyl-Nle-Leu-Phe-Lys(NH$_2$)-ε-(-Ser-D-Ser-Asn-D-Arg-Cys-Asp-Asp);

formyl-Nle-Leu-Phe-Nle-Tyr-Lys(NH$_2$)-ε-(-Ser-D-Arg-diethylenetriamine pentaacetic acid);

formyl-Nle-Leu-Phe-Nle-Tyr-Lys(NH$_2$)-ε-(-Ser-1,4,8,11-teraazacyclotetradecane-butyric acid);

formyl-Nle-Leu-Phe-Nle-Tyr-Lys(NH$_2$)-ε-(-Ser-D-Arg-Asp-1,4,8,11-tetraazacyclotetradecane-butyric acid);

formyl-Nle-Leu-Phe-Nle-Tyr-Lys(NH$_2$)-ε-(-Ser-D-Ser-Asn-1,4,8,11-tetraazacyclotetradecane-butyric acid);

acetyl-Nle-Leu-Phe-Nle-Tyr-Lys(NH$_2$)-ε-(-Ser-D-Arg-Asp-Cys-Asp-Asp);

carbamyl-Nle-Leu-Phe-Nle-Tyr-Lys(NH$_2$)-ε-(-Ser-D-Arg-Asp-Cys-Asp-Asp); and methyl-Nle-Leu-Phe-Nle-Tyr-Lys(NH$_2$)-ε-(-Ser-D-Arg-Asp-Cys-Asp-Asp).

With regard to the compound binding to leukocytes represented by the formula (1), in the binding site to the receptor FPR Z-Y-Leu-Phe-, Z is a protecting group for an amino acid including, for example, acyl group with 1 to 9 carbon atoms such as formyl and acetyl groups, an acyloxy group with 2 to 9 carbon atoms such as t-Boc group, a lower alkyl group with 1 to 6 carbon atoms such as methyl, ethyl and propyl groups, and carbamyl group. When N-terminal of Met or Nle in Y is a formyl group, it shows binding property to the receptor FPR of leukocytes recognizing the formylated peptide, and an acetyl group and a t-Boc group also show binding property to the receptor as well.

In Z-Y-Leu-Phe- of the above formula (1), Y represents Met or Nle as an amino acid. The receptor FPR, which is one of receptors regularly expressed on the cell membrane of neutrophils and monocytes in leukocytes, has a strong binding property to a formylated peptide, and hence shows a binding property to Met. The receptor also shows a binding property to Nle as well which has a similar steric structure to that of Met.

Leu and Phe have a high binding property to neutrophils and monocytes. The receptor FPR which has a strong binding property to formylated peptide also has a binding property to peptides such as formyl-Met, formyl-Met-Met, formyl-Met-Met-Leu and formyl-Met-Leu-Leu, and most strongly to formyl-Met-Leu-Phe.

The most prominent feature of the present invention is R which is bound to Z-Y-Leu-Phe- in the above formula (1) through the spacer X and an ε-amino group of -Lys(NH$_2$)$_m$-.

R is selected from Ser and Thr which are amino acids having a hydroxyl group in the side chain. By utilizing this structure having Ser or Thr which can be labeled with a metal, remarkable binding property to lymphocytes and monocytes has been realized, which has not been seen with the conventional leukocytes-binding compounds with low molecular weight. The conventional peptides consisting of only Z-Y-Leu-Phe-, which is a binding site to the receptor FPR, showed a binding property to neutrophils and monocytes, but hardly showed a binding property to lymphocytes. By combining Z-Y-Leu-Phe- of the binding site to the receptor FPR and a structure which can be labeled with a metal through Ser or Thr bound to ε-amino group of Lys, binding ratio of the peptide to monocytes and lymphocytes was improved significantly. In consequence, it has been realized that the compound binding to leukocytes of the present invention represented by the formula (1) has an ability to bind to all species of leukocytes, namely neutrophils, monocytes and lymphocytes. For example, in the case of the conventional hemocyte-binding compounds, a ratio of the compound bound to lymphocytes and monocytes to the compound bound to the whole leukocytes is in the range of about 12% to 35%, whereas, in the case of the hemocyte-binding compound of the present invention, a ratio of the compound bound to lymphocytes and monocytes to the compound bound to the whole leukocytes is elevated up to the range of about 18% to 65%. This indicates that a lesion with vigorous infiltration by leukocytes can be targeted, and that the compound of the present invention is a useful agent for diagnosis or medical treatment of the diseases accompanied by leukocyte infiltration.

In the compound binding to leukocytes of the present invention, each distance between the binding site to the receptor FPR Z-Y-Leu-Phe-, in particular, Ser or Thr of the binding site R to the receptor of lymphocytes and monocytes, and the structure U to be labeled with a radioactive metal or a paramagnetic metal may be adjusted adequately by linking these parts through a spacer X, and ε-amino group of -Lys(NH$_2$)$_m$- and a spacer T. Owing to this, these parts can be linked each other while the binding property to the receptor which is significantly influenced by the steric structure is maintained. Namely, in order to bind the C-terminal of Ser or Thr of R with the C-terminal of Z-Y-Leu-Phe-, it is preferable to add Lys having a side chain with 4 carbon atoms and an amino group to the C-terminal group of Z-Y-Leu-Phe- and then Ser or Thr is linked to the ε-amino group of Lys. When further spatial distance is needed, the spacer X may be added.

Each of X and T is a spacer consisting of one or more of amino acids and/or synthetic organic compounds, which may be a component of the compound binding to leukocytes of the present invention when needed. X and Y may be the same or different from each other. However, Cys residue is not an appropriate amino acid to use as a component of X or T, because the sulfanyl group may form an intramolecular or an intermolecular disulfide bond resulting in polymeric form such as dimer, and this structural change may influence significantly on binding property to the receptor. Also, Pro is not preferable for binding to the receptor, because if Pro is contained in X or T, the steric structure is restricted and degree of spatial freedom is limited accordingly. Therefore, it is desirable that Cys and Pro are excluded from the amino acids contained constructing the sequence of X or T.

More specifically, an amino-acid to be used for X which has little influence on the binding property to the receptor includes, for example, uncharged amino acids such as Gly, Ala, Val, Leu and Ile, Nle, Tyr, and Nle-Tyr. As to an amino acid for T, for the purpose to provide a distance from the binding site to the receptor to the structure to be labeled with a radioactive metal or a paramagnetic metal, or to control in vivo dynamic state in the living body, or to provide resistance against metabolism in the living body, the same amino acids as described above, non-amino acid compounds or the combination thereof may be used. Also, L- and D-form amino acids other than the above amino acids, hydrophobic amino acids such as Gly, and polar and charged amino acids (acidic or basic) such as Arg, Asp, Glu and Lys may be used.

The synthetic organic compound constructing the spacer includes, for example, compounds such as 1,5-hexadiene, trans-2-methyl-1,3-pentadiene and 4-methyl-3-nitroacetophenone, each having a hydrophobic functional group such as methyl group, ethyl-group and benzyl group; compounds such as (±)-2-methyl-2,4-pentanediol(hexylene glycol) and 3-methyl-1,3,5-pentanetriol having a polar functional group such as hydroxyl group and amid group; compounds such as methylenesuccinic acid, 4-maleinimide butyric acid and 6-maleinimide caproic acid having a charged functional group such as carboxyl group, amino group and imino group.

With regard to the group U which can be labeled with a metal, a group consisting of one or more of amino acids or a group consisting of non-amino acid compounds may be used. As the group consisting of one or more of amino acids, the peptide represented by -Cys-A1-A2 may be used (with the proviso that A1 and A2 are amino acids except for Cys and Pro). These peptides include, for example, -Cys-Gly-Asp, -Cys-Asp-Asp, -Cys-Asp-Gly, -Cys-Gly-Glu, -Cys-Glu-Glu, -Cys-Glu-Gly, -Cys-Gly-Asn, -Cys-Asn-Asn, -Cys-Asn-Gly, -Cys-Gly-Gln, -Cys-Gln-Gln, -Cys-Gln-Gly, -Cys-Gly-Lys, -Cys-Lys-Lys, -Cys-Lys-Gly, -Cys-Gly-Arg, -Cys-Arg-Arg and -Cys-Arg-Gly.

The group consisting of non-amino acid compound which can be labeled with a metal includes, for example, a nitrogen-containing cyclic compound with 8 to 20 carbon atoms such as 1,4,7,10-tetraazacyclododecane(Cyclen), 1,4,8,11-tetraazacyclotetradecane(Cyclam), 1,4,8,12-tetraazacyclopentadecane and 1,4,8,11-tetraazacyclotetradecane-5,7-dione(Dioxocycam); a nitrogen-containing cyclic carboxylic acid compound with 8 to 20 carbon atoms such as 1,4,8,11-tetraazacyclotetradecane-1,4,8,11-tetraacetic acid (TETA), 1,4,7,10-tetraazacyclododecane-N,N',N'',N'''-tetraacetic acid (DOTA), 1,4,8,11-tetraazacyclotetradecane-5,7-dione-N,N',N'',N'''-tetraacetic acid, 1,4,7,10-tetraazacyclododecane-butyric acid and 1,4,8,10-tetraazacyclododecane-butyric acid; a derivative of nitrogen-containing cyclic carboxylic acid with 8 to 20 carbon atoms such as 1,4,7,10-tetraazacyclododecane-1-aminoethyl carbamoylmethyl-4,7,10-tris[R,S]-methylacetic acid (DO3MA) and 1,4,7,10-tetraazacyclododecane-1,4,7,10-$\alpha,\alpha',\alpha'',\alpha'''$-tetramethylacetic acid (DOTMA); and an alkyleneamine carboxylic acid with 4 to 10 carbon atoms such as ethylenediamine tetraacetic acid (EDTA), diethylenetriamine pentaacetic acid (DTPA), triethylenetetraamine hexaacetic acid and ethyleneglycol-(2-aminoethyl)-N,N,N',N'-tetraacetic acid (EGTA).

When the compound binding to leukocytes of the present invention is used as a medicinal composition for image diagnoses, depending on the purpose of diagnosis or the lesion to be treated, imaging of the region to be diagnosed may be carried out in short time by virtues of reduction of unnecessary radiation to the living body and alleviation of the back-ground effect on image diagnosis by smooth excretion of unnecessary metabolites by controlling dynamic state in vivo. For example, with regard to the amino acids and the like to be used for constructing the spacers X and T, their metabolic transfer can be controlled toward the gastrointestinal tract by using aliphatic amino acids such as Gly, Ala, Ile, Leu and Val, aromatic amino acids such as Phe, Trp and Tyr, sulfur-containing amino acids such as Met, or compounds containing a hydrophobic functional group such as methyl, ethyl and benzyl group. In order to control their metabolic transfer toward the urine and the kidney, charged amino acids or compounds having a charged functional group may be used by selecting hydroxyl amino acids such as Ser and Thr, acidic amino acid amides such as Asn and Gln, charged (acidic and basic) amino acids such as Arg, Asp, Glu and Lys, or synthetic organic compounds containing a polar functional group such as hydroxyl group and amide group, compounds containing a charged functional group such as carboxyl group, amino group and imino group. In addition, when a distance between the binding site to the receptor and the structure to be labeled with a metal is needed, one or more of amino acids or synthetic organic compounds having a straight chain such as alkyl group may be used.

With regard to an amino acid contained in the group U which can be labeled with a metal, the same description as above can be addressed. For example, when Asp or Lys is selected, or a compound containing carboxyl group or amino group is selected, the major excretion rout of the final metabolites after administration of the labeled compound with a radioactive metal may be controlled toward the kidney. Also, when a hydrophobic amino acid such as Gly is selected, the major excretion rout of the final metabolites may be controlled toward the gastrointestinal tract.

Further, with regard to an amino acid and the like to be used as a component of the spacers X and T, in order to provide a resistance against the metabolism in vivo, D-amino acids or artificial amino acids and non-amino acids may be used. More specifically, the spacer consisting of D-amino acid includes, for example, amino acid sequences such as D-Arg-Asp, Arg-D-Asp, D-Arg-D-Asp, D-Asp-Arg, Asp-D-Arg, D-Asp-D-Arg, Ser-D-Arg, D-Ser-Arg, D-Ser-D-Arg, D-Arg-Ser, Arg-D-Ser, D-Arg-D-Ser, Ser-D-Asp, D-Ser-Asp, D-Ser-D-Asp, D-Asp-Ser, Asp-D-Ser and D-Asp-D-Ser.

The compound binding to leukocytes of the present invention can be synthesized according to the methods described below.

(1) When said compound is consisted of amino acids only, the compound can be synthesized according to the methods such as Boc-method and Fmoc-method using commonly used automatic peptide synthesizers such as the automatic peptide synthesizer made by Applied Biosystems (USA). A synthesized complex may be purified by simultaneously performing deprotection and cutting off from the bound state to the solid phase carrier resin, followed by a high performance liquid chromatography (hereinafter designated as HPLC) using a reversed phase column. Otherwise, the said compound may be obtained by a liquid phase peptide synthesis, or from animal sources and the like.

(2) When said compound contains a non-amino acid, the compound can be synthesized in most cases by the same method as described above. For example, said compound can be synthesized as follows. Namely, Lys residue or a protection derivative thereof is bound to the solid phase of carrier resin, and a N-terminal thereof is successively bound with an amino acid residue or a protection derivative thereof of X, or a compound serving as a spacer or a protection derivative thereof, Phe or a protection derivative thereof, Leu or a protection derivative thereof and an amino acid or a protection derivative thereof of Y. Then, an $\epsilon$-amino group on a side chain of Lys bound to the solid phase of carrier resin is activated, and Ser or Thr or a protection derivative thereof of R is bound thereto, followed by further binding with an amino acid or a protection derivative thereof of spacer T, or a compound serving as a spacer or a protection derivative thereof and a compound U which can be a group to be labeled with a metal or a protection derivative thereof, then cutting off the synthetic compound of the above formula (1) from the carrier resin.

The medicinal composition containing a compound in the labeled state as the active ingredient obtained by labeling a compound binding to leukocytes of the present invention with a radioactive metal or a paramagnetic metal, may be used, for example, as an agent for radioisotope diagnosis or a radioactive therapeutic agent, in particular, for image diagnosis and treatment of a site of lesion with vigorous leukocyte infiltration accompanied by an immune reaction in an individual. Namely, in a disease having active lesion with vigorous infiltration by neutrophils, monocytes or lymphocytes, or more than 2 species of leukocyte cells, detection of the site and measurement of a level of leukocyte accumulation may be performed using a specific detector.

Diseases accompanied by an immune reaction in an individual include a group of disorders consisting of infection, inflammation and aterosclerosis in the mammalian body. Namely, said group of disorders include viral infection, bacterial infection, fungal infection, protozoan disease, nematode disease, collagen disease and autoimmune diseases other than collagen disease. In Japan, about 80% of hepatitis patients are viral hepatitis caused by viral infection, and others are mostly autoimmune hepatitis, and therefore, a large number of inflammatory diseases of liver are the disease having infiltration by lymphocytes and monocytes compared with that by nutrophils. In the case of disease having relatively low level of neutrophil infiltration like this, it is pointed out that, if the conventional analogues of fMLF are applied, leukocyte infiltration of the lesion may be underestimated because the binding to lymphocytes and monocytes is weaker compared with that to neutrophils. However, the compound binding to leukocytes of the present invention enables to correctly identify the leukocyte infiltration of the disease with little neutrophil infiltration such as most autoimmune diseases and leishmaniasis, because said compound has a high binding property not only to neutrophils but also to lymphocytes and monocytes.

A group of disorders showing a quantity of infiltration by lymphocytes and monocytes compared with neutrophils, or a group showing a large population of lymphocytes and monocytes in the infiltrated leukocytes includes viral infection, protozoan disease, nematode disease, collagen disease and autoimmune diseases other than collagen disease. The present invention is considered effective to the group of disorder accompanied by immune reaction such as leukocyte infiltration, particularly effective to the group of disorders showing a quantity of infiltration by lymphocytes and monocytes compared with neutrophils, or a group showing a large population of lymphocytes and monocytes in the infiltrated leukocytes.

Further, since the compound of the present invention has a specific binding property to neutrophils as well as described in the prior art, the compound is also effective to a group of disorders showing a quantity of infiltration by neutrophils compared with those by lymphocytes and monocytes, or a group showing a large population of neutrophils in the infiltrated leukocytes. Such group of disorders includes, for example, bacterial endocarditis, cardiac infarction, bronchial pneumonia, lobar pneumonia, infiltrative tuberculosis, acute gastritis, pseudomembranous colitis, yersinia infection, ulcerative colitis, acute appendicitis, acute angiocholitis, cholecystitis, intratublar proliferative glomerulonephritis, infiltrative glomerulonephritis, acute pyelonephritis, acute salpingitis, acute cervicitis, acute mastadenitis, acute testitis, acute prostatitis, allergic angiitis, acute purulent inflammation, tuberculous megingitis, acute suppurative osteomyelitis, acute lymphadenitis, and tuberculous periarteritis.

When the compound binding to leukocytes of the present invention is used as an agent for radioisotope diagnosis, a preferable embodiment of said compound is one labeled with radioactive metal suitable for SPECT image diagnosis such as Tc-99m, In-111, Ga-67, Sn-117m, Sm-153 and Re-186, or with a radioactive metal suitable for PET image diagnosis such as Cu-64 or Ga-68. When the compound of the present invention is used as a radioactive therapeutic agent, a preferred embodiment of said compound is one labeled with a radioactive metal such as Y-90, Re-186 or Re-188. When the compound of the present invention is used as a contrast medium for MRI image diagnosis, a preferred embodiment of said compound is one labeled with a paramagnetic metal such as Cu, Fe or Gd in a coordinated state.

Labeling of the compound binding to leukocytes of the present invention with Tc-99m, Re-186 and Re-188 can be performed according to the common method. Namely, the labeled compound can be prepared by dissolving said compound in saline or an aqueous buffer solution or the like, followed by addition of a reducing agent such as stannous chloride, then mixing with a sodium pertechnetate solution or a sodium perrhenate solution. For labeling with Cu, Cu-64, Fe, Mn, Gd or In-111, the labeled compound binding to leukocytes of the present invention can be prepared by mixing the compound with a slightly acidic aqueous solution containing an ion of Cu, Cu-64, Fe, Mn, Gd or In-111. In the case of labeling with Ga-67, Ga-68 or Y-90, the labeled compound binding to leukocytes can be prepared by mixing said compound with a slightly acidic or a slightly alkaline aqueous solution containing ions of Ga-67, Ga-68 or Y-90.

When the compound labeled with a radioactive metal is used as an agent for radioisotope diagnosis or a radioactive therapeutic agent, or the compound labeled with a paramagnetic metal is used as a contrast medium for MRI, the labeled compounds prepared according to the above method may be used after additional purification by HPLC to remove impurities and unreacted ions of pertechnetate ion, perrhenate ion, In-111 ion, Cu ion, Cu-64 ion, Ga-67 ion, Ga-68 ion, Fe ion, Mn ion, Gd ion and Y-90 ion.

The compound labeled with a radioactive metal or a paramagnetic metal may be mixed with pharmacologically acceptable additives to prepare an agent for radioisotope diagnosis, a radioactive therapeutic agent, or a contrast medium for MRI. These additives include, for example, pharmacologically acceptable stabilizers such as ascorbic acid and p-aminobenzoic acid, pH adjusters such as aqueous buffer solution, excipients such as D-mannitol, agents useful for ameliorating radiochemical purity such as citric acid, tartaric acid, malonic acid, sodium gluconate and sodium glucoheptonate. Further, the medicinal composition can be provided in a form of a kit for on site preparation by mixing these additives and freeze dried, which is particularly useful as an agent for radioisotope diagnosis of the present invention.

The agent for radioisotope diagnosis, the radioactive therapeutic agent or the contrast medium for MRI containing the compound binding to leukocytes of the present invention in a labeled state with a radioactive metal can be administrated through a commonly used parenteral route such as intravenous administration. Dosage and radioactivity of the composition which are thought to enable the imaging and medical treatment are determined considering various conditions such as body weight and age of the patient, suitable radioactive imaging instrument, MRI measuring instrument and state of the disease.

For human use, the dosage of diagnostic agent containing the compound labeled with Tc-99m is in the range of 37 MBq to 1110 MBq, preferably in the range of 185 MBq to 1110 MBq as a radioactivity of Tc-99m. In the case of therapeutic agent containing the compound labeled with Re-186 or Re-188, the dosage is in the range of 37 MBq to 18500 MBq, preferably in the range of 370 MBq to 7400 MBq as a radioactivity. In the case of therapeutic agent containing the compound labeled with Y-90, the dosage is in the range of 37 MBq to 3700 MBq, preferably in the range of 37 MBq to 1110 MBq as a radioactivity. The dosage of the compound labeled with other radioactive metals is almost the same. The dosage of a diagnostic agent containing the compound labeled with a paramagnetic metal such as Gd, Fe, Mn and Cu is variable corresponding to a host to be treated, sensitivity of the MR imaging instrument, target tissue of the imaging experiment, specific manner of administration and intended efficacy of the use. However, a specific medication for a specific patient depends on various factors including activity (induced relaxation) of the specific reagent to be used, age, body weight, general health condition, sexuality, meal, administration time, excretion speed, combination of agents, and judgment by a doctor in attendance.

Effective level of dosage of the labeled compound is between about 0.1 μmol/kg body weight and about 1000 μmol/kg of body weight per day, preferably between about 0.5 μmol/kg body weight and about 300 μmol/kg body weight per day. The representative preparation contains the labeled compound in an amount of about 1 mM to 1000 mM, preferably about 10 mM to 500 mm.

Hereinbelow, the present invention is described in more detail using Examples, but the scope of the present invention should not be limited thereto. The measuring methods for the compounds obtained and reagents used in Examples are described below.

(1) Gamma counter: The measurement of distribution of the labeled compound in blood was performed using Auto-Well Gamma Counter (manufactured by ALOKA Corporation, Japan), and the measurement of distribution of the labeled compound in a body was performed using NaI Single Channel Analyzer (manufactured by OHYO KOKEN KOGYO CO., LTD., Japan).
(2) Gamma camera: GMS-550U (manufactured by TOSHIBA MEDICAL SYSTEMS CORPORATION, Japan) was used.
(3) Reversed phase HPLC: Reversed phase column Millipore Puresil 5 μm C18 (4.6×150 mm) (manufactured by Millipore Corporation, USA) was used.
(4) All of the peptide compounds were synthesized by the solid phase peptide synthesis method.
(5) $^{99m}TcO_4^-$: An eluate as a saline solution from $^{99}Mo$/$^{99m}Tc$ generator (NIHON MEDI-PHYSICS CO., LTD., Japan) was used.
(6) All of the reagents used were extra pure grade.
(7) All of the experimental animals were fed for one week under the conditions of light-dark cycle of every 12 hours before use. During the period, intake of feed and water was kept free.

EXAMPLES

Example 1

Synthesis of Peptides
Following peptides were synthesized by the solid phase peptide synthesis and used in Examples hereinbelow.

Compounds Binding to Leukocytes of the Present Invention
Peptide 3: formyl-Nle-Leu-Phe-Nle-Tyr-Lys(NH$_2$)-ε-(-Ser-Cys-Gly-Asn);
Peptide 4: formyl-Nle-Leu-Phe-Nle-Tyr-Lys(NH$_2$)-ε-(-Ser-Cys-Asp-Asp);
Peptide 5: formyl-Nle-Leu-Phe-Nle-Tyr-Lys(NH$_2$)-ε-(-Ser-Cys-Gly-Asp);
Peptide 6: formyl-Nle-Leu-Phe-Nle-Tyr-Lys(NH$_2$)-ε-(-Ser-D-Arg-Asp-Cys-Asp-Asp);
Peptide 7: formyl-Nle-Leu-Phe-Nle-Tyr-Lys(NH$_2$)-ε-(-Ser-cyclam tetracarboxylic acid);
Peptide 8: formyl-Nle-Leu-Phe-Lys(NH$_2$)-ε-(-Ser-D-Ser-Asn-D-Arg-Cys-Asp-Asp);
Peptide 9: formyl-Nle-Leu-Phe-Nle-Tyr-Lys(NH$_2$)-ε-(-Ser-D-Arg-DTPA);
Peptide 13: formyl-Nle-Leu-Phe-Nle-Tyr-Lys(NH$_2$)-ε-(-Ser-Cyclam butyric acid);
Peptide 14: formyl-Nle-Leu-Phe-Nle-Tyr-Lys(NH$_2$)-ε-(-Ser-D-Arg-Asp-cyclam butyric acid);
Peptide 15: formyl-Nle-Leu-Phe-Nle-Tyr-Lys(NH$_2$)-ε-(-Ser-D-Ser-Asn-cyclam butyric acid);
Peptide 16: acetyl-Nle-Leu-Phe-Nle-Tyr-Lys(NH$_2$)-ε-(-Ser-D-Arg-Asp-Cys-Asp-Asp);
Peptide 17: carbamyl-Nle-Leu-Phe-Nle-Tyr-Lys(NH$_2$)-ε-(-Ser-D-Arg-Asp-Cys-Asp-Asp); and
Peptide 18: methyl-Nle-Leu-Phe-Nle-Tyr-Lys(NH$_2$)-ε-(-Ser-D-Arg-Asp-Cys-Asp-Asp).

In the above peptides, cyclam tetracarboxylic acid, DTPA and cyclam butyric acid mean 1,4,8,11-tetraazacyclotetradecane-1,4,8,11-tetraacetic acid, diethylenetriamine pentaacetic acid and 1,4,8,11-tetraazacyclotetradecane-butyric acid, respectively.

Control Peptides
Peptide 1: formyl-Nle-Leu-Phe-Nle-Tyr-Lys-Glu-Cys;
Peptide 2: formyl-Nle-Leu-Phe-Nle-Tyr-Lys(NH$_2$)-ε-(-Cys-Asn-Asp);
Peptide 10: formyl-Met-Leu-Phe-Lys-ε-(-Gly-Gly-Cys);
Peptide 11: formyl-Met-Leu-Phe-Lys-ε-(-Gly-Gly-Ac-S-Bzl); and
Peptide 12: formyl-Met-Leu-Phe-Lys-ε-(-Gly-Asp-Ac-S-Bzl).

Synthesis of Peptide 3
Using the peptide synthesizer (Model 430A, Applied Biosystems), the peptide was synthesized under the condition of 0.5 mM scale in MBHA resin (p-methoxy-benzhydrylamine resin hydrochloride, 1% divinylbenzene-polystyrene copolymer) by means of Boc method. The side chain of Lys residue in the C-terminal was protected with a Fmoc group. After extension of the peptide chain and formylation of the N-terminal amino group, the side chain Fmoc group of the Lys residue was cleft by 20% piperidine/DMF to extend the peptide chain toward the side chain direction. The peptide was clipped off under the reaction in a mixture of hydrogen fluoride anhydride: p-cresol (80:20) at −2° C. to −5° C. for 1.0 hour.

Purification was performed in a liquid chromatography (HPLC) by using a column: YMC-Pack ODS-A SH-365-5 (30×250 mm) and eluent A: 0.1% TFA/purified water and eluent B: 0.1% TFA/acetonitrile under the concentration gradient condition from A to B at the eluting rate of 20 ml/min. Main peak fractions were collected and freeze dried to obtain the objective peptide. Purity of the thus obtained peptide was determined by means of the reversed phase HPLC.

Synthesis could also be performed as well by using a preload resin in place of MBHA resin.

After the peptide was hydrolyzed in 6 M hydrochloric acid at 110° C. for 22 hours, an amino acid composition corresponding to the obtained main peak was determined and confirmed to be the objective peptide 3, then the peak coinciding with the amino acid composition was freeze dried to obtain the objective peptide 3. Molecular weight of the peptide was confirmed to be identical with the theoretical value by mass spectrometry (hereinafter designated as ESI-MS) for determining molecular weight. Analytical values of the amino acid composition (number of each amino acid in a molecule) of the obtained peptide 3 were shown hereinbelow. In a parenthesis, theoretical values of the amino acid composition (number of each amino acid in a molecule) of the objective peptide were shown.

Peptide 3: Asp: (1) 1.02; Ser: (1) 0.93; Gly: (1) 1.03; Tyr: (1) 1.00; Phe: (1) 1.01; Lys: (1) 1.00, $NH_3$ (2) 2.10; Cys: (1) 0.86; Leu: (1)+Nle (2) 2.88

Further, molecular weight of the peptide 3 obtained by ESI-MS is shown hereinbelow. The numerical value in the parenthesis indicates a theoretical value of the molecular weight of the objective peptide. ESI-MS: MW=1183.9 (1184.4)

Synthesis of Other Peptides

Other peptides were synthesized and identified in the similar way. Since the peptide 1, peptide 10, peptide 11 and peptide 12-were peptides which were not amidated in the C-terminals thereof, these were synthesized by the similar way as shown in the synthesis of the peptide 3 by using HMP resin (4-hydroxy-methyl-phenoxy methyl-copolystyrene-1% divinyl-benzene resin) in place of MBHA resin. Analytical values of amino acid composition and ESI-MS used for identifying each peptide are shown hereinbelow. For the peptide 1 and the peptide 10, only amino acid compositions are shown.

Peptide 1=Glu:(1) 1.04, Leu:(1) 0.99, Tyr:(1) 0.98, Phe:(1) 0.99, Lys:(1) 1.00, Cys:(1) 0.97, Nle:(2) 2.03.

Peptide 2=Asp:(2) 2.00, Leu:(1) 0.86, Tyr:(1) 1.00, Phe:(1) 1.01, Lys:(1) 1.00, $NH_3$:(2) 1.94, Cys:(1) 0.88, Nle:(2) 2.10, ESI-MS: MW=1,155.0 (1,155.4).

Peptide 4=Asp:(2) 2.00, Ser:(1) 0.90, Tyr:(1) 0.99, Phe:(1) 1.01, Lys:(1) 1.00, $NH_3$:(1) 1.10, Leu:(1)+Nle:(2) 2.84, Cys:(1) 0.92, ESI-MS: MW=1,243.0 (1,243.4).

Peptide 5=Asp:(1) 1.00, Ser:(1) 0.90, Gly:(1) 1.01, Tyr:(1) 0.97, Phe:(1) 1.00, Lys:(1) 1.03, $NH_3$:(1) 1.18, Leu:(1)+Nle:(2) 2.86, Cys:(1) 0.91, ESI-MS: MW=1,185.1 (1,185.4).

Peptide 6=Asp:(3) 3.19, Ser:(1) 0.97, Tyr:(1) 0.97, Phe:(1) 0.98, Lys:(1) 1.00, $NH_3$:(1)1.20, Leu:(1)+Nle:(2) 2.80, Arg:(1) 1.06, Cys:(1) 0.92, ESI-MS: MW=1,514.4 (1,514.7).

Peptide 7=Ser:(1) 0.92, Tyr:(1) 1.00, Phe:(1) 1.02, Lys:(1) 1.00, $NH_3$:(1)1.15, Leu:(1)+Nle: (2) 2.89, ESI-MS: MW=1,324.3 (1,324.6).

Peptide 8=Asp:(3) 2.94, Ser:(2) 1.80, Leu:(1) 1.01, Phe:(1) 1.00, Lys:(1) 1.01, $NH_3$:(2) 2.10, Nle:(1) 0.95, Cys:(1) 1.01 ESI-MS: MW=1,324.1 (1,324.5).

Peptide 9=Ser:(1) 0.91, Tyr:(1) 1.00, Phe:(1) 0.99, Lys:(1) 1.00, $NH_3$:(1) 1.23, Leu:(1)+Nle:(2) 2.87, Arg:(1) 1.00, ESI-MS: MW=1,441.4 (1,441.6).

Peptide 10=Gly:(2) 1.88, Met:(1) 0.98, Phe:(1) 1.00, Lys:(1) 1.02, Leu:(1) 1.04.

Peptide 11=Gly:(2) 1.94, Met:(1) 0.91, Phe:(1) 1.00, Lys:(1) 1.02, Leu:(1) 1.01, ESI-MS: MW=842.5 (842.4).

Peptide 12=Asp:(1) 0.94, Gly:(1) 0.92, Met:(1) 0.96, Phe:(1) 1.00, Lys:(1) 1.01, Leu(1) 1.00, ESI-MS: MW=901.5 (902.1).

Peptide 13=Ser:(1) 0.92, Tyr:(1) 1.00, Phe:(1) 1.01, Lys:(1) 1.01, $NH_3$:(1) 1.11, Leu:(1)+Nle:(2) 2.88, ESI-MS: MW=1,178.3 (1,178.5).

Peptide 14=Asp:(1) 1.01, Ser:(1) 0.91, Tyr:(1) 1.00, Phe:(1) 1.00, Lys:(1) 1.01, $NH_3$:(1) 1.06, Leu:(1)+Nle:(2) 2.89, Arg:(1) 1.00, ESI-MS: MW=1,449.6 (1,449.8).

Peptide 15=Asp:(1) 1.01, Ser:(2) 1.77, Tyr:(1) 0.98, Phe:(1) 1.00, Lys:(1) 1.01, $NH_3$:(2) 2.09, Leu:(1)+Nle:(2) 2.87, ESI-MS: MW=1,379.5 (1,379.7).

Peptide 16=Asp:(3) 3.02, Ser:(1) 0.93, Tyr:(1) 1.00, Phe:(1) 1.00, Lys:(1) 1.00, $NH_3$:(1) 1.10, Leu:(1)+Nle:(2) 2.86, Arg:(1) 1.01, Cys:(1) 1.07, ESI-MS: MW=1,528.3 (1,528.7).

Peptide 17=Asp:(3) 2.95, Ser:(1) 0.91, Tyr:(1) 1.00, Phe:(1) 1.00, Lys:(1) 1.00, $NH_3$:(1) 1.79, Leu:(1)+Nle:(2) 2.58, Arg:(1) 1.00, Cys:(1) 1.00 ESI-MS: MW=1,529.4 (1,529.7).

Peptide 18=Asp:(3) 2.99, Ser:(1) 0.92, Tyr:(1) 0.88, Phe:(1) 0.97, Lys:(1) 0.97, $NH_3$:(1) 1.12, Leu:(1)+Nle:(1) 1.85, Arg:(1) 1.00, Cys:(1) 1.03, MeNle:(1)0.95 ESI-MS: MW=1,500.5 (1,500.7).

Example 2

Tc-99m Labeling of Peptide 1, Peptide 2, Peptide 3, Peptide 4, Peptide 5, Peptide 6, Peptide 7, Peptide 8, Peptide 9, Peptide 10, Peptide 13, Peptide 14, Peptide 15, Peptide 16, Peptide 17 and Peptide 18

(1) Method

A solution of Tc-99m-sodium pertechnetate (hereinafter designated as $^{99m}TcO4^-$), 1.1–3.0 GBq, was added into a vial containing a mixture of glucoheptonic acid 40.3 μmol/300 μl and stannous chloride solution 130 nmol/50 μl to make the total volume 1.35 ml. The mixture was reacted at room temperature for 30 minutes with stirring and occasional tumbling. A part thereof was collected and the labeling rate of Tc-99m of Tc-99m-glucoheptonic acid was confirmed to be 95% or more.

Each of sixteen peptides obtained in Example 1 was dissolved in dimethylformamide (DMF) and a concentration thereof in each solution was adjusted to 0.25–12.5 nmol/200 μl with ultra pure water, 10 mM phosphate buffer containing 0.9% NaCl, pH 7.4, (hereinafter designated as PBS) or 10 mM carbonate buffer, pH 8.0 (hereinafter designated as CB). To each solution was added Tc-99m glucoheptonic acid solution 200 μl, mixed by stirring and reacted at 100° C.–120° C. for 10 minutes. After the labeling was completed, a part of the reaction mixture was collected and the labeling rate of Tc-99m was determined by using HPLC. The conditions of HPLC are as follows. Column: Millipore puresil 5 μm C18 (4.6×150 mm); flow rate: 1 ml/min.; detection wavelength: 220 nm; radioactivity detector: NaI single channel analyzer; eluent A: 0.1% trifluoroacetic acid (hereinafter designated as TFA)/purified water; eluent B: 0.1% TFA/acetonitrile; and concentration gradient: 0 minutes (20% B)→20 minutes (50% B)

(2) Results

Figure 2:
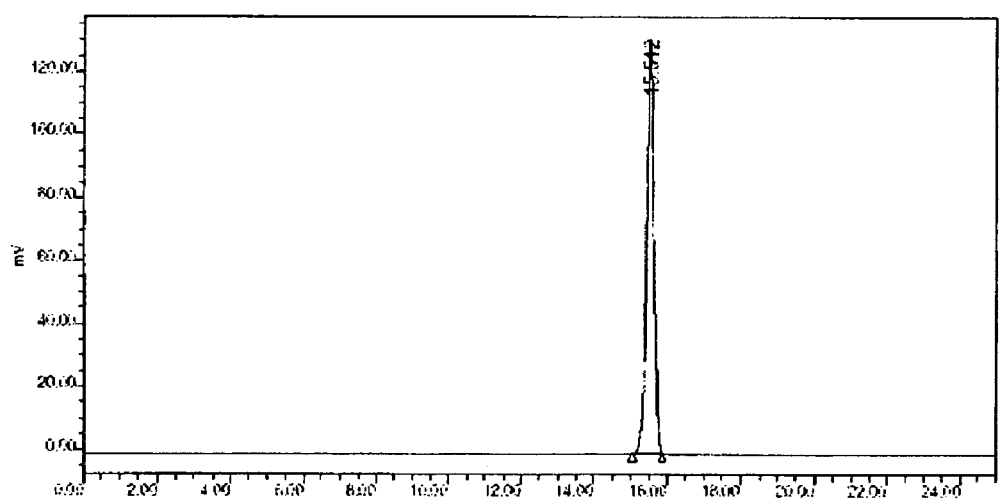
FIG. 2 shows a HPLC chromatogram of Tc-99m-peptide 6.

In Table 1, labeling rates of 16 species of Tc-99m labeled peptides are shown. Results of peptide 4 and peptide 6 as the representative chromatogram in HPLC analysis of the obtained labeled compounds are shown in FIG. 1 and FIG. 2, respectively. Single labeled product was recognized in each peptide. Results of the labeling rates shown in Table 1 indicated that high Tc-99m labeling with 80% or more could be performed.

TABLE 1

Labeling rate of Tc-99m labeled peptide

| Labeled compound | Radiochemical purity (%) |
|---|---|
| Tc-99m-peptide 1 | 94.4% |
| Tc-99m-peptide 2 | 92.3% |
| Tc-99m-peptide 3 | 97.6% |
| Tc-99m-peptide 4 | 99.6% |
| Tc-99m-peptide 5 | 100% |
| Tc-99m-peptide 6 | 100% |
| Tc-99m-peptide 7 | 100% |
| Tc-99m-peptide 8 | 98.5% |
| Tc-99m-peptide 9 | 97.7% |
| Tc-99m-peptide 10 | 91.7% |
| Tc-99m-peptide 13 | 82.0% |
| Tc-99m-peptide 14 | 81.0% |
| Tc-99m-peptide 15 | 96.0% |
| Tc-99m-peptide 16 | 94.5% |
| Tc-99m-peptide 17 | 97.2% |
| Tc-99m-peptide 18 | 98.9% |

Example 3

Distribution in Rabbit Blood (1) The peptides which were labeled with Tc-99m in Example 2 (Peptide 3, peptide 4, peptide 6, peptide 8, peptide 9, peptide 12, peptide 13, peptide 14, peptide 15, peptide 16, peptide 17 and peptide 18) were purified by separating into unlabeled peptides and labeled peptides using a reversed phase HPLC under the same conditions of HPLC as in Example 2. Gradient elution was performed under the condition of 20%→50% (0.1% TFA acetonitrile/0.1% TFA water): 0→20 minutes. Subsequently, Percoll density-gradient solution was prepared. To an undiluted Percoll solution (Pharmacia Biotech Inc.) (specific gravity 1.130 g/ml) 90 ml, 1.5 M NaCl 10 ml was added to prepare an isotonic solution equal to the physiological saline. This solution was diluted by adding physiological saline to prepare 1.096, 1.077 and 1.063 g/ml of Percoll solutions. The thus prepared 1.096, 1.077 and 1.063 g/ml of Percoll solutions, each 1 ml, were layered over in a 15 ml tube. It was confirmed to have the desired density by using density marker beads (red: 1.062; blue: 1.075; orange: 1.087; and green: 1.098). The blood used for the test was collected from the auricular vein of specific pathogen free (SPF), healthy New Zealand White (NZW) strain rabbit, male, body weight about 2 kg.

For examining distribution in the blood of rabbit with infection as an acute inflammation model, the blood of rabbit inflamed with *Staphylococcus aureus* was used in place of the blood of the healthy rabbit. About $10^8$ viable counts of *Staphylococcus aureus* were suspended in physiological saline 1 ml, and the bacterial suspension 100 μl was administered intramuscularly into the right calf of New Zealand White (NZW) strain rabbit, male, body weight about 2 kg. The blood was collected from the auricular vein of the rabbit after about 24 hours and used for the examination.

For examining distribution in the blood of a rabbit with ulcerative colitis as a chronic inflammantion model, the blood of rabbit inflamed with 2,4,6-trinitrobenzenesulfonic acid (TNBS) was used in place of the blood of the healthy rabbit. A model rabbit of ulcerative colitis was prepared according to the method of Anthony et al. (Anthony et al. Int. J. Exp. Path., 76, 215–224, 1995). TNBS 360 mg was dissolved in ultra pure water 4 ml and ethanol 3.2 ml was added thereto to prepare 50.0 mg/ml 46% ethanol/physiological saline. A tube was inserted per anum in about 15 cm depth into the intestine of nembutalized New Zealand White (NZW) strain rabbit, 7 weeks age, weighed 1.3–1.4 kg, male, fasted before one day, and air 3 ml was infused. A solution of TNBS/46% ethanol/physiological saline 0.8 ml was infused subsequently and massaged and tilted the posture for 2 minutes. After 4–5 days, the blood was collected from the auricular vein of the rabbit and used for the examination.

The blood of rabbit, 2 ml each, was warmed at 37° C. for 5 minutes in a warm bath. Each sample of four Tc-99m-peptides 3 μl (111 MBq/ml, Tc-99m-peptide $1.8 \times 10^{-11}$ mol/ml) purified by HPLC was added thereto and incubated for 30 minutes. The blood sample was Percoll density gradient solution. The layered sample was centrifuged at 2000 rpm (800×g) for 15 minutes. After the centrifugation, the tube was frozen and each fraction was cut off by using a cutter, then the radioactivity of each fraction was measured using Auto-Well Gamma Counter to determine the radioactivity distribution of four types of Tc-99m-peptide to the each blood component.

(2) Results

Figure 3:
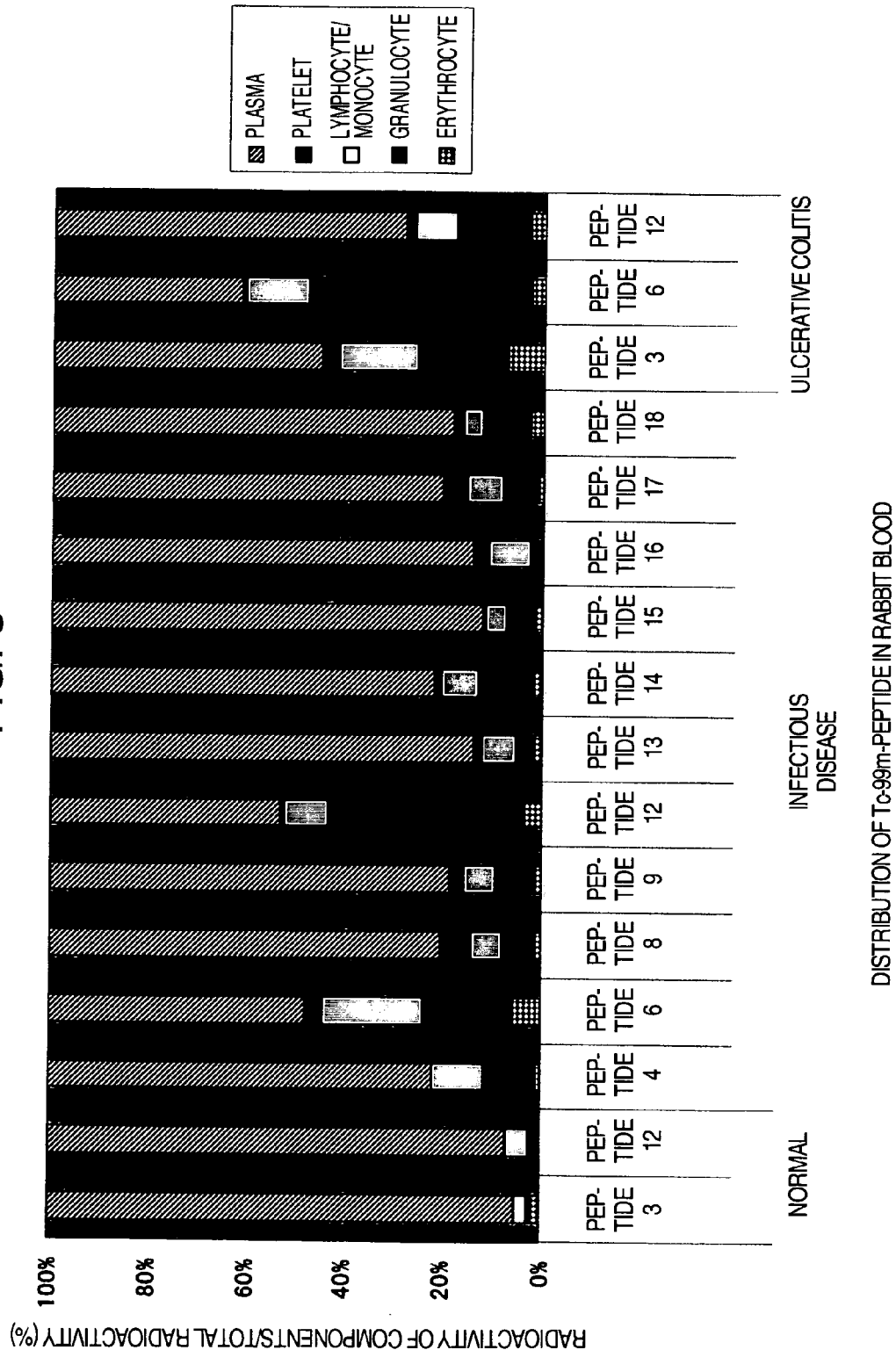
FIG. 3 shows a distribution of Tc-99m-peptide in the rabbit blood.
Figure 4:
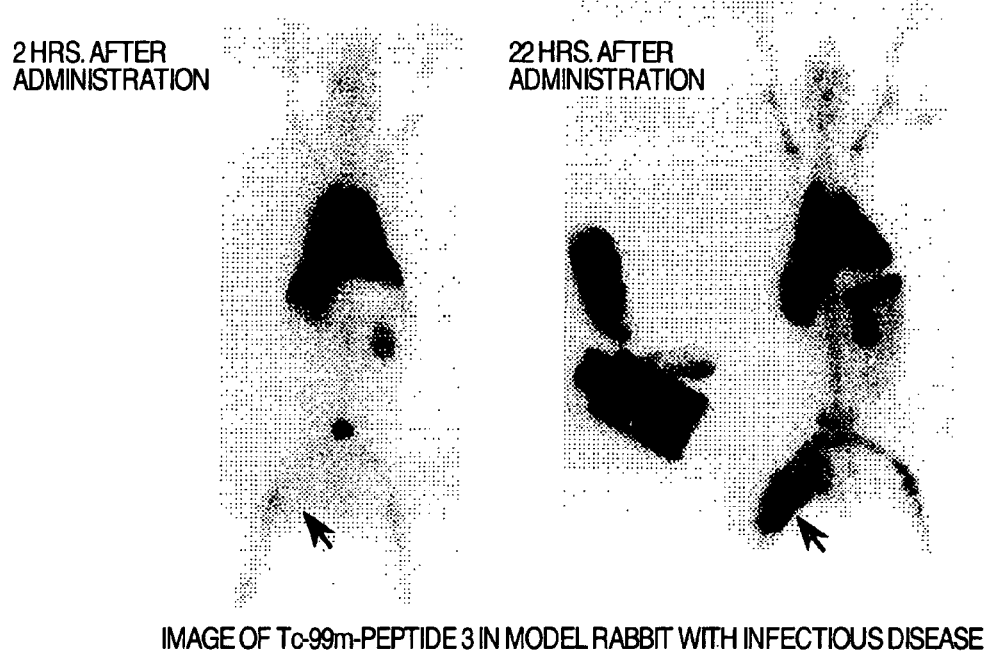
FIG. 4 shows an image of Tc-99m-peptide 3 in a model rabbit with infectious disease. Left side is an image 2 hours after the administration; right side is an image 22 hours after the administration.
Figure 5:
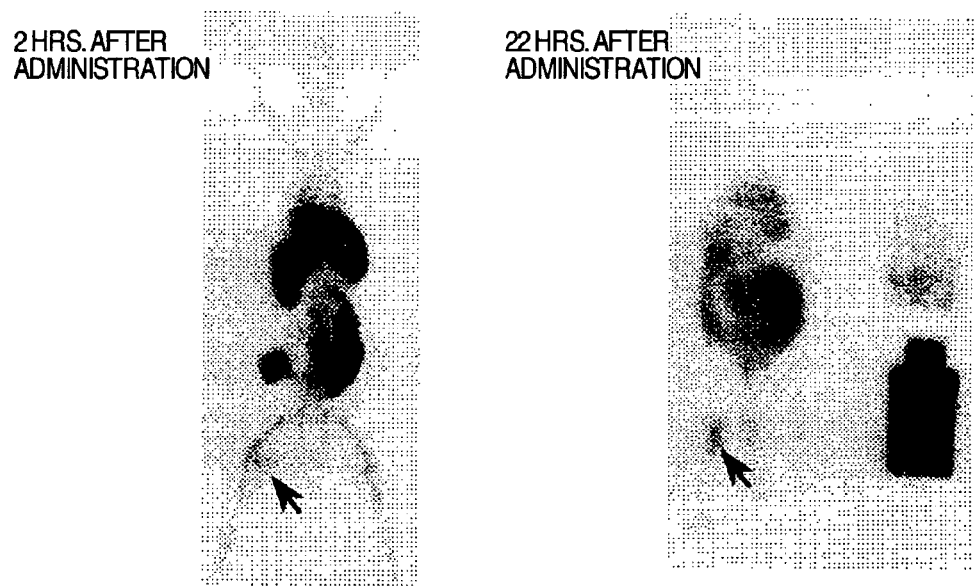
FIG. 5 shows an image of Tc-99m-peptide 4 in a model rabbit with infectious disease. Left side is an image 2 hours after the administration; right side is an image 22 hours after the administration.
Figure 6:
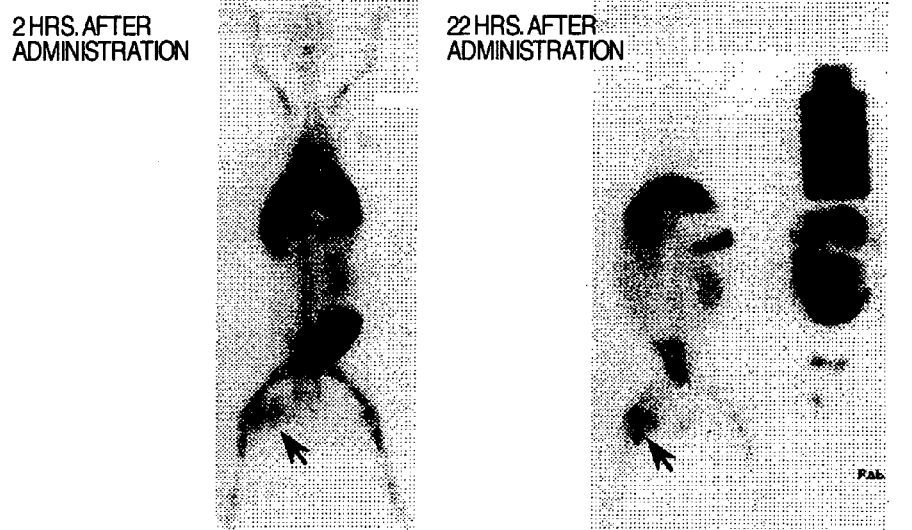
FIG. 6 shows an image of Tc-99m-peptide 6 in a model rabbit with infectious disease. Left side is an image 2 hours after the administration; right side is an image 22 hours after the administration.
Figure 7:
FIG. 7 shows an image of Tc-99m-peptide 8 in a model rabbit with infectious disease. Left side is an image 2 hours after the administration; right side is an image 5 hours after the administration.
Figure 8:
FIG. 8 shows an image of Tc-99m-peptide 9 in a model rabbit with infectious disease. Left side is an image 2 hours after the administration; right side is an image 5 hours after the administration.
Figure 9:
FIG. 9 shows an image of Tc-99m-peptide 12 in a model rabbit with infectious disease. Left side is an image 2 hours after the administration; right side is an image 22 hours after the administration.
Figure 10:
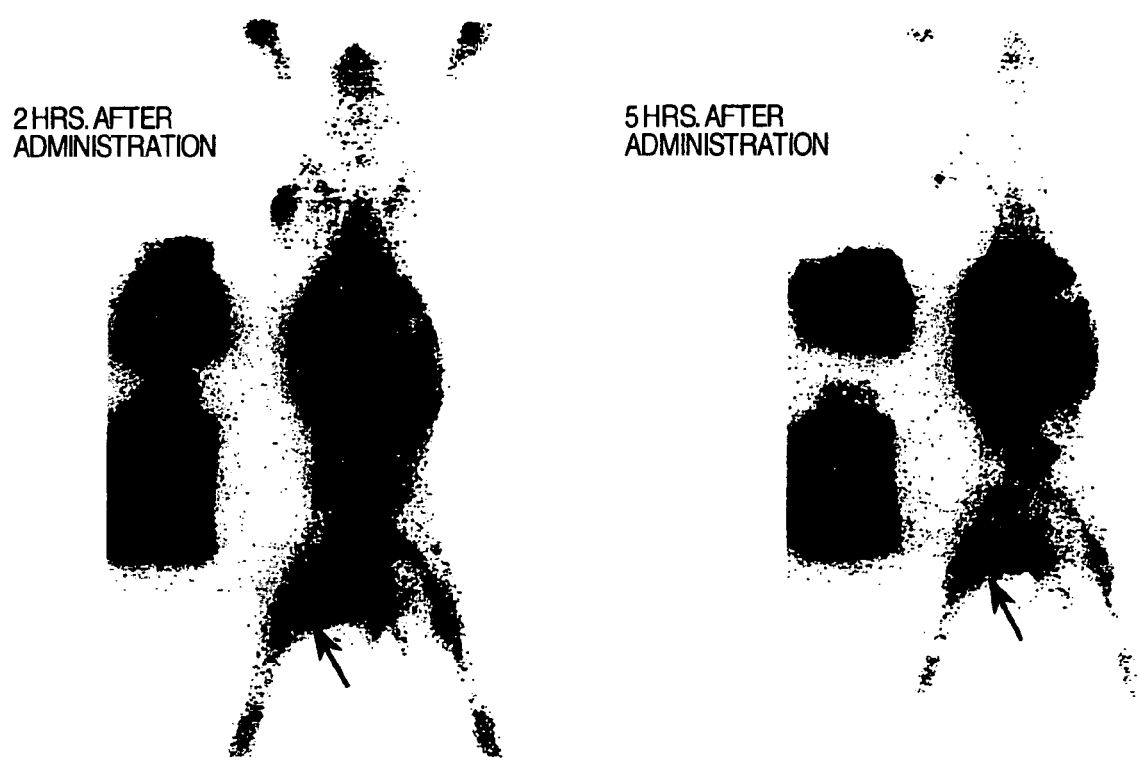
FIG. 10 shows an image of Tc-99m-peptide 13 in a model rabbit with infectious disease. Left side is an image 2 hours after the administration; right side is an image 5 hours after the administration.
Figure 11:
FIG. 11 shows an image of Tc-99m-peptide 14 in a model rabbit with infectious disease. Left side is an image 2 hours after the administration; right side is an image 5 hours after the administration.
Figure 12:
FIG. 12 shows an image of Tc-99m-peptide 15 in a model rabbit with infectious disease. Left side is an image 2 hours after the administration; right side is an image 5 hours after the administration.
Figure 13:
FIG. 13 shows an image of Tc-99m-peptide 16 in a model rabbit with infectious disease. Left side is an image 2 hours after the administration; right side is an image 5 hours after the administration.
Figure 14:
FIG. 14 shows an image of Tc-99m-peptide 17 in a model rabbit with infectious disease. Left side is an image 2 hours after the administration; right side is an image 5 hours after the administration.
Figure 15:
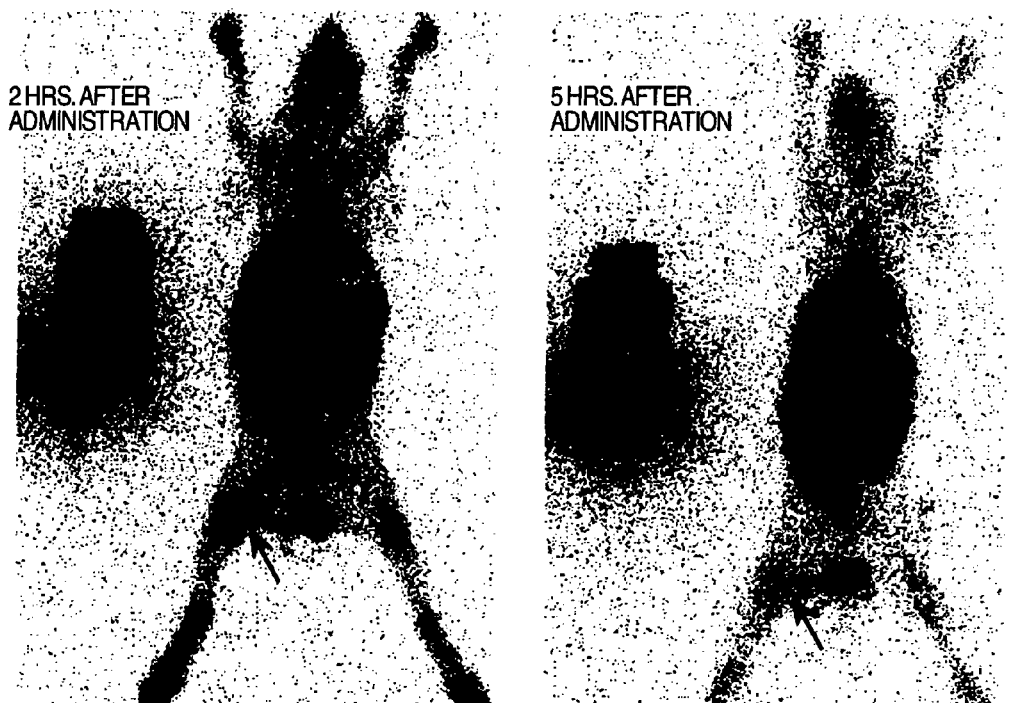
FIG. 15 shows an image of Tc-99m-peptide 18 in a model rabbit with infectious disease. Left side is an image 2 hours after the administration; right side is an image 5 hours after the administration.

According to the leukocyte counts 1000–8000 cells/μl from the hematological parameter of rabbits and the number of receptor FPR, 100,000–120,000/cell, found in the reference, estimated numbers of the receptor FPR in the blood of rabbits were calculated as $0.17–1.6 \times 10^{-12}$ mol/ml, and ratios of peptide/receptor in rabbits were 0.01–0.11. Results showing percentages of radioactivity in each blood component to the radioactivity in the whole blood are shown in FIG. 3. Results showing percentages of radioactivity of granulocyte fraction to the radioactivity in the total leukocytes, and a radioactivity of lymphocyte and monocyte fraction for the radioactivity in the total leukocytes are shown in Table 2 and Table 3.

In the healthy SPF rabbit blood, distributions of Tc-99m-peptide 3 and Tc-99m-peptide 12 in the granulocyte fraction and in the lymphocyte and monocyte fraction were 5% or less of the radioactivity in the whole blood and no strong binding was observed.

In the blood of rabbits with infectious disease caused by *Staphylococcus aureus*, a radioactivity distribution of Tc-99m-peptide 4 in the granulocyte fraction was 10.78% of the radioactivity in the whole blood and that of Tc-99m-peptide 4 in the lymphocyte and monocyte fraction was 10.22% of the radioactivity in the whole blood after the incubation for 30 minutes. The radioactivity of the granulocyte fraction was 50.22% for the radioactivity of the whole leukocyte, and the radioactivity of the lymphocyte and monocyte fraction was 49.78% for the radioactivity of the whole leukocyte. A radioactivity distribution of Tc-99m-peptide 6 in the granulocyte fraction was 18.27% of the radioactivity in the whole blood and that of Tc-99m-peptide 6 in the lymphocyte and monocyte fraction was 20.21% of the radioactivity in the whole blood after the incubation for 30 minutes. The radioactivity of the granulocyte fraction was 47.65% for the radioactivity of the whole leukocyte, and the radioactivity of the lymphocyte and monocyte fraction was 52.35% for the radioactivity of the whole leukocyte. In the Tc-99m labeled compounds of peptide 8, peptide 9, peptide 13, peptide 14, peptide 15, peptide 16, peptide 17 and peptide 18, 10% or more of the radioactivity of the whole blood were distributed in the leukocyte, and about 27% to about 77% of the radioactivity of the whole blood were distributed in the lymphocyte and monocyte fraction.

A radioactivity distribution of the control Tc-99m-peptide 12 in the granulocyte fraction was 39.73% of the radioactivity in the whole blood and that of Tc-99m-peptide 12 in the lymphocyte and monocyte fraction was 8.89% of the radioactivity in the whole blood after the incubation for 30 minutes. The radioactivity of the granulocyte fraction was 81.58% for the radioactivity of the whole leukocyte, and the radioactivity of the lymphocyte and monocyte fraction was 18.42% for the radioactivity of the whole leukocyte. From these results, it has become apparent that the distribution of Tc-99m labeled compounds of peptide 4, peptide 6, peptide 8, peptide 9, peptide 13, peptide 14, peptide 15, peptide 16, peptide 17 and peptide 18 as a part of the present invention in the lymphocyte and monocyte fraction was larger than that of the conventional peptide, Tc-99m-peptide 12, in the blood of rabbits with infectious disease caused by *Staphylococcus aureus*.

In the blood of ulcerative colitis model rabbits prepared by TNBS, as shown in FIG. 3, a radioactivity distribution of Tc-99m-peptide 3 in the granulocyte fraction was 18.44% of the radioactivity in the whole blood and that of Tc-99m-peptide 3 in the lymphocyte and monocyte fraction was 15.94% of the radioactivity in the whole blood after the incubation for 30 minutes. The radioactivity of the granulocyte fraction was 53.72% for the radioactivity of the whole leukocyte, and the radioactivity of the lymphocyte and monocyte fraction was 46.28% for the radioactivity of the whole leukocyte as shown in Table 3. A radioactivity distribution of Tc-99m-peptide 6 in the granulocyte fraction was 45.44% of the radioactivity in the whole blood and that of Tc-99m-peptide 6 in the lymphocyte and monocyte fraction was 12.60% of the radioactivity in the whole blood after the incubation for 30 minutes. The radioactivity of the granulocyte fraction was 78.27% for the radioactivity of the whole leukocyte, and the radioactivity of the lymphocyte and monocyte fraction was 21.73% for the radioactivity of the whole leukocyte. A radioactivity distribution of the control Tc-99m-peptide 12 in the granulocyte fraction was 15.10% of the radioactivity in the whole blood and that of Tc-99m-peptide 12 in the lymphocyte and monocyte fraction was 8.34% of the radioactivity in the whole blood after the incubation for 30 minutes. The radioactivity of the granulocyte fraction was 64.66% for the radioactivity of the whole leukocyte, and the radioactivity of the lymphocyte and monocyte fraction was 35.34% for the radioactivity of the whole leukocyte.

From these results, it has become apparent that the distributions of Tc-99m-peptide 3 and Tc-99m-peptide 6 as a part of the present invention in the lymphocyte and monocyte fraction were larger than that of the conventional peptide, Tc-99m-peptide 12, in the blood of ulcerative colitis model rabbits.

From the above, it was shown that the peptide of the present invention was bound more strongly with the lymphocytes and the monocytes than with the granulocytes as compared with the conventional Tc-99m-peptide 12, and it was confirmed that the peptide of the present invention was effective for treatment of chronic inflammation frequently infiltrated lymphocytes and monocytes.

TABLE 2

Binding rate of Tc-99m labeled peptide for leukocytes of rabbits
(Binding rate (%) for whole leukocytes, n = 3, mean ± SD)

| | Infectious disease model | |
|---|---|---|
| Labeled compound | Granulocytes | Lymphocytes and monocytes |
| Tc-99m-peptide 4 | 50.22 ± 10.31 | 49.78 ± 10.31 |
| Tc-99m-peptide 6 | 47.65 ± 2.47 | 52.35 ± 2.47 |
| Tc-99m-peptide 8 | 51.41 ± 6.39 | 48.59 ± 6.39 |
| Tc-99m-peptide 9 | 58.51 ± 2.90 | 41.49 ± 2.90 |
| Tc-99m-peptide 12 | 81.58 ± 3.58 | 18.42 ± 3.58 |
| Tc-99m-peptide 13 | 33.45 ± 3.69 | 66.55 ± 3.69 |
| Tc-99m-peptide 14 | 58.77 ± 5.64 | 41.23 ± 5.64 |
| Tc-99m-peptide 15 | 58.94 ± 6.47 | 41.06 ± 6.47 |
| Tc-99m-peptide 16 | 23.28 ± 0.73 | 76.72 ± 0.73 |
| Tc-99m-peptide 17 | 50.98 ± 0.44 | 49.02 ± 0.44 |
| Tc-99m-peptide 18 | 72.35 ± 4.24 | 27.65 ± 4.24 |

TABLE 3

Binding rate of Tc-99m labeled peptide for leukocytes of rabbits
(Binding rate (%) for whole leukocytes, n = 3, mean ± SD)

| | Ulcerative colitis model | |
|---|---|---|
| Labeled compound | Granulocytes | Lymphocytes and monocytes |
| Tc-99m-peptide 3 | 53.72 ± 10.74 | 46.28 ± 10.74 |
| Tc-99m-peptide 6 | 78.27 ± 3.16 | 21.73 ± 3.16 |
| Tc-99m-peptide 12 | 64.66 ± 4.05 | 35.34 ± 4.05 |

Example 4

Imaging of Tc-99m Labeled Compounds of Peptide 3, Peptide 4, Peptide 5 and Peptide 12 on Rabbit Infectious Disease Model, and Effectiveness on Acute Phase and Subacute Phase Inflammation (1) Method Viable *Staphylococcus aureus*, about $10^8$ counts, were suspended in physiological saline 1 ml, and the suspension 100 μl was administered intramuscularly into the right calf of the rabbit, New Zealand White strain (NZW), about 2 kg. After 24 hours, model rabbits which exhibited apparent inflammation were anesthetized with pentobarbital, and each of peptide 3, peptide 4, peptide 5, peptide 6, peptide 7, peptide 8, peptide 9, peptide 12, peptide 13, peptide 14, peptide 15, peptide 16, peptide 17 and peptide 18, which were labeled with Tc-99m, 37–74 MBq each, was administered to the ear vein. After 5 minutes, 1 hour, 2 hours, 3 hours, 4 hours, 5 hours and 22 hours from the administration, images were recorded by using a gamma camera. The time points from 5 minutes to 5 hours after the administration are the times from about 24 hours to 29 hours after initiating inflammation and corresponds to acute phase inflammation. The time point after 22 hours is the time after about 46 hours from initiating inflammation and corresponds to subacute phase inflammation.

(2) Results

Representative figures of obtained results are shown in FIG. 4, FIG. 5, FIG. 6, FIG. 7, FIG. 8, FIG. 9, FIG. 10, FIG. 11, FIG. 12, FIG. 13, FIG. 14 and FIG. 15. Regions of interest are set on the images, and ratios of counts in the region of interest of 1000 pixel for whole body counts (% injection dose (ID)/K pixel) are shown in Table 4. Ratios indicating [inflammation]/[normal muscle] (ratios of [A]/[M]) determined from the above ratios are shown in Table 5.

In the prior known Tc-99m-peptide 12, the ratio of [A]/[M] after 2 hours from the administration (26 hours after initiating inflammation, acute phase inflammation) was 10.34±3.34 (mean±standard error) (n=3), and the ratio of [A]/[M] after 22 hours from the administration (46 hours after initiating inflammation, subacute phase inflammation) was 33.94±20.76 (n=3), while the accumulation to inflammatory region was decreased from 1.66±0.63% ID/K pixel after 2 hours from the administration (26 hours after initiating inflammation) to 0.90±0.29% ID/K pixel after 22 hours from the administration (46 hours after initiating inflammation).

In Tc-99m-peptide 3 of the present invention, the ratio of [A]/[M] after 2 hours from the administration (26 hours after initiating inflammation) was 6.55±2.06 (n=5), and the ratio of [A]/[M] after 22 hours from the administration (46 hours after initiating inflammation) was 54.16±32.86 (n=5), while the accumulation to inflammatory region increased from 0.93±0.31% ID/K pixel after 2 hours from the administration (26 hours after initiating inflammation) to 3.70±2.67% ID/K pixel after 22 hours from the administration (46 hours after initiating inflammation). In Tc-99m-peptide 4, the ratio of [A]/[M] after 2 hours from the administration (26 hours after initiating inflammation) was 6.75±2.71 (n=3), and the ratio of [A]/[M] after 22 hours from the administration (46 hours after initiating inflammation) was 29.07±19.97 (n=3), which were lower values than those of the prior known Tc-99m-peptide 12, while the accumulation to inflammatory region was increased from 1.09±0.22% ID/K pixel after 2 hours from the administration (26 hours after initiating inflammation) to 1.85±0.34% ID/K pixel after 22 hours from the administration (46 hours after initiating inflammation). In Tc-99m-peptide 6, the ratio of [A]/[M] after 2 hours from the administration (26 hours after initiating inflammation) was 14.25±0.31 (n=3), and the ratio of [A]/[M] after 22 hours from the administration (46 hours after initiating inflammation) was 43.84±12.58 (n=3), while the accumulation to inflammatory region was increased from 1.22±0.05% ID/K pixel after 2 hours from the administration (26 hours after initiating inflammation) to 1.77±0.07% ID/K pixel after 22 hours from the administration (46 hours after initiating inflammation).

Generally, most of leukocytes infiltrated into inflammatory region after about 24 hours from infection consist of mainly neutrophils (occupying mostly in granulocytes), thereafter these decrease gradually and majority of infiltrated leukocytes are changed to monocytes including macrophage and lymphocyte. From the clinical standpoint, most inflammations, which require a nuclear medical test, are inflammations after the subacute phase exhibiting significant infiltration of monocytes and lymphocytes. From the above results, it was shown that the peptides of the present invention are extremely useful for the diagnosis not only in the acute phase inflammation after 26 hours from onset of inflammation (2 hours after administration) but also in the subacute phase inflammation after 46 hours from onset of inflammation (22 hours after administration).

TABLE 4

Accumulation of Tc-99m labeled peptide in inflammation on rabbit infectious disease model (% ID/K pixel)
(n = 3, Tc-99m-peptide 3: n = 5, mean ± standard deviation)

| Labeled compound | Elapse of time after administration | | | | | | |
|---|---|---|---|---|---|---|---|
| | 5 min. | 1 hr | 2 hrs | 3 hrs | 4 hrs | 5 hrs | 22 hrs |
| Tc-99m-peptide 3 | 0.39 ± 0.14 | 0.66 ± 0.18 | 0.93 ± 0.31 | 1.08 ± 0.31 | 1.39 ± 0.55 | 1.63 ± 0.72 | 3.70 ± 2.67 |
| Tc-99m-peptide 4 | 0.95 ± 0.24 | 0.91 ± 0.14 | 1.09 ± 0.22 | 1.52 ± 0.27 | 1.76 ± 0.39 | 1.84 ± 0.27 | 1.85 ± 0.34 |
| Tc-99m-peptide 6 | 0.93 ± 0.10 | 0.94 ± 0.10 | 1.22 ± 0.05 | 1.49 ± 0.14 | 1.59 ± 0.09 | 1.64 ± 0.08 | 1.77 ± 0.07 |
| Tc-99m-peptide 8 | 1.59 ± 0.38 | 0.97 ± 0.34 | 0.73 ± 0.16 | 0.60 ± 0.10 | 0.60 ± 0.14 | 0.62 ± 0.11 | not conducted |
| Tc-99m-peptide 9 | 1.39 ± 0.22 | 0.65 ± 0.11 | 0.47 ± 0.10 | 0.41 ± 0.10 | 0.42 ± 0.06 | 0.43 ± 0.03 | not conducted |
| Tc-99m-peptide 12 | 0.86 ± 0.14 | 1.31 ± 0.38 | 1.66 ± 0.63 | 1.62 ± 0.63 | 1.64 ± 0.66 | 1.59 ± 0.71 | 0.90 ± 0.29 |
| Tc-99m-peptide 13 | 1.40 ± 0.37 | 1.09 ± 0.23 | 0.68 ± 0.12 | 0.52 ± 0.10 | 0.54 ± 0.07 | 0.54 ± 0.08 | not conducted |
| Tc-99m-peptide 14 | 1.30 ± 0.20 | 0.82 ± 0.18 | 0.58 ± 0.04 | 0.44 ± 0.03 | 0.49 ± 0.00 | 0.51 ± 0.02 | not conducted |
| Tc-99m-peptide 15 | 1.36 ± 0.30 | 0.83 ± 0.02 | 0.76 ± 0.07 | 0.81 ± 0.32 | 0.90 ± 0.33 | 1.04 ± 0.28 | not conducted |
| Tc-99m-peptide 16 | 2.93 ± 0.21 | 0.85 ± 0.21 | 0.38 ± 0.05 | 0.23 ± 0.05 | 0.16 ± 0.06 | 0.13 ± 0.03 | not conducted |
| Tc-99m-peptide 17 | 2.59 ± 0.70 | 1.13 ± 0.07 | 0.62 ± 0.03 | 0.47 ± 0.04 | 0.38 ± 0.07 | 0.36 ± 0.12 | not conducted |
| Tc-99m-peptide 18 | 2.14 ± 0.16 | 0.75 ± 0.26 | 0.34 ± 0.09 | 0.19 ± 0.11 | 0.14 ± 0.06 | 0.13 ± 0.04 | not conducted |

TABLE 5

A ratio of inflammation/muscle of Tc-99m labeled
peptide on rabbit infectious disease model
(n = 3, Tc-99m-peptide 3: n = 5, mean ± standard deviation)

| Labeled compound | Elapse of time after administration | | | | | | |
|---|---|---|---|---|---|---|---|
| | 5 min. | 1 hr | 2 hrs | 3 hrs | 4 hrs | 5 hrs | 22 hrs |
| Tc-99m-peptide 3 | 1.64 ± 0.57 | 3.56 ± 1.03 | 6.55 ± 2.06 | 8.68 ± 2.89 | 11.48 ± 2.88 | 13.11 ± 3.37 | 54.16 ± 32.86 |
| Tc-99m-peptide 4 | 1.94 ± 0.49 | 4.08 ± 1.34 | 6.75 ± 2.71 | 10.65 ± 5.53 | 13.02 ± 5.76 | 14.81 ± 6.77 | 29.07 ± 19.97 |
| Tc-99m-peptide 6 | 2.08 ± 0.46 | 6.16 ± 0.59 | 14.25 ± 0.31 | 24.31 ± 4.55 | 30.20 ± 7.49 | 29.67 ± 7.66 | 43.84 ± 12.58 |
| Tc-99m-peptide 8 | 1.31 ± 0.56 | 4.27 ± 2.15 | 9.22 ± 3.81 | 13.33 ± 5.30 | 18.51 ± 1.88 | 19.30 ± 2.18 | not conducted |
| Tc-99m-peptide 9 | 1.83 ± 0.38 | 3.91 ± 0.52 | 5.30 ± 2.08 | 5.79 ± 1.48 | 8.87 ± 3.02 | 8.84 ± 3.03 | not conducted |
| Tc-99m-peptide 12 | 2.96 ± 0.63 | 7.06 ± 1.43 | 10.34 ± 3.34 | 13.81 ± 2.94 | 16.88 ± 2.80 | 19.64 ± 1.24 | 33.94 ± 20.76 |
| Tc-99m-peptide 13 | 1.60 ± 0.22 | 2.84 ± 0.46 | 6.21 ± 1.25 | 5.60 ± 2.00 | 9.25 ± 1.63 | 11.26 ± 2.77 | not conducted |
| Tc-99m-peptide 14 | 1.63 ± 0.21 | 3.88 ± 0.88 | 12.23 ± 3.30 | 11.20 ± 3.73 | 18.93 ± 3.08 | 27.79 ± 9.32 | not conducted |
| Tc-99m-peptide 15 | 2.41 ± 0.09 | 5.94 ± 1.82 | 8.84 ± 4.41 | 11.86 ± 6.02 | 12.88 ± 9.40 | 13.32 ± 8.76 | not conducted |
| Tc-99m-peptide 16 | 2.10 ± 0.31 | 2.67 ± 0.49 | 4.02 ± 1.27 | 5.52 ± 0.13 | 4.14 ± 0.83 | 4.56 ± 0.53 | not conducted |
| Tc-99m-peptide 17 | 2.02 ± 0.36 | 3.16 ± 0.97 | 4.63 ± 1.90 | 7.29 ± 4.74 | 7.80 ± 6.33 | 10.71 ± 0.32 | not conducted |
| Tc-99m-peptide 18 | 1.58 ± 0.01 | 2.21 ± 0.98 | 3.76 ± 0.11 | 3.60 ± 2.71 | 4.18 ± 3.09 | 4.20 ± 2.67 | not conducted |

Example 5

Pharmakokinetics of Tc-99m Labeled Peptide 3, Peptide 4, Peptide 6 and Peptide 12

(1) Method

Biodistributions of four types of Tc-99m labeled compounds consisting of Tc-99m-peptide 3, Tc-99m-peptide 4, Tc-99m-peptide 6 and Tc-99m-peptide 12 obtained in Example 2 were examined in normal rats. The Biodistribution experiments were conducted according to the conventional method for the person skilled in the art. A sample, 3.0–3.7 MBq each, was administered to the tail vein of non-fasting SD (Sprague-Dawley) strain rats (body weight 140–200 g) under anesthesia with ravonal. After 5 minutes, 30 minutes, 60 minutes and 180 minutes from the administration, rats were exsanguinated from the abdominal aorta. Radioactive counts of each extirpated organ to injection dose were measured with a NaI single channel analyzer. Weight of each organ was measured for calculation of the biodistribution. A ratio of the radioactivity of each organ to injection dose was shown by a value per organ (% ID/organ) or a value per gram of organ (% ID/g organ).

(2) Results

Results are shown in Table 6, Table 7, Table 8 and Table 9. Time course changes in urine and the small intestine are shown in FIG. 16 and FIG. 17 from the results of Table 6, Table 7, Table 8 and Table 9.

Figure 16:
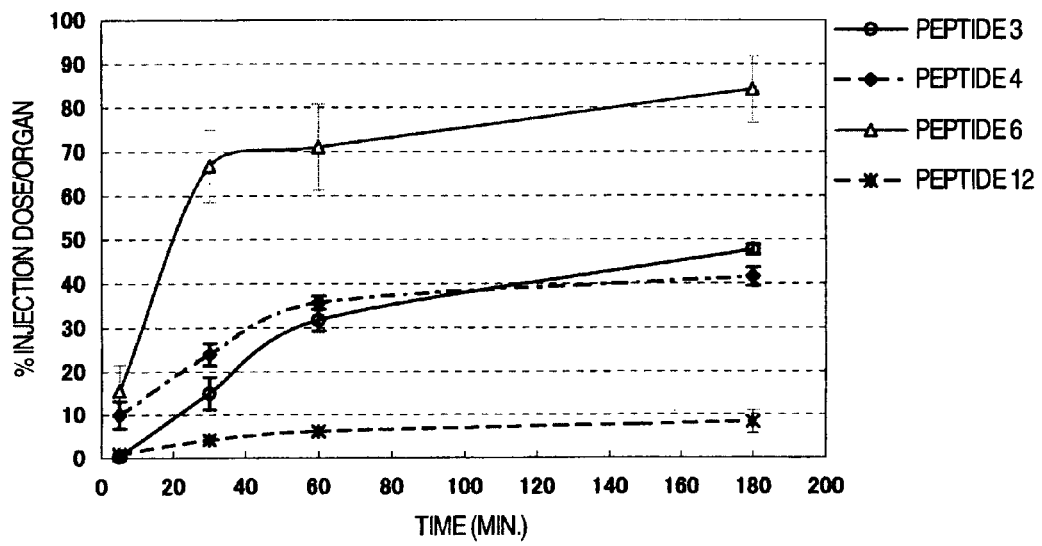
FIG. 16 shows a time course change of urinary excretion of Tc-99m-peptides in a normal rat.
Figure 17:
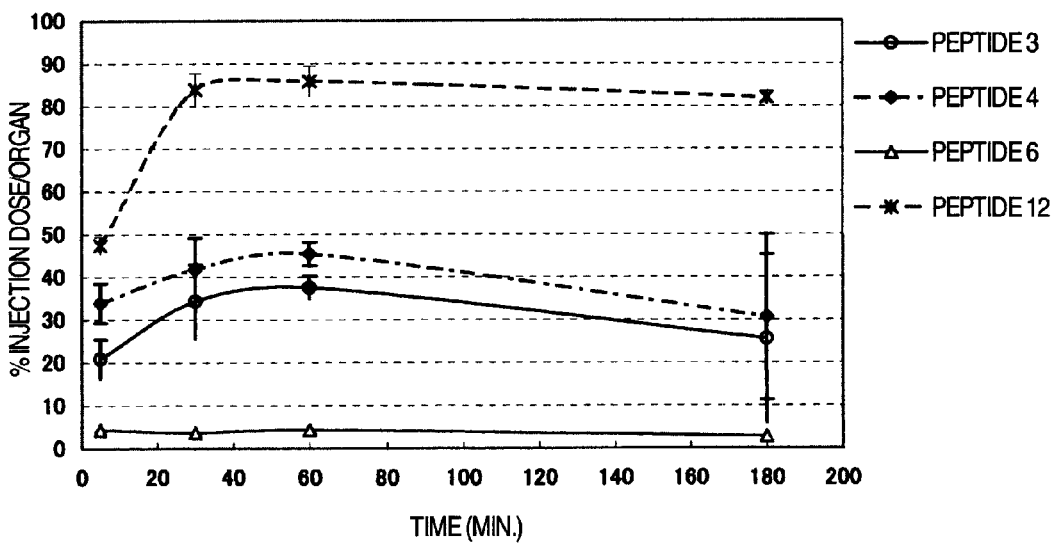
FIG. 17 shows a time course change of accumulation of Tc-99m-peptides in the small intestine of a normal rat.

According to the results shown in Table 6, Table 7, Table 8, Table 9, FIG. 16 and FIG. 17, it was found that the biodistributions of Tc-99m labeled peptides in normal rats were greatly different from each other depending on the amino acid residues of Z and W of the formula described in claim 1. Namely, a metabolic pathway of the conventional Tc-99m-peptide 12 might be mainly through the hepatobiliary excretion route, because of high accumulation in the liver after 5 minutes from the administration, high accumulation in the stomach at each time point as compared with other peptides, high accumulation at each time point in the small intestine, and high accumulation at 180 minutes from the intestine to the appendix (FIG. 17). Further, it is difficult to visualize abdominal inflammation such as inflammatory bowel disease because of high accumulation in the small intestine.

Contrary to that, among the peptides of the present invention, Tc-99m labeled compounds of peptide 3, peptide 4 and peptide 6, in which T and U of the formula described in claim 1 were converted to or added with a hydrophilic amino acid such as a charged amino acid and an acidic amino acid, were different from the biodistribution of Tc-99m-peptide 12 and were stimulated for excretion to urine (FIG. 16). In particular, the tendency was significant for Tc-99m-peptide 6. This characteristic is quite important for visualization of abdominal inflammation such as inflammatory bowel disease. Consequently, the peptides of the present invention were suggested to be effective for observing the region with abdominal leukocyte infiltration due to low distribution in the abdominal region particularly in the small intestine as compared with the conventionally known peptide 12.

TABLE 6

Biodistribution of Tc-99m-peptide 3 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Blood | 5.345 ± 0.824 | 1.759 ± 0.769 | 0.657 ± 0.150 | 0.318 ± 0.225 |
|  | (0.719 ± 0.067) | (0.212 ± 0.073) | (0.082 ± 0.008) | (0.038 ± 0.025) |
| Heart | 0.182 ± 0.014 | 0.054 ± 0.012 | 0.020 ± 0.003 | 0.004 ± 0.000 |
|  | (0.315 ± 0.014) | (0.094 ± 0.024) | (0.034 ± 0.002) | (0.007 ± 0.000) |
| Lungs | 0.805 ± 0.150 | 0.395 ± 0.186 | 0.117 ± 0.011 | 0.040 ± 0.005 |
|  | (0.868 ± 0.116) | (0.383 ± 0.155) | (0.128 ± 0.010) | (0.045 ± 0.007) |
| Liver | 21.912 ± 0.529 | 16.435 ± 3.821 | 7.339 ± 0.595 | 1.239 ± 0.132 |
|  | (3.287 ± 0.215) | (2.475 ± 0.543) | (1.105 ± 0.089) | (0.206 ± 0.026) |
| Spleen | 0.169 ± 0.012 | 0.102 ± 0.003 | 0.065 ± 0.013 | 0.042 ± 0.004 |
|  | (0.471 ± 0.022) | (0.239 ± 0.020) | (0.155 ± 0.026) | (0.102 ± 0.014) |
| Kidneys | 15.350 ± 1.803 | 19.142 ± 1.543 | 14.223 ± 1.091 | 6.016 ± 1.089 |
|  | (11.297 ± 1.970) | (13.953 ± 2.124) | (10.679 ± 0.785) | (4.508 ± 1.013) |
| Stomach | 0.500 ± 0.060 | 0.354 ± 0.196 | 0.160 ± 0.177 | 0.058 ± 0.049 |
|  | (0.131 ± 0.031) | (0.090 ± 0.037) | (0.044 ± 0.043) | (0.018 ± 0.012) |
| Small intestine | 21.307 ± 1.479 | 33.762 ± 5.276 | 37.742 ± 2.889 | 40.273 ± 1.263 |
|  | (2.691 ± 0.329) | (4.504 ± 0.939) | (5.165 ± 0.506) | (5.787 ± 0.208) |
| Appendix | 0.431 ± 0.048 | 0.125 ± 0.035 | 0.057 ± 0.013 | 1.636 ± 0.993 |
|  | (0.086 ± 0.010) | (0.024 ± 0.008) | (0.013 ± 0.004) | (0.308 ± 0.171) |
| Colon | 0.131 ± 0.052 | 0.050 ± 0.024 | 0.017 ± 0.006 | 0.022 ± 0.026 |
|  | (0.335 ± 0.030) | (0.117 ± 0.016) | (0.040 ± 0.001) | (0.049 ± 0.060) |
| Rectum | 0.486 ± 0.059 | 0.164 ± 0.010 | 0.063 ± 0.005 | 0.050 ± 0.020 |
|  | (0.465 ± 0.042) | (0.176 ± 0.053) | (0.062 ± 0.004) | (0.051 ± 0.018) |
| Adrenal | 0.024 ± 0.005 | 0.008 ± 0.001 | 0.004 ± 0.002 | 0.001 ± 0.000 |
|  | (0.605 ± 0.131) | (0.194 ± 0.024) | (0.095 ± 0.043) | (0.001 ± 0.000) |
| Ovaries | 0.059 ± 0.003 | 0.020 ± 0.003 | 0.008 ± 0.002 | 0.001 ± 0.002 |
|  | (0.735 ± 0.034) | (0.255 ± 0.034) | (0.106 ± 0.019) | (0.013 ± 0.022) |
| Bones of lower limb | 0.408 ± 0.042 | 0.165 ± 0.035 | 0.073 ± 0.008 | 0.035 ± 0.006 |
|  | (0.332 ± 0.035) | (0.139 ± 0.030) | (0.060 ± 0.009) | (0.029 ± 0.006) |
| Skin | 1.033 ± 0.405 | 0.362 ± 0.067 | 0.114 ± 0.037 | 0.026 ± 0.010 |
|  | (0.371 ± 0.019) | (0.154 ± 0.046) | (0.052 ± 0.004) | (0.011 ± 0.001) |
| Muscle | 1.115 ± 0.236 | 0.366 ± 0.115 | 0.110 ± 0.021 | 0.026 ± 0.006 |
|  | (0.146 ± 0.018) | (0.047 ± 0.013) | (0.016 ± 0.002) | (0.004 ± 0.001) |
| Urine | 0.230 ± 0.126 | 15.575 ± 3.638 | 34.936 ± 2.443 | 48.414 ± 2.048 |
| Feces | 0.025 ± 0.013 | 0.014 ± 0.009 | 0.012 ± 0.013 | 0.618 ± 1.032 |
| Carcas | 30.489 ± 1.877 | 11.147 ± 2.812 | 4.283 ± 0.300 | 1.183 ± 0.362 |
|  | (0.265 ± 0.011) | (0.099 ± 0.027) | (0.037 ± 0.002) | (0.010 ± 0.003) |

TABLE 7

Biodistribution of Tc-99m-peptide 4 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Blood | 6.189 ± 1.270 | 1.922 ± 0.560 | 0.823 ± 0.350 | 0.126 ± 0.021 |
|  | (0.846 ± 0.167) | (0.252 ± 0.022) | (0.109 ± 0.031) | (0.017 ± 0.003) |
| Heart | 0.163 ± 0.036 | 0.043 ± 0.006 | 0.026 ± 0.013 | 0.004 ± 0.001 |
|  | (0.306 ± 0.077) | (0.086 ± 0.010) | (0.039 ± 0.010) | (0.007 ± 0.001) |
| Lungs | 0.652 ± 0.096 | 0.243 ± 0.027 | 0.147 ± 0.016 | 0.068 ± 0.017 |
|  | (0.726 ± 0.107) | (0.279 ± 0.057) | (0.160 ± 0.021) | (0.075 ± 0.023) |
| Liver | 18.159 ± 2.621 | 11.820 ± 1.257 | 6.583 ± 0.266 | 1.358 ± 0.284 |
|  | (2.810 ± 0.295) | (1.889 ± 0.186) | (1.032 ± 0.061) | (0.232 ± 0.065) |
| Spleen | 0.144 ± 0.010 | 0.110 ± 0.014 | 0.076 ± 0.015 | 0.059 ± 0.009 |
|  | (0.367 ± 0.064) | (0.275 ± 0.032) | (0.192 ± 0.031) | (0.160 ± 0.027) |
| Kidneys | 5.643 ± 2.131 | 4.671 ± 0.594 | 3.938 ± 0.323 | 3.433 ± 1.054 |
|  | (4.354 ± 1.312) | (3.806 ± 0.604) | (3.365 ± 0.433) | (2.814 ± 0.926) |
| Stomach | 4.484 ± 4.613 | 0.340 ± 0.145 | 0.391 ± 0.293 | 0.178 ± 0.092 |
|  | (0.905 ± 0.747) | (0.115 ± 0.042) | (0.118 ± 0.085) | (0.050 ± 0.025) |
| Small intestine | 28.887 ± 3.569 | 41.173 ± 0.337 | 44.035 ± 4.359 | 13.553 ± 1.591 |
|  | (3.862 ± 0.976) | (5.648 ± 0.657) | (5.876 ± 0.659) | (1.997 ± 0.239) |
| Appendix | 0.358 ± 0.029 | 0.116 ± 0.011 | 0.077 ± 0.032 | 36.011 ± 2.291 |
|  | (0.089 ± 0.019) | (0.029 ± 0.003) | (0.018 ± 0.004) | (6.306 ± 0.610) |
| Colon | 0.244 ± 0.120 | 0.072 ± 0.024 | 0.032 ± 0.016 | 0.115 ± 0.014 |
|  | (0.395 ± 0.046) | (0.172 ± 0.089) | (0.071 ± 0.031) | (0.289 ± 0.115) |
| Rectum | 0.476 ± 0.241 | 0.125 ± 0.004 | 0.083 ± 0.037 | 0.060 ± 0.022 |
|  | (0.565 ± 0.124) | (0.166 ± 0.019) | (0.100 ± 0.057) | (0.061 ± 0.013) |
| Adrenal | 0.024 ± 0.003 | 0.010 ± 0.001 | 0.004 ± 0.001 | 0.001 ± 0.001 |
|  | (0.604 ± 0.253) | (0.242 ± 0.067) | (0.092 ± 0.009) | (0.037 ± 0.014) |

TABLE 7-continued

Biodistribution of Tc-99m-peptide 4 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Ovaries | 0.069 ± 0.026 | 0.016 ± 0.005 | 0.008 ± 0.001 | 0.003 ± 0.001 |
|  | (0.861 ± 0.327) | (0.204 ± 0.062) | (0.101 ± 0.011) | (0.035 ± 0.017) |
| Bones of | 0.342 ± 0.017 | 0.167 ± 0.020 | 0.0160 ± 0.026 | 0.044 ± 0.015 |
| lower limb | (0.304 ± 0.019) | (0.150 ± 0.022) | (0.095 ± 0.002) | (0.039 ± 0.012) |
| Skin | 0.506 ± 0.217 | 0.414 ± 0.189 | 0.099 ± 0.017 | 0.022 ± 0.006 |
|  | (0.321 ± 0.039) | (0.168 ± 0.016) | (0.062 ± 0.018) | (0.015 ± 0.001) |
| Muscle | 0.850 ± 0.112 | 0.296 ± 0.060 | 0.115 ± 0.037 | 0.023 ± 0.003 |
|  | (0.132 ± 0.014) | (0.054 ± 0.016) | (0.019 ± 0.006) | (0.004 ± 0.000) |
| Urine | 5.258 ± 2.993 | 26.706 ± 0.900 | 37.798 ± 2.759 | 42.009 ± 0.925 |
| Feces | 0.027 ± 0.002 | 0.095 ± 0.101 | 0.097 ± 0.079 | 1.485 ± 2.389 |
| Carcas | 27.525 ± 2.159 | 11.661 ± 0.196 | 5.563 ± 1.766 | 1.448 ± 0.256 |
|  | (0.260 ± 0.042) | (0.111 ± 0.008) | (0.052 ± 0.017) | (0.014 ± 0.002) |

TABLE 8

Biodistribution of Tc-99m-peptide 6 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Blood | 11.205 ± 0.809 | 3.657 ± 1.074 | 0.936 ± 0.364 | 0.532 ± 0.421 |
|  | (1.414 ± 0.176) | (0.451 ± 0.052) | (0.123 ± 0.020) | (0.062 ± 0.044) |
| Heart | 0.275 ± 0.050 | 0.097 ± 0.026 | 0.029 ± 0.008 | 0.014 ± 0.006 |
|  | (0.494 ± 0.083) | (0.161 ± 0.029) | (0.056 ± 0.017) | (0.024 ± 0.009) |
| Lungs | 1.770 ± 0.274 | 0.715 ± 0.037 | 0.369 ± 0.029 | 0.159 ± 0.023 |
|  | (1.770 ± 0.263) | (0.752 ± 0.062) | (0.390 ± 0.054) | (0.167 ± 0.017) |
| Liver | 6.374 ± 0.900 | 4.097 ± 0.758 | 2.713 ± 0.379 | 2.167 ± 0.369 |
|  | (1.003 ± 0.162) | (0.607 ± 0.113) | (0.465 ± 0.072) | (0.353 ± 0.042) |
| Spleen | 0.229 ± 0.050 | 0.140 ± 0.040 | 0.105 ± 0.028 | 0.090 ± 0.014 |
|  | (0.548 ± 0.092) | (0.198 ± 0.083) | (0.284 ± 0.054) | (0.210 ± 0.011) |
| Kidneys | 10.176 ± 2.359 | 5.916 ± 2.411 | 3.867 ± 1.501 | 2.634 ± 1.172 |
|  | (7.546 ± 1.996) | (3.971 ± 1.559) | (2.975 ± 1.020) | (1.838 ± 0.732) |
| Stomach | 0.658 ± 0.196 | 0.443 ± 0.204 | 0.166 ± 0.037 | 0.104 ± 0.067 |
|  | (0.297 ± 0.022) | (0.166 ± 0.090) | (0.049 ± 0.003) | (0.028 ± 0.011) |
| Small | 3.680 ± 0.549 | 3.385 ± 0.898 | 3.858 ± 0.753 | 0.996 ± 0.574 |
| intestine | (0.592 ± 0.073) | (0.472 ± 0.117) | (0.596 ± 0.120) | (0.163 ± 0.099) |
| Appendix | 0.662 ± 0.009 | 0.237 ± 0.039 | 0.097 ± 0.009 | 2.202 ± 0.468 |
|  | (0.165 ± 0.020) | (0.049 ± 0.007) | (0.022 ± 0.008) | (0.396 ± 0.115) |
| Colon | 0.311 ± 0.110 | 0.140 ± 0.087 | 0.047 ± 0.009 | 0.031 ± 0.021 |
|  | (0.625 ± 0.094) | (0.223 ± 0.057) | (0.094 ± 0.010) | (0.069 ± 0.037) |
| Rectum | 0.895 ± 0.245 | 0.424 ± 0.151 | 0.260 ± 0.130 | 0.051 ± 0.010 |
|  | (0.913 ± 0.169) | (0.503 ± 0.372) | (0.329 ± 0.245) | (0.052 ± 0.009) |
| Adrenal | 0.027 ± 0.003 | 0.011 ± 0.001 | 0.005 ± 0.001 | 0.002 ± 0.001 |
|  | (0.668 ± 0.077) | (0.276 ± 0.033) | (0.117 ± 0.029) | (0.061 ± 0.035) |
| Ovaries | 0.096 ± 0.004 | 0.044 ± 0.003 | 0.020 ± 0.003 | 0.013 ± 0.009 |
|  | (1.195 ± 0.048) | (0.546 ± 0.040) | (0.251 ± 0.044) | (0.160 ± 0.117) |
| Bones of | 0.578 ± 0.044 | 0.264 ± 0.014 | 0.122 ± 0.030 | 0.067 ± 0.008 |
| lower limb | (0.489 ± 0.065) | (0.221 ± 0.014) | (0.101 ± 0.023) | (0.053 ± 0.005) |
| Skin | 1.756 ± 0.161 | 0.640 ± 0.214 | 0.238 ± 0.051 | 0.044 ± 0.014 |
|  | (0.652 ± 0.069) | (0.273 ± 0.008) | (0.088 ± 0.011) | (0.024 ± 0.006) |
| Muscle | 1.632 ± 0.201 | 0.688 ± 0.279 | 0.180 ± 0.036 | 0.066 ± 0.009 |
|  | (0.236 ± 0.021) | (0.094 ± 0.026) | (0.027 ± 0.004) | (0.009 ± 0.000) |
| Urine | 7.770 ± 2.348 | 56.342 ± 5.430 | 78.567 ± 2.774 | 87.408 ± 1.020 |
| Feces | 0.048 ± 0.016 | 0.056 ± 0.033 | 0.025 ± 0.011 | 0.646 ± 0.636 |
| Carcas | 51.858 ± 1.751 | 22.704 ± 3.734 | 8.397 ± 1.185 | 2.772 ± 0.661 |
|  | (0.465 ± 0.026) | (0.199 ± 0.024) | (0.079 ± 0.014) | (0.025 ± 0.007) |

TABLE 9

Biodistribution of Tc-99m-peptide 12 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Blood | 4.615 ± 0.611 | 0.880 ± 0.059 | 0.613 ± 0.185 | 0.332 ± 0.205 |
|  | (0.683 ± 0.074) | (0.146 ± 0.019) | (0.112 ± 0.038) | (0.054 ± 0.035) |

TABLE 9-continued

Biodistribution of Tc-99m-peptide 12 in normal rats
Upper column: % ID/organ; Lower column: % ID/g
(n = 3, mean ± standard deviation)

| Organs | 5 min. | 30 min. | 60 min. | 180 min. |
|---|---|---|---|---|
| Heart | 0.110 ± 0.016 | 0.021 ± 0.004 | 0.016 ± 0.006 | 0.009 ± 0.007 |
| | (0.205 ± 0.030) | (0.040 ± 0.008) | (0.031 ± 0.009) | (0.018 ± 0.014) |
| Lungs | 0.221 ± 0.021 | 0.065 ± 0.008 | 0.052 ± 0.011 | 0.030 ± 0.019 |
| | (0.259 ± 0.013) | (0.073 ± 0.005) | (0.061 ± 0.012) | (0.036 ± 0.025) |
| Liver | 32.141 ± 1.082 | 1.527 ± 0.301 | 0.696 ± 0.083 | 0.320 ± 0.221 |
| | (4.547 ± 0.226) | (0.235 ± 0.028) | (0.107 ± 0.019) | (0.054 ± 0.036) |
| Spleen | 0.055 ± 0.005 | 0.019 ± 0.003 | 0.014 ± 0.002 | 0.013 ± 0.010 |
| | (0.135 ± 0.013) | (0.046 ± 0.008) | (0.039 ± 0.003) | (0.035 ± 0.023) |
| Kidneys | 1.380 ± 0.161 | 1.080 ± 0.125 | 1.043 ± 0.167 | 1.017 ± 0.639 |
| | (1.055 ± 0.152) | (0.876 ± 0.145) | (0.830 ± 0.123) | (0.822 ± 0.525) |
| Stomach | 0.802 ± 0.643 | 1.884 ± 1.594 | 1.748 ± 0.191 | 1.953 ± 1.069 |
| | (0.219 ± 0.167) | (0.516 ± 0.446) | (0.586 ± 0.076) | (0.596 ± 0.178) |
| Small intestine | 44.145 ± 2.931 | 86.860 ± 2.200 | 86.308 ± 1.540 | 11.574 ± 15.140 |
| | (5.915 ± 0.448) | (12.285 ± 0.316) | (12.392 ± 0.927) | (1.888 ± 2.411) |
| Appendix | 0.161 ± 0.22 | 0.076 ± 0.003 | 0.169 ± 0.047 | 73.702 ± 24.073 |
| | (0.043 ± 0.004) | (0.020 ± 0.002) | (0.043 ± 0.007) | (15.226 ± 6.088) |
| Colon | 0.080 ± 0.006 | 0.023 ± 0.005 | 0.026 ± 0.009 | 0.048 ± 0.016 |
| | (0.167 ± 0.007) | (0.048 ± 0.006) | (0.046 ± 0.011) | (0.112 ± 0.052) |
| Rectum | 0.162 ± 0.038 | 0.041 ± 0.011 | 0.037 ± 0.010 | 0.019 ± 0.011 |
| | (0.175 ± 0.003) | (0.053 ± 0.005) | (0.045 ± 0.011) | (0.022 ± 0.016) |
| Adrenal | 0.009 ± 0.001 | 0.002 ± 0.000 | 0.002 ± 0.000 | 0.001 ± 0.001 |
| | (0.223 ± 0.031) | (0.057 ± 0.009) | (0.054 ± 0.011) | (0.235 ± 0.032) |
| Ovaries | 0.29 ± 0.008 | 0.008 ± 0.001 | 0.007 ± 0.001 | 0.008 ± 0.001 |
| | (0.368 ± 0.100) | (0.098 ± 0.015) | (0.088 ± 0.014) | (0.038 ± 0.016) |
| Bones of lower limb | 0.165 ± 0.026 | 0.057 ± 0.005 | 0.049 ± 0.006 | 0.029 ± 0.021 |
| | (0.140 ± 0.016) | (0.050 ± 0.005) | (0.043 ± 0.008) | (0.025 ± 0.017) |
| Skin | 0.374 ± 0.040 | 0.091 ± 0.016 | 0.104 ± 0.025 | 0.042 ± 0.047 |
| | (0.165 ± 0.027) | (0.073 ± 0.008) | (0.036 ± 0.002) | (0.0018 ± 0.019) |
| Muscle | 0.374 ± 0.040 | 0.137 ± 0.031 | 0.105 ± 0.027 | 0.047 ± 0.023 |
| | (0.165 ± 0.027) | (0.021 ± 0.004) | (0.016 ± 0.004) | (0.007 ± 0.004) |
| Urine | 0.400 ± 0.154 | 2.687 ± 0.285 | 5.493 ± 0.833 | 8.767 ± 5.591 |
| Feces | 0.025 ± 0.002 | 0.049 ± 0.005 | 0.105 ± 0.019 | 0.373 ± 0.122 |
| Carcas | 14.537 ± 1.466 | 4.493 ± 0.616 | 3.411 ± 0.465 | 1.720 ± 1.276 |
| | (0.134 ± 0.015) | (0.041 ± 0.006) | (0.031 ± 0.004) | (0.016 ± 0.012) |

Example 6

Biodistribution in Rat Ulcerative Colitis Model and Usefulness on Chronic Inflammation (1) Method Preparation of inflammation model: Rat ulcerative colitis model was prepared according to the method of Anthony et al. (Anthony et al. Int. J. Exp. Path., 76, 215–224, 1995). 2,4,6-Trinitrobenzenesulfonic acid (TNBS) 360 mg was dissolved in ultra pure water 4 ml, and ethanol 3.2 ml was added therein to prepare 50.0 mg/ml 46% ethanol/physiological saline solution. A tube was inserted per anum in 7–8 cm depth into the intestine of etherized SD strain rats (Sprague Dawley, specific pathogen free), female, 7 weeks old, body weight 164–177 g, fasted 24 hours before, and air 0.1 ml was infused. Subsequently, TNBS/46% ethanol/physiological saline 0.2 ml was infused, and massaged and tilted the posture for 2 minutes. After 5 days, the rats were used for the examination.

Tc-99m-peptide 3, Tc-99m-peptide 4, Tc-99m-peptide 6 and prior known conventional Tc-99m-peptide 12 as a control, about 7.4 MBq/rat each, were administered to the tail vein. After 5 minutes, 30 minutes, 60 minutes and 180 minutes from the administration, rats were exsanguinated and a radioactive distribution in each organ was measured by using a NaI single channel analyzer to obtain % ID/each organ and % ID/g organ. The rectum with inflammation region was set as the inflammation region, and ratios of [rectum (inflammation)]/[muscle] (ratios of [A]/[M]) and ratios of [rectum (inflammation)]/[blood] (ratios of [A]/[B]) were obtained based on the values of % ID/g organ.

(2) Results

Results are shown in Table 10, Table 11, Table 12 and Table 13.

Tc-99m-peptide 3 showed the ratios of [A]/[M] 3.36±0.58 after 5 minutes from the administration, and 7.91±1.16 after 180 minutes from the administration. High level of radioactivity was exhibited in the inflammation region as compared with the muscle with non-inflammation region as well as increasing tendency of the ratio of [A]/[M] with the time course dependent manner. Further, on and after 60 minutes from the administration, the ratio of [A]/[B] exceeded a value 1, and exhibited 2.00±1.50 after 180 minutes from the administration, showing increasing tendency. This may not be due to a non-specific accumulation reflecting increased blood flow but is considered to be due to a specific accumulation to inflammation.

Tc-99m-peptide 4 showed the ratios of [A]/[M] 4.37±0.68 after 5 minutes from the administration, and 9.29±2.82 after 180 minutes from the administration. High level of radioactivity was exhibited in the inflammation region as compared with the muscle with non-inflammation region as well as increasing tendency of the ratio of [A]/[M] with the time course dependent manner. Further, on and after 60 minutes from the administration, the ratio of [A]/[B] exceeded a value 1, and exhibited 1.51±0.41 after 180 minutes from the administration, showing increasing tendency. This may not be due to a non-specific accumulation reflecting increased blood flow but is considered to be due to a specific accumulation to inflammation.

Tc-99m-peptide 6 showed the ratios of [A]/[M] 4.41±0.97 after 5 minutes from the administration, and 16.50±11.08 after 180 minutes from the administration. High level of radioactivity was exhibited in the inflammation region as compared with the muscle with non-inflammation region as well as increasing tendency of the ratio of [A]/[M] with the time course dependent manner. Further, on and after 30 minutes from the administration, the ratio of [A]/[B] exceeded a value 1, and exhibited 2.74±1.72 after 180 minutes from the administration, showing increasing tendency. This may not be due to a non-specific accumulation reflecting increased blood flow but is considered to be due to a specific accumulation to inflammation.

Tc-99m-peptide 12 showed the ratios of [A]/[M] 4.66±3.13 after 5 minutes from the administration, and 6.22±4.61 after 180 minutes from the administration. This showed a low ratio of [A]/[M] as compared with peptides of the present invention.

Although the ratio of [A]/[M] showed maximum value, 11.10±12.33, after 60 minutes from the administration, it decreased thereafter. Although the ratio of [A]/[B] showed 1.89±2.39 after 60 minutes from the administration, it decreased thereafter, and was 1.00±0.89 after 180 minutes from the administration.

According to the present examination, the peptides of the present invention were superior on the points of the accumulation and the retentivity to chronic inflammatory region with high infiltration of lymphocytes and monocytes than the prior known peptide 12, and were proved to be useful for chronic inflammation such as ulcerative colitis.

TABLE 10

Biodistribution of Tc-99m-peptide 3 in rat IBD model
Upper column: % ID/organ; Lower column: % ID/g
(n = 3, mean ± standard deviation)

| Organs | 5 min. | 30 min. | 60 min. | 180 min. |
|---|---|---|---|---|
| Blood | 6.145 ± 1.475 | 2.397 ± 1.066 | 0.763 ± 0.238 | 0.164 ± 0.120 |
|  | (0.912 ± 0.084) | (0.341 ± 0.097) | (0.108 ± 0.025) | (0.023 ± 0.013) |
| Heart | 0.0167 ± 0.004 | 0.045 ± 0.006 | 0.020 ± 0.001 | 0.004 ± 0.000 |
|  | (0.345 ± 0.006) | (0.101 ± 0.009) | (0.042 ± 0.004) | (0.008 ± 0.001) |
| Lungs | 0.840 ± 0.027 | 0.248 ± 0.004 | 0.151 ± 0.020 | 0.053 ± 0.016 |
|  | (1.031 ± 0.058) | (0.308 ± 0.016) | (0.177 ± 0.029) | (0.068 ± 0.025) |
| Liver | 24.382 ± 2.015 | 16.240 ± 2.633 | 7.993 ± 1.993 | 1.249 ± 0.250 |
|  | (4.146 ± 0.528) | (2.872 ± 0.793) | (1.310 ± 0.313) | (0.234 ± 0.053) |
| Spleen | 0.211 ± 0.008 | 0.075 ± 0.023 | 0.074 ± 0.018 | 0.053 ± 0.016 |
|  | (0.597 ± 0.046) | (0.212 ± 0.070) | (0.207 ± 0.037) | (0.136 ± 0.043) |
| Kidneys | 13.030 ± 1.588 | 18.869 ± 6.719 | 16.068 ± 1.238 | 6.248 ± 0.746 |
|  | (11.263 ± 1.648) | (15.816 ± 5.386) | (13.353 ± 1.426) | (5.333 ± 0.482) |
| Stomach | 1.428 ± 0.982 | 0.181 ± 0.072 | 0.082 ± 0.013 | 0.035 ± 0.016 |
|  | (0.402 ± 0.242) | (0.058 ± 0.034) | (0.025 ± 0.005) | (0.013 ± 0.006) |
| Small intestine | 20.876 ± 4.511 | 34.286 ± 8.601 | 37.506 ± 2.672 | 25.538 ± 19.634 |
|  | (3.056 ± 0.970) | (5.520 ± 2.262) | (5.249 ± 0.446) | (4.165 ± 3.176) |
| Appendix | 0.405 ± 0.085 | 0.192 ± 0.134 | 0.080 ± 0.024 | 14.113 ± 13.789 |
|  | (0.110 ± 0.031) | (0.030 ± 0.003) | (0.015 ± 0.004) | (3.030 ± 2.871) |
| Colon | 0.228 ± 0.044 | 0.052 ± 0.033 | 0.046 ± 0.026 | 0.087 ± 0.110 |
|  | (0.484 ± 0.028) | (0.140 ± 0.012) | (0.083 ± 0.044) | (0.229 ± 0.315) |
| Rectum (inflammation) | 0.590 ± 0.118 | 0.286 ± 0.210 | 0.110 ± 0.062 | 0.089 ± 0.024 |
|  | (0.573 ± 0.047) | (0.203 ± 0.036) | (0.097 ± 0.035) | (0.041 ± 0.021) |
| Adrenal | 0.026 ± 0.003 | 0.008 ± 0.001 | 0.003 ± 0.001 | 0.001 ± 0.001 |
|  | (0.294 ± 0.360) | (0.097 ± 0.065) | (0.067 ± 0.019) | (0.082 ± 0.084) |
| Ovaries | 0.062 ± 0.046 | 0.011 ± 0.000 | 0.005 ± 0.002 | 0.005 ± 0.005 |
|  | (0.779 ± 0.572) | (0.135 ± 0.003) | (0.069 ± 0.020) | (0.069 ± 0.057) |
| Bones of lower limb | 0.225 ± 0.047 | 0.087 ± 0.019 | 0.049 ± 0.018 | 0.035 ± 0.022 |
|  | (0.211 ± 0.047) | (0.086 ± 0.032) | (0.050 ± 0.023) | (0.036 ± 0.023) |
| Skin | 0.378 ± 0.114 | 0.191 ± 0.211 | 0.103 ± 0.018 | 0.069 ± 0.047 |
|  | (0.220 ± 0.017) | (0.102 ± 0.049) | (0.062 ± 0.041) | (0.040 ± 0.034) |
| Muscle | 0.537 ± 0.180 | 0.181 ± 0.101 | 0.094 ± 0.014 | 0.068 ± 0.049 |
|  | (0.104 ± 0.008) | (0.032 ± 0.015) | (0.018 ± 0.009) | (0.014 ± 0.012) |
| Urine | 0.681 ± 0.234 | 4.094 ± 0.769 | 6.071 ± 0.796 | 8.305 ± 2.667 |
| Feces | 0.656 ± 1.023 | 0.073 ± 0.031 | 0.073 ± 0.002 | 0.430 ± 0.391 |
| Carcas | 16.159 ± 2.511 | 5.820 ± 1.595 | 3.392 ± 1.387 | 2.661 ± 2.059 |
|  | (0.197 ± 0.056) | (0.065 ± 0.027) | (0.040 ± 0.024) | (0.036 ± 0.035) |
| Rectum (inflammation)/ blood | 0.64 ± 0.04 | 0.63 ± 0.10 | 1.09 ± 0.70 | 2.00 ± 1.50 |
| Rectum (inflammation)/ muscle | 3.36 ± 0.58 | 4.00 ± 0.95 | 4.78 ± 1.57 | 7.91 ± 1.16 |

TABLE 11

Biodistribution of Tc-99m-peptide 4 in rat IBD model
Upper column: % ID/organ; Lower column: % ID/g
(n = 3, mean ± standard deviation)

| Organs | 5 min. | 30 min. | 60 min. | 180 min. |
|---|---|---|---|---|
| Blood | 5.232 ± 1.667 | 1.764 ± 0.087 | 0.821 ± 0.308 | 0.146 ± 0.029 |
|  | (0.625 ± 0.114) | (0.213 ± 0.055) | (0.092 ± 0.016) | (0.019 ± 0.002) |

TABLE 11-continued

Biodistribution of Tc-99m-peptide 4 in rat IBD model
Upper column: % ID/organ; Lower column: % ID/g
(n = 3, mean ± standard deviation)

| Organs | 5 min. | 30 min. | 60 min. | 180 min. |
|---|---|---|---|---|
| Heart | 0.132 ± 0.032 | 0.041 ± 0.006 | 0.017 ± 0.004 | 0.004 ± 0.002 |
|  | (0.229 ± 0.058) | (0.080 ± 0.019) | (0.031 ± 0.008) | (0.007 ± 0.002) |
| Lungs | 0.571 ± 0.230 | 0.373 ± 0.074 | 0.171 ± 0.040 | 0.069 ± 0.025 |
|  | (0.640 ± 0.236) | (0.390 ± 0.086) | (0.182 ± 0.035) | (0.075 ± 0.023) |
| Liver | 18.757 ± 3.225 | 13.932 ± 3.695 | 7.344 ± 0.694 | 1.219 ± 0.163 |
|  | (2.617 ± 0.132) | (1.922 ± 0.413) | (1.072 ± 0.231) | (0.200 ± 0.024) |
| Spleen | 0.175 ± 0.088 | 0.170 ± 0.055 | 0.081 ± 0.008 | 0.069 ± 0.031 |
|  | (0.362 ± 0.051) | (0.416 ± 0.168) | (0.176 ± 0.046) | (0.171 ± 0.53) |
| Kidneys | 4.564 ± 0.850 | 5.646 ± 0.919 | 5.439 ± 1.647 | 6.237 ± 1.026 |
|  | (3.131 ± 0.507) | (4.276 ± 0.533) | (4.262 ± 1.522) | (4.490 ± 0.638) |
| Stomach | 1.304 ± 1.206 | 0.209 ± 0.097 | 0.149 ± 0.024 | 0.090 ± 0.062 |
|  | (0.323 ± 0.206) | (0.057 ± 0.032) | (0.039 ± 0.011) | (0.035 ± 0.019) |
| Small intestine | 33.890 ± 4.651 | 41.709 ± 7.462 | 45.378 ± 2.739 | 30.633 ± 19.329 |
|  | (4.095 ± 0.762) | (5.413 ± 1.168) | (6.383 ± 0.486) | (4.459 ± 2.611) |
| Appendix | 0.294 ± 0.074 | 0.094 ± 0.023 | 0.078 ± 0.061 | 18.242 ± 20.821 |
|  | (0.060 ± 0.012) | (0.022 ± 0.002) | (0.016 ± 0.010) | (4.248 ± 4.880) |
| Colon | 0.181 ± 0.171 | 0.048 ± 0.015 | 0.019 ± 0.014 | 0.053 ± 0.066 |
|  | (0.289 ± 0.072) | (0.114 ± 0.047) | (0.046 ± 0.010) | (0.112 ± 0.135) |
| Rectum (inflammation) | 0.410 ± 0.157 | 0.410 ± 0.398 | 0.133 ± 0.092 | 0.032 ± 0.011 |
|  | (0.468 ± 0.127) | (0.216 ± 0.150) | (0.115 ± 0.076) | (0.028 ± 0.008) |
| Adrenal | 0.015 ± 0.005 | 0.005 ± 0.002 | 0.004 ± 0.000 | 0.001 ± 0.000 |
|  | (0.376 ± 0.119) | (0.129 ± 0.061) | (0.095 ± 0.008) | (0.023 ± 0.008) |
| Ovaries | 0.042 ± 0.012 | 0.025 ± 0.011 | 0.006 ± 0.002 | 0.002 ± 0.000 |
|  | (0.529 ± 0.150) | (0.309 ± 0.133) | (0.080 ± 0.020) | (0.022 ± 0.003) |
| Bones of lower limb | 0.377 ± 0.054 | 0.218 ± 0.052 | 0.121 ± 0.008 | 0.078 ± 0.023 |
|  | (0.289 ± 0.033) | (0.174 ± 0.053) | (0.097 ± 0.009) | (0.061 ± 0.017) |
| Skin | 0.773 ± 0.276 | 0.327 ± 0.233 | 0.112 ± 0.048 | 0.025 ± 0.011 |
|  | (0.268 ± 0.050) | (0.131 ± 0.047) | (0.044 ± 0.007) | (0.009 ± 0.002) |
| Muscle | 0.757 ± 0.118 | 0.310 ± 0.157 | 0.101 ± 0.012 | 0.022 ± 0.008 |
|  | (0.106 ± 0.014) | (0.047 ± 0.026) | (0.013 ± 0.001) | (0.03 ± 0.001) |
| Urine | 9.976 ± 3.195 | 23.885 ± 2.560 | 35.648 ± 1.482 | 41.509 ± 2.049 |
| Feces | 0.104 ± 0.139 | 0.032 ± 0.034 | 0.024 ± 0.023 | 0.215 ± 0.305 |
| Carcas | 22.375 ± 2.165 | 10.901 ± 4.459 | 4.354 ± 0.670 | 1.353 ± 0.323 |
|  | (0.192 ± 0.029) | (0.101 ± 0.058) | (0.037 ± 0.005) | (0.011 ± 0.002) |
| Rectum (inflammation)/ blood | 0.74 ± 0.10 | 0.95 ± 0.42 | 1.26 ± 0.82 | 1.51 ± 0.41 |
| Rectum (inflammation)/ muscle | 4.37 ± 0.68 | 4.46 ± 1.00 | 8.81 ± 6.35 | 9.29 ± 2.82 |

TABLE 12

Biodistribution of Tc-99m-peptide 6 in rat IBD model
Upper column: % ID/organ; Lower column: % ID/g
(n = 3, mean ± standard deviation)

| Organs | 5 min. | 30 min. | 60 min. | 180 min. |
|---|---|---|---|---|
| Blood | 5.232 ± 1.667 | 1.770 ± 0.092 | 0.818 ± 0.304 | 0.146 ± 0.029 |
|  | (0.625 ± 0.114) | (0.214 ± 0.057) | (0.092 ± 0.016) | (0.019 ± 0.002) |
| Heart | 0.132 ± 0.032 | 0.42 ± 0.006 | 0.017 ± 0.004 | 0.004 ± 0.002 |
|  | (0.229 ± 0.058) | (0.080 ± 0.020) | (0.031 ± 0.008) | (0.007 ± 0.002) |
| Lungs | 0.571 ± 0.230 | 0.374 ± 0.076 | 0.170 ± 0.040 | 0.069 ± 0.025 |
|  | (0.640 ± 0.236) | (0.391 ± 0.088) | (0.181 ± 0.035) | (0.075 ± 0.023) |
| Liver | 18.757 ± 3.225 | 13.991 ± 3.796 | 7.322 ± 0.720 | 1.219 ± 0.163 |
|  | (2.617 ± 0.132) | (1.930 ± 0.126) | (1.069 ± 0.235) | (0.200 ± 0.024) |
| Spleen | 0.175 ± 0.088 | 0.171 ± 0.055 | 0.081 ± 0.008 | 0.069 ± 0.031 |
|  | (0.362 ± 0.051) | (0.418 ± 0.170) | (0.176 ± 0.046) | (0.171 ± 0.053) |
| Kidneys | 4.564 ± 0.850 | 5.664 ± 0.917 | 5.427 ± 1.667 | 6.237 ± 1.026 |
|  | (3.131 ± 0.507) | (4.291 ± 0.548) | (4.254 ± 1.536) | (4.490 ± 0.638) |
| Stomach | 1.304 ± 1.206 | 0.210 ± 0.098 | 0.519 ± 0.649 | 0.090 ± 0.062 |
|  | (0.323 ± 0.206) | (0.057 ± 0.033) | (0.107 ± 0.109) | (0.035 ± 0.019) |
| Small intestine | 33.890 ± 4.651 | 41.389 ± 7.985 | 45.175 ± 2.447 | 30.633 ± 19.329 |
|  | (4.095 ± 0.762) | (5.371 ± 1.225) | (6.357 ± 0.498) | (4.459 ± 2.611) |
| Appendix | 0.294 ± 0.074 | 0.198 ± 0.166 | 0.078 ± 0.061 | 18.242 ± 20.821 |
|  | (0.060 ± 0.012) | (0.049 ± 0.044) | (0.016 ± 0.010) | (4.248 ± 4.880) |
| Colon | 0.181 ± 0.171 | 0.048 ± 0.014 | 0.019 ± 0.014 | 0.053 ± 0.066 |
|  | (0.289 ± 0.072) | (0.115 ± 0.048) | (0.046 ± 0.010) | (0.112 ± 0.135) |

TABLE 12-continued

Biodistribution of Tc-99m-peptide 6 in rat IBD model
Upper column: % ID/organ; Lower column: % ID/g
(n = 3, mean ± standard deviation)

| Organs | 5 min. | 30 min. | 60 min. | 180 min. |
|---|---|---|---|---|
| Rectum (inflammation) | 0.410 ± 0.157 (0.468 ± 0.127) | 0.413 ± 0.402 (0.217 ± 0.152) | 0.132 ± 0.091 (0.114 ± 0.075) | 0.032 ± 0.011 (0.028 ± 0.008) |
| Adrenal | 0.015 ± 0.005 (0.376 ± 0.119) | 0.005 ± 0.002 (0.130 ± 0.062) | 0.004 ± 0.000 (0.094 ± 0.008) | 0.001 ± 0.000 (0.023 ± 0.008) |
| Ovaries | 0.042 ± 0.012 (0.529 ± 0.150) | 0.025 ± 0.011 (0.311 ± 0.136) | 0.006 ± 0.002 (0.080 ± 0.021) | 0.002 ± 0.000 (0.022 ± 0.003) |
| Bones of lower limb | 0.377 ± 0.054 (0.289 ± 0.033) | 0.219 ± 0.054 (0.174 ± 0.054) | 0.120 ± 0.008 (0.097 ± 0.010) | 0.078 ± 0.023 (0.061 ± 0.017) |
| Skin | 0.773 ± 0.276 (0.268 ± 0.050) | 0.328 ± 0.237 (0.131 ± 0.048) | 0.112 ± 0.048 (0.044 ± 0.007) | 0.025 ± 0.011 (0.009 ± 0.002) |
| Muscle | 0.757 ± 0.118 (0.106 ± 0.014) | 0.311 ± 0.160 (0.047 ± 0.026) | 0.101 ± 0.012 (0.013 ± 0.001) | 0.022 ± 0.008 (0.03 ± 0.001) |
| Urine | 9.976 ± 3.195 | 23.955 ± 2.467 | 35.537 ± 1.650 | 41.509 ± 2.049 |
| Feces | 0.104 ± 0.139 | 0.032 ± 0.034 | 0.024 ± 0.023 | 0.215 ± 0.305 |
| Carcas | 22.375 ± 2.165 (0.192 ± 0.029) | 10.953 ± 4.550 (0.101 ± 0.058) | 4.338 ± 0.643 (0.037 ± 0.005) | 1.353 ± 0.323 (0.011 ± 0.002) |
| Rectum (inflammation)/ blood | 0.75 ± 0.13 | 1.27 ± 1.04 | 1.88 ± 1.44 | 2.74 ± 1.72 |
| Rectum (inflammation)/ muscle | 4.41 ± 0.97 | 5.54 ± 2.99 | 13.16 ± 11.07 | 16.50 ± 11.08 |

TABLE 13

Biodistribution of Tc-99m-peptide 12 in rat IBD model
Upper column: % ID/organ; Lower column: % ID/g (n = 3, mean ± standard deviation)

| Organs | 5 min. | 30 min. | 60 min. | 180 min. |
|---|---|---|---|---|
| Blood | 10.140 ± 9.197 (2.016 ± 0.074) | 1.122 ± 0.291 (0.179 ± 0.036) | 0.954 ± 0.447 (0.170 ± 0.068) | 0.308 ± 0.193 (0.069 ± 0.055) |
| Heart | 0.111 ± 0.045 (0.269 ± 0.082) | 0.027 ± 0.001 (0.061 ± 0.014) | 0.020 ± 0.011 (0.049 ± 0.026) | 0.007 ± 0.002 (0.018 ± 0.009) |
| Lungs | 0.280 ± 0.049 (0.382 ± 0.067) | 0.086 ± 0.017 (0.107 ± 0.032) | 0.071 ± 0.032 (0.096 ± 0.049) | 0.038 ± 0.029 (0.054 ± 0.050) |
| Liver | 21.311 ± 7.503 (3.326 ± 0.361) | 2.012 ± 0.397 (0.322 ± 0.075) | 0.972 ± 0.399 (0.162 ± 0.074) | 0.345 ± 0.235 (0.059 ± 0.042) |
| Spleen | 0.072 ± 0.020 (0.189 ± 0.029) | 0.024 ± 0.006 (0.064 ± 0.019) | 0.018 ± 0.006 (0.053 ± 0.018) | 0.009 ± 0.004 (0.031 ± 0.024) |
| Kidneys | 1.440 ± 0.326 (1.369 ± 0.302) | 1.077 ± 0.192 (0.977 ± 0.383) | 1.486 ± 1.002 (1.377 ± 0.996) | 0.598 ± 0.056 (0.506 ± 0.065) |
| Stomach | 2.461 ± 2.801 (0.631 ± 0.414) | 3.446 ± 4.540 (1.050 ± 1.309) | 1.990 ± 0.778 (0.659 ± 0.263) | 3.500 ± 4.830 (1.245 ± 1.129) |
| Small intestine | 43.689 ± 4.685 (6.289 ± 0.568) | 82.028 ± 4.176 (12.654 ± 1.252) | 80.691 ± 9.250 (13.503 ± 2.964) | 82.578 ± 1.469 (13.121 ± 2.433) |
| Appendix | 0.447 ± 0.366 (0.061 ± 0.008) | 0.116 ± 0.019 (0.030 ± 0.008) | 0.203 ± 0.070 (0.061 ± 0.025) | 2.703 ± 3.959 (0.783 ± 1.253) |
| Colon | 0.194 ± 0.152 (0.423 ± 0.333) | 0.021 ± 0.001 (0.061 ± 0.009) | 0.046 ± 0.032 (0.103 ± 0.077) | 0.026 ± 0.024 (0.057 ± 0.054) |
| Rectum (inflammation) | 1.149 ± 1.318 (0.486 ± 0.319) | 0.117 ± 0.060 (0.124 ± 0.044) | 0.637 ± 0.947 (0.398 ± 0.557) | 0.203 ± 0.328 (0.098 ± 0.142) |
| Adrenal | 0.018 ± 0.002 (0.441 ± 0.044) | 0.004 ± 0.002 (0.091 ± 0.047) | 0.017 ± 0.024 (0.420 ± 0.610) | 0.002 ± 0.003 (0.059 ± 0.072) |
| Ovaries | 0.052 ± 0.027 (0.646 ± 0.334) | 0.011 ± 0.000 (0.137 ± 0.004) | 0.015 ± 0.016 (0.182 ± 0.197) | 0.004 ± 0.004 (0.052 ± 0.050) |
| Bones of lower limb | 0.225 ± 0.047 (0.211 ± 0.047) | 0.066 ± 0.032 (0.078 ± 0.026) | 0.066 ± 0.032 (0.062 ± 0.027) | 0.28 ± 0.020 (0.028 ± 0.021) |
| Skin | 0.378 ± 0.114 (0.220 ± 0.017) | 0.191 ± 0.149 (0.096 ± 0.037) | 0.130 ± 0.048 (0.103 ± 0.076) | 0.052 ± 0.044 (0.030 ± 0.029) |
| Muscle | 0.537 ± 0.180 (0.104 ± 0.008) | 0.174 ± 0.073 (0.030 ± 0.011) | 0.120 ± 0.045 (0.026 ± 0.015) | 0.052 ± 0.044 (0.011 ± 0.010) |
| Urine | 0.681 ± 0.234 | 3.690 ± 0.886 | 6.171 ± 0.589 | 7.135 ± 2.769 |
| Feces | 0.656 ± 1.023 | 0.070 ± 0.023 | 0.356 ± 0.490 | 0.331 ± 0.325 |
| Carcas | 16.159 ± 2.511 (0.197 ± 0.056) | 5.702 ± 1.146 (0.062 ± 0.020) | 6.036 ± 4.684 (0.070 ± 0.056) | 2.081 ± 1.769 (0.027 ± 0.029) |
| Rectum (inflammation)/ blood | 0.43 ± 0.16 | 0.72 ± 0.33 | 1.89 ± 2.39 | 1.00 ± 0.89 |

TABLE 13-continued

Biodistribution of Tc-99m-peptide 12 in rat IBD model
Upper column: % ID/organ; Lower column: % ID/g (n = 3, mean ± standard deviation)

| Organs | 5 min. | 30 min. | 60 min. | 180 min. |
|---|---|---|---|---|
| Rectum (inflammation)/ muscle | 4.66 ± 3.13 | 4.21 ± 1.15 | 11.10 ± 12.33 | 6.22 ± 4.61 |

Example 7

Distribution of Tc-99m Labeled Peptide 3 and Peptide 6 in Human Blood (1) Method In order to confirm clinical effectiveness of the peptide of the present invention in human, binding affinities to leukocytes of two types of peptides of the present invention were examined by using human blood. The peptide 3 and the peptide 6 labeled with Tc-99m in Example 2 were separated into unlabeled peptides and labeled peptides, and purified by reversed phase HPLC under the same conditions as of HPLC in Example 2. A gradient elution was performed under the following conditions: 20%→80% (0.1% TFA acetonitrile/0.1% TFA water); 0→20 minutes (Radioactivity of the peptide 6 after purification was 111 MBq/ml).

The conventionally known peptides, Tc-99m-peptide 11 and Tc-99m-peptide 12, were prepared. Each of the peptide 11 and the peptide 12 was dissolved in dimethylformamide to prepare a solution having the concentration of 0.1 mg/500 µl. A solution of $SnCl_2$/10 mM hydrochloric acid (5 mg/10 ml) 50 µl was added to a tartaric acid/PBS solution (5 mg/200 µl), and the peptide solution was added thereto. Then $^{99m}TcO_4^-$ solution (2738 MBq/ml) 0.25 µl was infused immediately thereafter and shaken for several seconds to perform labeling reaction at 120° C. for 10 minutes. Final concentration was about 855.6 MBq/125 mg/ml. Purification and measurement of radiochemical purity were performed by using preparative HPLC. Analysis was performed under the same conditions as in Example 2, i.e. gradient: 20%→50% (0.1% TFA acetonitrile/0.1% TFA water); 0→20 minutes. Radioactivity concentration after the purification was 287–311 MBq/ml.

Subsequently, a Percoll density gradient solution was prepared based on the method described in Example 3.

Blood, 20–30 ml, was collected from adult volunteers, 40 years old or less. The Tc-99m labeled peptides, 30 µl (111 MBq/ml, $1.8 \times 10^{-11}$ mol/ml as Tc-peptide) each, were added thereto and incubated for 30 minutes. The blood sample 2–3 ml was layered over carefully to the prepared Percoll density gradient solution. After centrifugation at 2000 rpm (800×g) for 15 minutes, the tube was frozen and each fraction was cut off by using a cutter, then the radioactivity of each fraction was measured using Auto-Well Gamma Counter to determine the radioactivity distribution of Tc-99m-labeled peptides in the blood components.

(2) Results

Figure 18:
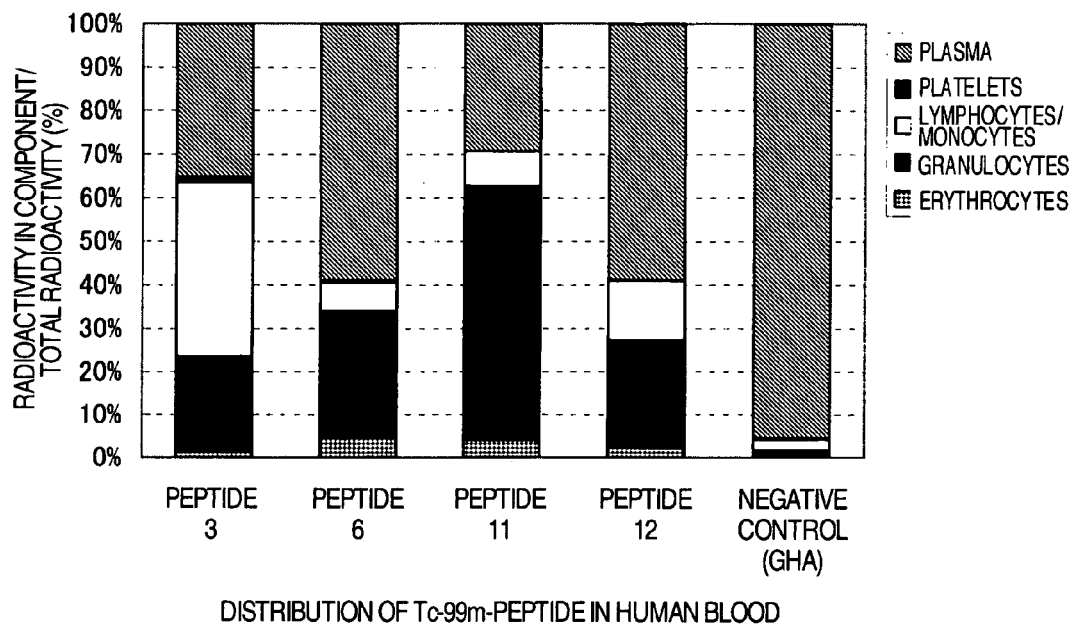
FIG. 18 shows a distribution of Tc-99m-peptide in the human blood.

According to the leukocyte counts of 4100–6100 cells/µl from the hematological parameter of human and the number of receptor FPR, 100,000–120,000/cell, found in the reference, estimated numbers of the receptor FPR in human blood were calculated as $0.68$–$1.2 \times 10^{-12}$ mol/ml, and a ratio of peptide/receptor in human blood was 0.03–0.01. Results showing distributions of 4 types of Tc-99m-peptides and the negative control (Tc-99m-glucoheptonic acid) in the human blood are shown in FIG. 18. Results showing percentages of a radioactivity of granulocyte fraction to the radioactivity in the total leukocytes, and a radioactivity of lymphocyte and monocyte fraction to the radioactivity in the total leukocytes are shown in Table 14. In Tc-99m-peptide 3, Tc-99m-peptide 11 and Tc-99m-peptide 12, n was 1, and in Tc-99m-peptide 6, n was 3.

A radioactivity distribution of Tc-99m-peptide 3 in the granulocyte fraction was 21.91% of the radioactivity in the whole blood and that of Tc-99m-peptide 3 in the lymphocyte and monocyte fraction was 39.98% of the radioactivity in the whole blood after the incubation for 30 minutes. The radioactivity of the granulocyte fraction was 35.41% for the radioactivity of the whole leukocyte, and the radioactivity of the lymphocyte and monocyte fraction was 64.59% for the radioactivity of the whole leukocyte. The results demonstrated that in the healthy human blood, Tc-99m-peptide 3 of the present invention was distributed in the lymphocyte and the monocyte much more than the conventionally known Tc-99m-peptide 11 and Tc-99m-peptide 12.

A radioactivity distribution of Tc-99m-peptide 6 in the granulocyte fraction was 29.45% of the radioactivity in the whole blood and that of Tc-99m-peptide 6 in the lymphocyte and monocyte fraction was 6.59% of the radioactivity in the whole blood after the incubation for 30 minutes. The radioactivity of the granulocyte fraction was 81.94±8.67% for the radioactivity of the whole leukocyte, and the radioactivity of the lymphocyte and monocyte fraction was 18.07±8.67% for the radioactivity of the whole leukocyte. The results demonstrated that in the healthy human blood, Tc-99m-peptide 6 of the present invention was distributed in the lymphocyte and the monocyte much more than the conventionally known Tc-99m-peptide 11.

A radioactivity distribution of the negative control Tc-99m-glucoheptonic acid in the granulocyte fraction was 1.11% of the radioactivity in the whole blood and that of Tc-99m-glucoheptonic acid in the lymphocyte and monocyte fraction was 2.52% of the radioactivity in the whole blood after the incubation for 30 minutes. In the plasma fraction, 95.39% thereof were distributed. Since it is the negative control which could not bind with leukocytes, a ratio of the radioactivity of the granulocyte fraction and a ratio of the radioactivity of the lymphocyte and monocyte fraction for the total leukocyte were not calculated.

In the human blood, a radioactivity distribution of Tc-99m-peptide 11 in the granulocyte fraction was 58.70% of the radioactivity in the whole blood and that of Tc-99m-peptide 11 in the lymphocyte and monocyte fraction was 8.02% of the radioactivity in the whole blood after the incubation for 30 minutes. The radioactivity of the granulocyte fraction was 87.98% for the radioactivity of the whole leukocyte, and the radioactivity of the lymphocyte and monocyte fraction was 12.03% for the radioactivity of the whole leukocyte.

In the human blood, a radioactivity distribution of Tc-99m-peptide 12 in the granulocyte fraction was 25.09% of the radioactivity in the whole blood and that of Tc-99m-peptide 12 in the lymphocyte and monocyte fraction was 13.77% of the radioactivity in the whole blood after the incubation for 30 minutes. The radioactivity of the granulocyte fraction was 64.57% for the radioactivity of the whole leukocyte, and the radioactivity of the lymphocyte and monocyte fraction was 35.43% for the radioactivity of the whole leukocyte.

Above results indicated that the peptide of the present invention was bound more strongly in the lymphocyte and the monocyte than in the granulocyte as compared with the negative control Tc-99m-glucoheptonic acid and the conventionally known Tc-99m-peptide 11 or Tc-99m-peptide 12. It was also proved that considering the results of Example 4 and Example 6, the peptides of the present invention were effective for chronic inflammation infiltrated with lymphocytes and monocytes.

TABLE 14

Binding ratio of Tc-99m labeled peptides to human leukocytes (n = 3, mean ± standard deviation)

| | Binding ratio to leukocytes (%) | |
|---|---|---|
| Labeled compound | Granulocytes | Lymphocytes and monocytes |
| Tc-99m-peptide 3 | 35.41 (n = 1) | 64.59 (n = 1) |
| Tc-99m-peptide 6 | 81.94 ± 8.67 | 18.07 ± 8.67 |
| Tc-99m-peptide 11 | 87.98 (n = 1) | 12.03 (n = 1) |
| Tc-99m-peptide 12 | 64.57 (n = 1) | 35.43 (n = 1) |

Example 8

Distribution of Tc-99m Labeled Peptide 3 and Peptide 6 in Rat Blood (1) Method

Preparation of Inflammatory Model:

A model rat of ulcerative colitis was prepared according to the method of Anthony et al. (Anthony et al. Int. J. Exp. Path., 76, 215–224, 1995). 2,4,6-Trinitrobenzene-sulfonic acid (TNBS) 360 mg was dissolved in ultra pure water 4 ml and ethanol 3.2 ml was added thereto to prepare 50.0 mg/ml 46% ethanol/physiological saline. A tube was inserted per anum in 7–8 cm depth into the intestine of etherized SD rat (Sprague Dawley strain rat, specific pathogen free), female, 7 weeks age, body weight 164–184 g, male, fasted before 24 hours, and air 0.1 ml was infused. A solution of TNBS/46% ethanol/physiological saline 0.2 ml was infused subsequently and massaged and tilted the posture for 2 minutes. These procedures were repeated for 3 days. After 4 days from the final administration, the rat was provided for the experiment, and the blood was collected. The collected blood of rat 2 ml was warmed at 37° C. for 5 minutes in a warm bath. Each sample 3 µl of Tc-99m-peptide 3 and Tc-99m-peptide 6 (111 MBq/ml, Tc-99m-peptide $1.8 \times 10^{-11}$ mol/ml) purified by HPLC was added thereto and incubated for 30 minutes. The blood sample was carefully layered over onto the previously prepared Percoll density gradient solution. The layered sample was centrifuged at 2000 rpm (800×g) for 15 minutes. After the centrifugation, the tube was frozen and each fraction was cut off by using a cutter, then the radioactivity of each fraction was measured using Auto-Well Gamma Counter to determine the radioactivity distributions of Tc-99m-peptide 3 and Tc-99m-peptide 6 in each component of the blood.

(2) Results

Figure 19:
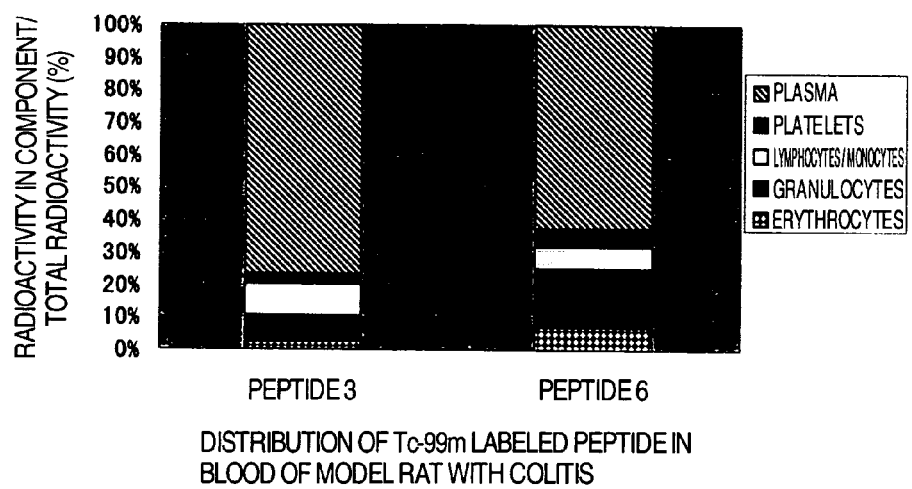
FIG. 19 shows a distribution of Tc-99m-labeled peptide in the blood of a model rat with colitis.

According to the leukocyte counts 6600–12600 cells/µl from the hematological parameter of female rat and the number of receptor FPR, 100,000–120,000/cell, found in the reference, estimated numbers of the receptor FPR in the blood of rats were calculated as $1.1–2.5 \times 10^{-12}$ mol/ml, and ratios of peptide/receptor in rats were 0.02–0.05. Results showing percentages of a radioactivity in each blood component to the radioactivity in the whole blood are shown in FIG. 19. Results showing percentages of a radioactivity of granulocyte fraction to the radioactivity in the total leukocytes, and a radioactivity of lymphocyte and monocyte fraction for the radioactivity in the total leukocytes are shown in Table 15.

In the blood of rat with ulcerative colitis caused by TNBS, a radioactivity distribution of Tc-99m-peptide 3 in the granulocyte fraction was 7.82% of the radioactivity in the whole blood and that of Tc-99m-peptide 3 in the lymphocyte and monocyte fraction was 10.00% of the radioactivity in the whole blood after the incubation for 30 minutes. The radioactivity of the granulocyte fraction was 43.69% for the radioactivity of the whole leukocyte, and the radioactivity of the lymphocyte and monocyte fraction was 56.31% for the radioactivity of the whole leukocyte. A radioactivity distribution of Tc-99m-peptide 6 in the granulocyte-fraction was 18.34% of the radioactivity in the whole blood and that of Tc-99m-peptide 6 in the lymphocyte and monocyte fraction was 6.57% of the radioactivity in the whole blood after the incubation for 30 minutes. The radioactivity of the granulocyte fraction was 74.08% for the radioactivity of the whole leukocyte, and the radioactivity of the lymphocyte and monocyte fraction was 25.92% for the radioactivity of the whole leukocyte.

From these results, it has become apparent that Tc-99m-peptide 3 and Tc-99m-peptide 6 as a part of the present invention were largely distributed in the lymphocyte and monocyte fraction in the blood of ulcerative colitis model rats.

From the above, it was proved that the peptide of the present invention was effective for diagnosis of chronic inflammation frequently infiltrated lymphocytes and monocytes.

TABLE 15

Binding ratio of Tc-99m labeled peptides to rat leukocytes
(Binding ratio to total leukocytes (%) n = 2, mean ± standard deviation)

| | Binding ratio to leukocytes (%) | |
|---|---|---|
| Labeled compound | Granulocytes | Lymphocytes and monocytes |
| Tc-99m-peptide 3 | 43.69 ± 2.74 | 56.31 ± 2.74 |
| Tc-99m-peptide 6 | 74.08 ± 8.37 | 25.92 ± 8.37 |

Example 9

Imaging of Tc-99m Labeled Compounds of Peptide 3 and Peptide 6 on Rat Ulcerative Colitis Model, and Effectiveness on Chronic Phase Inflammation (1) Method Preparation of Inflammatory Model:

A model rat of ulcerative colitis was prepared according to the method of Anthony et al. (Anthony et al. Int. J. Exp. Path., 76, 215–224, 1995). 2,4,6-Trinitrobenzene-sulfonic acid (TNBS) 360 mg was dissolved in ultra pure water 4 ml and ethanol 3.2 ml was added thereto to prepare 50.0 mg/ml 46% ethanol/physiological saline. A tube was inserted per anum in 7–8 cm depth into the intestine of etherized SD rat (Sprague Dawley strain rat, specific pathogen free), female, 7 weeks age, body weight 164–184 g, male, fasted before 24 hours, and air 0.1 ml was infused. A solution of TNBS/46% ethanol/physiological saline 0.2 ml was infused subsequently, and massaged and tilted the posture for 2 minutes. These procedures were repeated for 3 days. After 4 days from the final administration, the rat was provided for the experiment. Tc-99m-peptide 3 or Tc-99m-peptide 6 obtained in Example 2, each radioactivity of about 37 MBq/rat each, was administered to the tail vein. After 5 minutes, 30 minutes, 60 minutes and 120 minutes, the images were recorded by a gamma camera. As a control, Tc-99m labeled leukocytes, which was utilized for diagnosis of ulcerative colitis in human, was prepared according to the method of Roca et al. (M. Roca et al. Eur. J. Nucl. Med. 25, 797–799, 1998), and administered to the tail vein of the rat in a radioactivity of about 37 MBq/rat, and after 5 minutes, 30 minutes, 60 minutes and 120 minutes, the images were recorded by a gamma camera. Tc-99m labeled leukocyte was prepared containing all species of leukocytes such as granulocytes, lymphocytes and monocytes. After finishing the imaging, i.e. 130 minutes after the administration, the rat was exsanguinated from the abdominal aorta, and each organ was excised. Weights and radioactivities of the excised organs were measured to calculate the radioactivity per g tissue (% ID/g). Further, using the calculated numerical values, ratios of [inflammation]/[muscle] (ratios of [A]/[M]), ratios of [inflammation]/[blood] (ratios of [A]/[BL]), ratios of [inflammation]/[bone] (ratios of [A]/[BO]), ratios of [inflammation]/[appendix] (ratios of [A]/[AP]), ratios of [inflammation]/[colon] (ratios of [A]/[C]) and ratios of [inflammation]/[rectum] (ratios of [A]/[R]) were determined.

(2) Results

Figure 20:
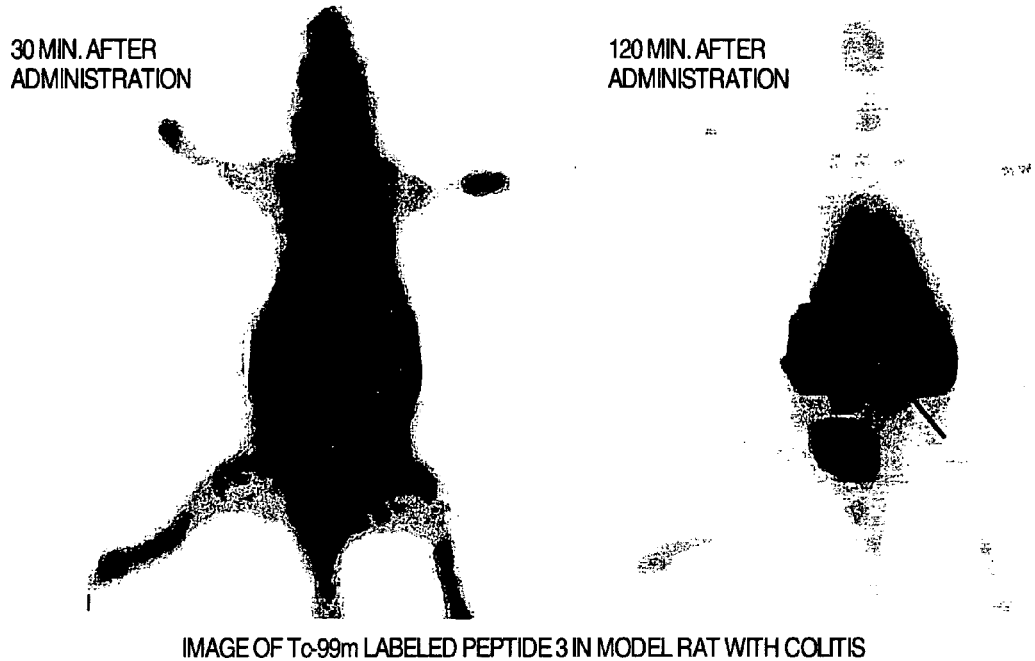
FIG. 20 shows an image of Tc-99m-labeled peptide 3 in a model rat with colitis. Left side is an image 30 minutes after the administration; right side is an image 120 minutes after the administration.
Figure 21:
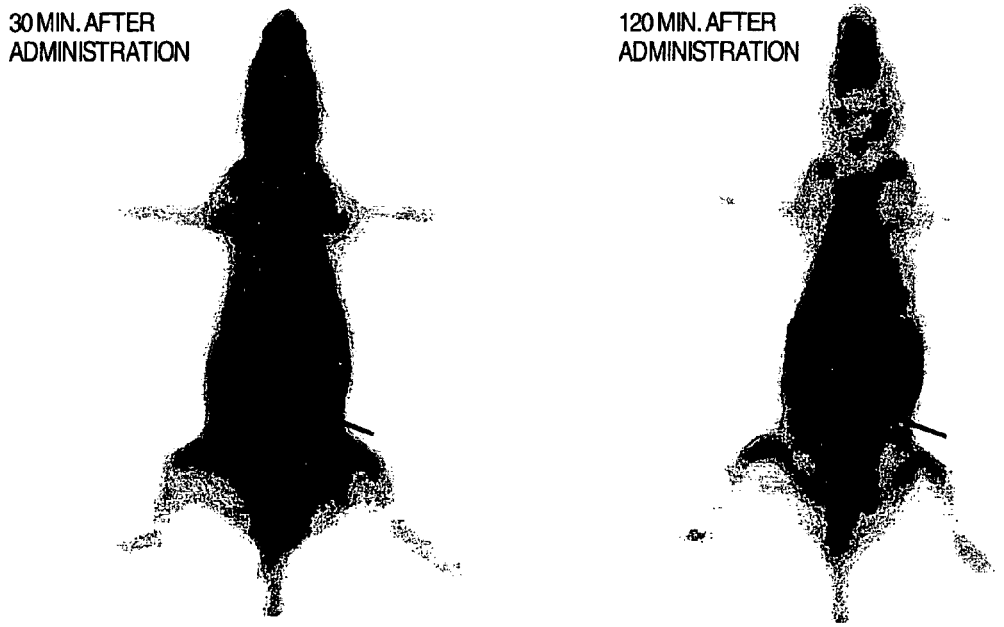
FIG. 21 shows an image of Tc-99m-labeled peptide 6 in a model rat with colitis. Left side is an image 30 minutes after the administration; right side is an image 120 minutes after the administration.
Figure 22:
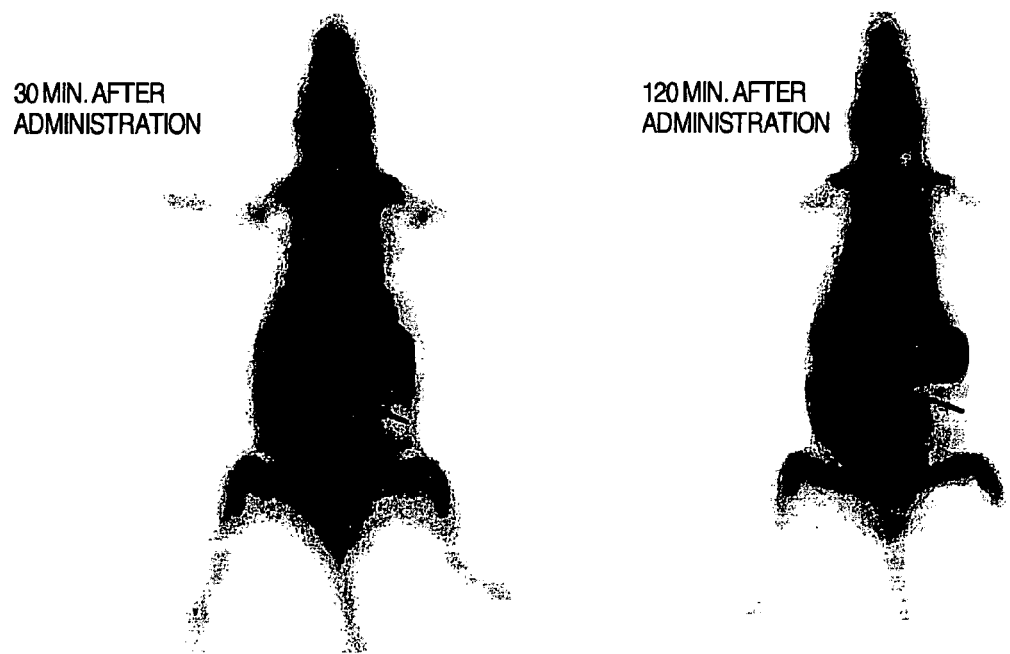
FIG. 22 shows an image of Tc-99m-labeled leukocytes in a model rat with colitis. Left side is an image 30 minutes after the administration; right side is an image 120 minutes after the administration.
Figure 23:
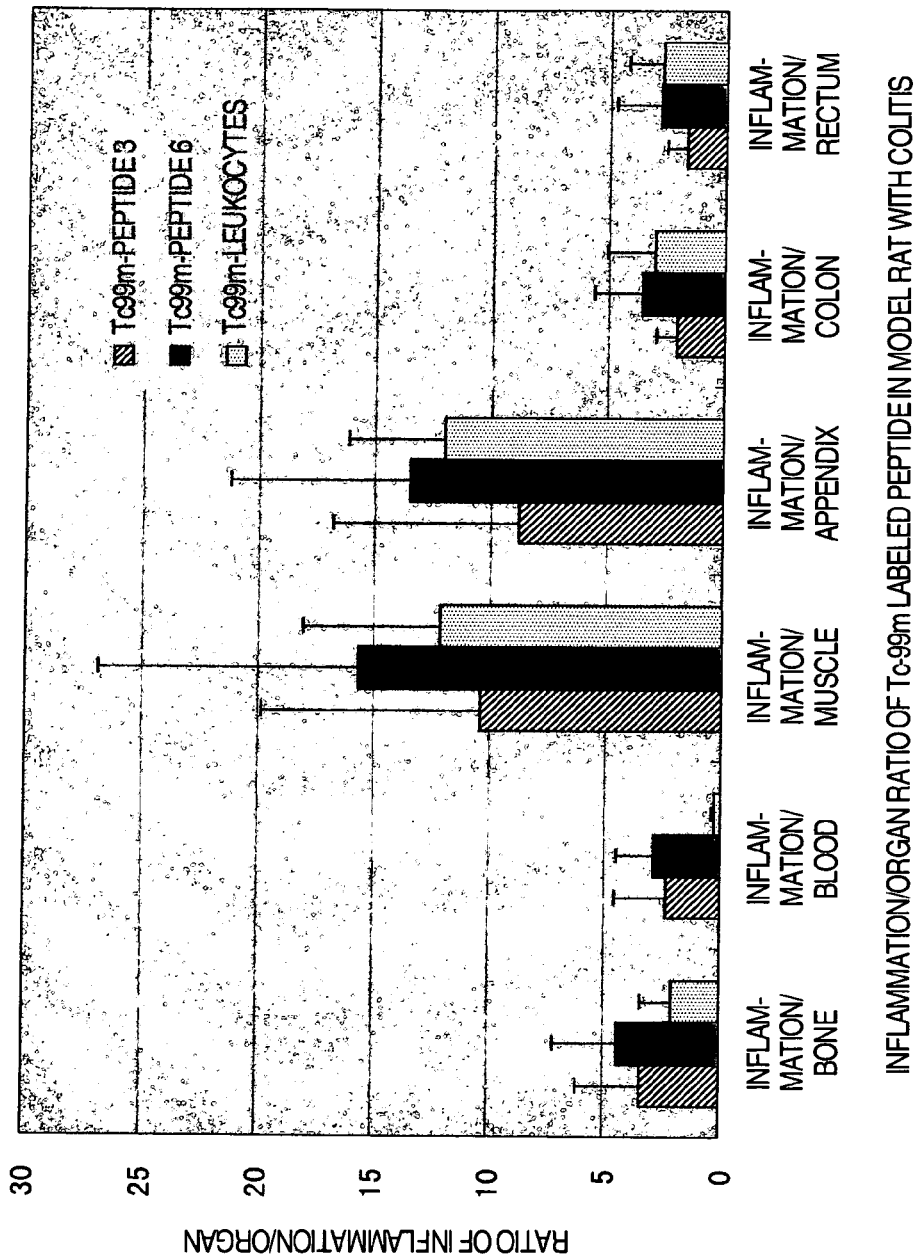
FIG. 23 shows inflammation/organ ratios of Tc-99m-labeled peptides in a model rat with colitis.

Representative drawings of the obtained results are shown in FIG. 20, FIG. 21 and FIG. 22. Regions of interest are set on the images, and ratios of counts in the region of interest of 1 pixel for whole body counts (% injection dose (ID)/pixel) are shown in Table 16. Results of the ratios indicating [inflammation]/[abdominal background] (ratios of [A]/[BG]) determined from the above ratios are shown in Table 17. Further, % ID/g of the inflammation, ratios of [A]/[M], ratios of [A]/[BL], ratios of [A]/[BO], ratios of [A]/[AP], ratios of [A]/[C] and ratios of [A]/[R] obtained from the results of excision are shown in Table 18 and FIG. 23. As a result, in the control Tc-99m labeled leukocytes, % ID/pixel after 30 minutes was 0.11±0.025 (mean±standard deviation) (n=5), a ratio of [A]/[BG] was 3.21±1.96 (n=5). Further, the radioactivity per g of tissue with inflammation (% ID/g) obtained from the exsanguination and the excision after 130 minutes from the administration was 0.71±0.33, and the ratio of [A]/[BO] was 2.08±1.37 and the ratio of [A]/[BL] was 0.25±0.17. The results indicated that the distribution was larger in the inflammation than in the blood.

Contrary to that, in Tc-99m-peptide 3 of the present invention, % administration/pixel after 30 minutes was 0.043±0.015 (n=5), a ratio of [A]/[BG] was 2.23±0.77 (n=5). Further, the radioactivity per g of tissue with inflammation (% ID/g) obtained from the exsanguination and the excision after 130 minutes from the administration was 0.13±0.12, and the ratio of [A]/[BO] was 3.40±2.78 and the ratio of [A]/[BL] was 2.33±2.22. These results indicated that the distribution of radioactivity was larger in the inflammation than in the blood. Further, in Tc-99m-peptide 6, % ID/pixel after 30 minutes was 0.093±0.048 (n=5), a ratio of [A]/[BG] was 2.15±0.53 (n=5). Further, the radioactivity per g of tissue with inflammation (% ID/g) obtained from the exsanguination and the excision after 130 minutes from the administration was 0.55±0.51, and the ratio of [A]/[BO] was 4.44±2.74 and the ratio of [A]/[BL] was 2.88±1.61. These results indicated that the distribution of radioactivity was larger in the inflammation than in the blood indicating the same as in the peptide 3. From the above results, it was demonstrated that the Tc-99m labeled peptides of the present invention was superior in the depiction of inflammation in organs with large bloodstream such as liver, spleen, heart, kidneys, brain and bone, which were easily affected by the blood. In particular, the peptide 6 showed superior numerical values in the ratio of [A]/[M], the ratio of [A]/[BL], the ratio of [A]/[BO], the ratio of [A]/[AP], the ratio of [A]/[C] and the ratio of [A]/[R] than the control Tc-99m labeled leukocytes. As a result, it was proved that the peptide of the present invention was excellent for depiction in the chronic inflammation, ulcerative colitis.

TABLE 16

Accumulation of Tc-99m labeled peptide in inflammation on rat colitis model (% ID/pixel) with or without FMLP inhibition (n = 5, mean ± standard deviation)

| | Elapse of time after administration | | | |
|---|---|---|---|---|
| | 5 min. | 30 min. | 1 hr | 2 hrs |
| Tc-99m-peptide 3 | 0.057 ± 0.011 | 0.043 ± 0.015 | 0.035 ± 0.014 | 0.031 ± 0.016 |
| Tc-99m-peptide 6 | 0.165 ± 0.066 | 0.093 ± 0.048 | 0.071 ± 0.050 | 0.069 ± 0.055 |
| Tc-99m-leukocytes | 0.120 ± 0.032 | 0.111 ± 0.025 | 0.102 ± 0.031 | 0.111 ± 0.043 |

TABLE 17

A ratio of inflammation/abdominal background of Tc-99m labeled peptides and Tc-99m-leukocytes in rat ulcerative colitis model with or without FMLP inhibition (n = 5, mean ± standard deviation)

| | Elapse of time after administration | | | |
|---|---|---|---|---|
| | 5 min. | 30 min. | 1 hr | 2 hrs |
| Tc-99m-peptide 3 | 1.84 ± 0.41 | 2.23 ± 0.77 | 3.67 ± 1.68 | 5.87 ± 3.20 |
| Tc-99m-peptide 6 | 2.64 ± 0.42 | 2.15 ± 0.53 | 1.90 ± 0.33 | 2.73 ± 0.52 |
| Tc-99m-leukocytes | 3.23 ± 1.50 | 3.21 ± 1.96 | 3.23 ± 1.73 | 3.71 ± 2.17 |

TABLE 18

Analytical results of Tc-99m labeled peptides and Tc-99m-leukocytes on rat ulcerative colitis model by excision (n = 5, mean ± standard deviation)

| Ratio of inflammation/organ | Tc-99m-peptide 3 | Tc-99m-peptide 6 | Tc-99m-leukocytes |
|---|---|---|---|
| Ratio of inflammation/muscle | 10.37 ± 9.54 | 15.66 ± 11.17 | 12.12 ± 5.97 |
| Ratio of inflammation/blood | 2.33 ± 2.22 | 2.88 ± 1.61 | 0.25 ± 0.17 |
| Ratio of inflammation/bone | 3.40 ± 2.78 | 4.44 ± 2.74 | 2.08 ± 1.37 |
| Ratio of inflammation/appendix | 8.75 ± 8.09 | 13.49 ± 7.75 | 11.99 ± 4.18 |
| Ratio of inflammation/colon | 2.10 ± 0.83 | 3.53 ± 2.06 | 3.03 ± 2.03 |

TABLE 18-continued

Analytical results of Tc-99m labeled peptides and Tc-99m-leukocytes on rat ulcerative colitis model by excision (n = 5, mean ± standard deviation)

| Ratio of inflammation/organ | Tc-99m-peptide 3 | Tc-99m-peptide 6 | Tc-99m-leukocytes |
|---|---|---|---|
| Ratio of inflammation/rectum | 1.68 ± 0.87 | 2.79 ± 1.99 | 2.73 ± 1.50 |
| Inflammation (% ID/g) | 0.13 ± 0.12 | 0.55 ± 0.51 | 0.71 ± 0.33 |

Example 10

Autoradiography of Tc-99m-Peptide 6 and Tc-99m-Peptide 14 in Rat Ulcerative Colitis Model and Usefulness Thereof for Chronic Inflammation (1) Method A model rat of ulcerative colitis was prepared according to the method of Anthony et al. (Anthony et al. Int. J. Exp. Path., 76, 215–224, 1995). 2,4,6-Trinitrobenzene-sulfonic acid (TNBS) 360 mg was dissolved in ultra pure water 4 ml and ethanol 3.2 ml was added thereto to prepare 50.0 mg/ml 46% ethanol/physiological saline. A tube was inserted per anum in 7–8 cm depth into the intestine of etherized SD rats (Sprague Dawley strain rat, specific pathogen free), female, 7 weeks age, body weight 164–184 g, male, fasted before 24 hours, and air 0.1 ml was infused. A solution of TNBS/46% ethanol/physiological saline 0.2 ml was infused subsequently, and massaged and tilted the posture for 2 minutes. These procedures were repeated for 3 days. After 4 days from the final administration, the rats were provided for the experiment. Tc-99m-peptide 6 or Tc-99m-peptide 14 obtained in Example 2, radioactivity of about 74 MBq/rat each, was administered to the tail vein, and after 120 minutes, rats were exsanguinated and killed. After immediate excision of the large intestine and removal of the intestinal content, areas judged to be inflammation region by macroscopic observation were embedded in the medium for preparation of frozen section. Immediately thereafter, the embedded samples together with vessels were immersed in the liquid nitrogen for several ten seconds to freeze the medium containing the excised region of the large intestine. After allowing to stand the sample in the freezer at −20° C. for several ten seconds, frozen sections were prepared by using a cryostat. After preparing sections, the sections were contacted to the imaging plate for autoradiography (Fuji Photo Film Co. Ltd.) for periods from 12 hours to 19 hours. Subsequently, the radioactivity distributions were imaged by using imaging analyzer BAS 2500 (Fuji Photo Film Co. Ltd.). Further, the frozen sections prepared by the same way were subjected to immunohistochemical staining for the anti-granulocyte antibody and the anti-monocyte antibody to confirm infiltration of the granulocyte and the monocyte into the tissue.

(2) Results

Figure 24:
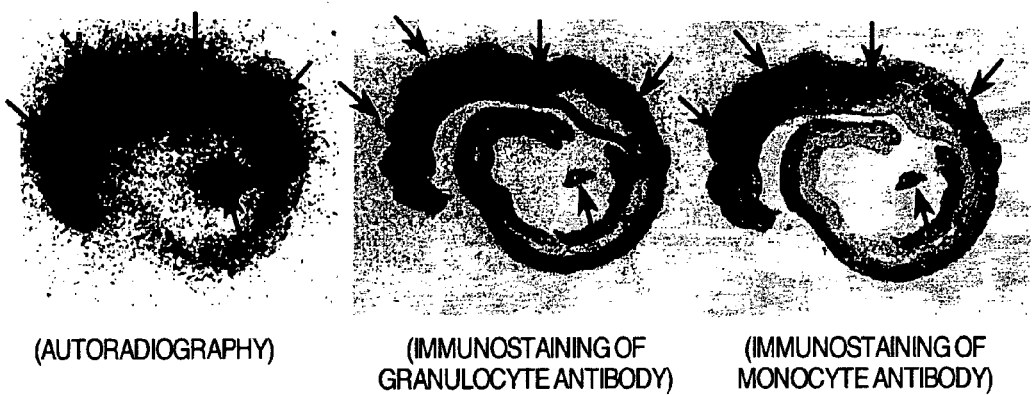
FIG. 24 shows images of peptide 6 on autoradiography and immuno-staining of a rat with colitis. Left side is autoradiograph; center is immuno-staining by anti-granulocytes antibody; right side is immuno-staining by anti-monocytes antibody.
Figure 25:
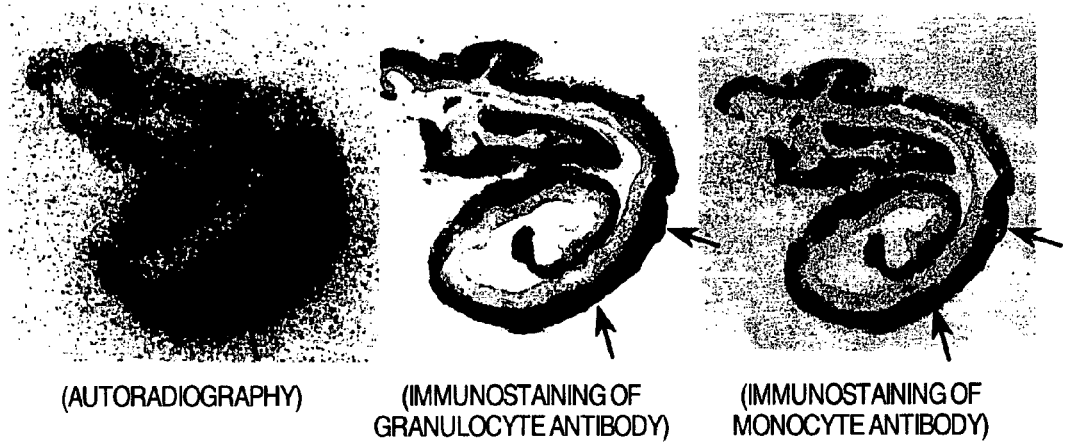
FIG. 25 shows images of peptide 14 on autoradiography and immuno-staining of a rat with colitis. Left side is autoradiograph; center is immuno-staining by anti-granulocytes antibody; right side is immuno-staining by anti-monocytes antibody.
Figure 26:
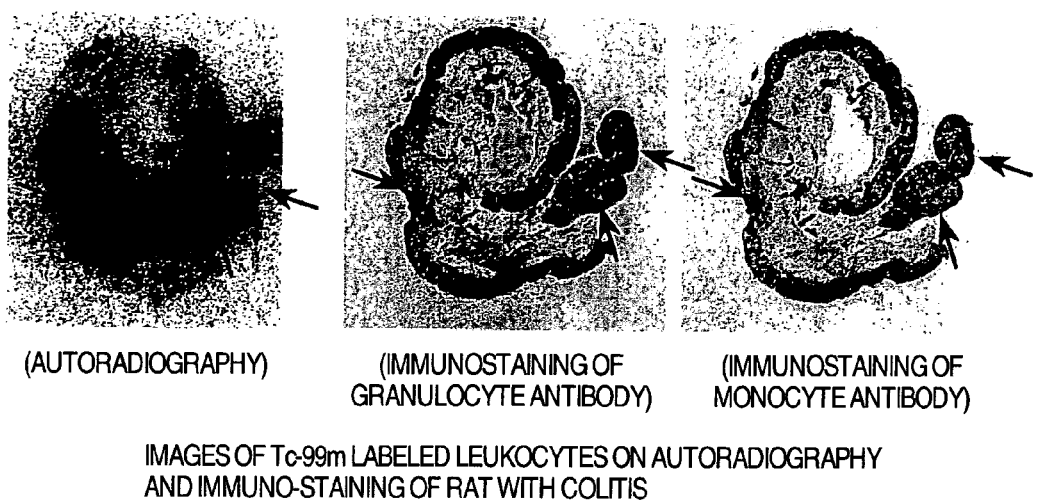
FIG. 26 shows images of Tc-99m-labeled leukocytes on autoradiography and immuno-staining of a rat with colitis. Left side is autoradiograph; center is immuno-staining by anti-granulocytes antibody; right side is immuno-staining by anti-monocytes antibody.
Figure 27:
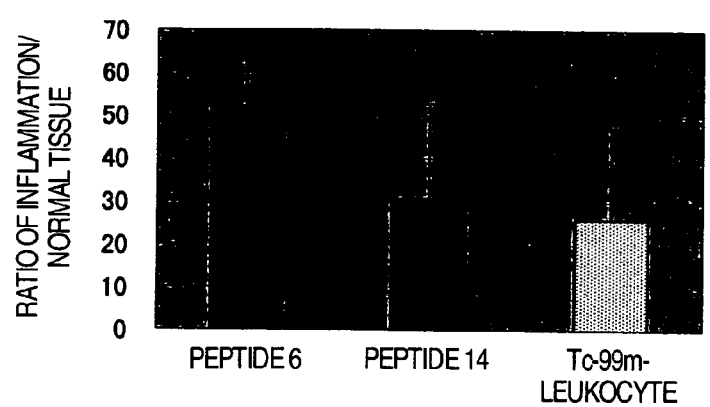
FIG. 27 shows inflammation/normal tissue ratios of autoradiography of a rat with colitis using Tc-99m-labeled peptide and Tc-99m-labeled leukocytes.

Representative drawings of the obtained results are shown in FIG. 24, FIG. 25 and FIG. 26. Regions of interest were set on the images obtained from the results of the autoradiography, and counts per pixel in the region of interest were calculated and ratios of [inflammation]/[normal tissue] (ratios of [A]/[N]) were determined. Results are shown in FIG. 27.

In the rectal region of rats with inflammation, inflammation ranging from 2 cm to 4 cm was formed in the whole circular area of the intestinal tract, and the inflammatory regions were observed in all rats. As a result of the immunohistochemical staining, significant infiltration of granulocytes and monocytes was observed in the inflammation region, and the granulocyte and the monocyte were observed to be distributed in the region corresponding to the inflammation.

Both of Tc-99m-peptide 6 and Tc-99m-peptide 14 showed radioactivity distributions corresponding to the distributions of the granulocyte and the monocyte exhibited by the immunostaining in a similar manner as Tc-99m-labeled leukocyte. In comparison of the ratios of [A]/[N] in the control Tc-99m-labeled leukocytes, Tc-99m-peptide 6 and Tc-99m-peptide 14 obtained from the same section, Tc-99m-peptide 6 and Tc-99m-peptide 14 showed higher ratios of [A]/[N] than Tc-99m-labeled leukocyte. As a result, it was also confirmed that the peptide of the present invention was superior in the chronic inflammation such as ulcerative colitis.

Example 11

Assay of Inhibitory Activity of Peptide 3, Peptide 4, Peptide 6, Peptide 8, Peptide 9, Peptide 16, Peptide 17 and Peptide 18 for Binding to Recombinant Human Receptor (1) Method The experiment was conducted using a recombinant receptor FPR derived from CHO cells (6.24 pmol/ml, 50 mM Tris-HCl, pH 7.4, 10% glycerol, 1% BSA, BioSignal Packard Inc., Amersham Biosciences) and [$^3$H]-FMLP (fMLF, 9.25 MBq/2.88–6.25 nmol, Daiichi Pure Chemicals Co. Ltd.). After adding each peptide to a certain amount of the receptor FPR (0.05 nM, 200 µl/well) in concentrations ranging from $10^{-4}$ M to $10^{-14}$ M, a certain amount of [$^3$H]-FMLP (0.3 nM, 25 µl/well) was added. After the reaction, an unbound [$^3$H]-FMLP with the receptor FPR and a bound [$^3$H]-FMLP with the receptor FPR were separated by using GF/C filter. Amount of the bound [$^3$H]-FMLP with the receptor FPR was determined by assaying the radioactivity of [$^3$H]-FMLP bound with the receptor FPR. A concentration of each peptide inhibiting 50% binding with [$^3$H]-FMLP (IC$_{50}$) was determined by using the analytical software "X1fit ver 3.0.3 (CTC Laboratory Systems K.K.)", further an inhibition constant (Ki) was determined from Kd value of [$^3$H]-FMLP. The tests were repeated three times and the assays were repeated three times in each test to determine a mean value.

(2) Results

Figure 28:
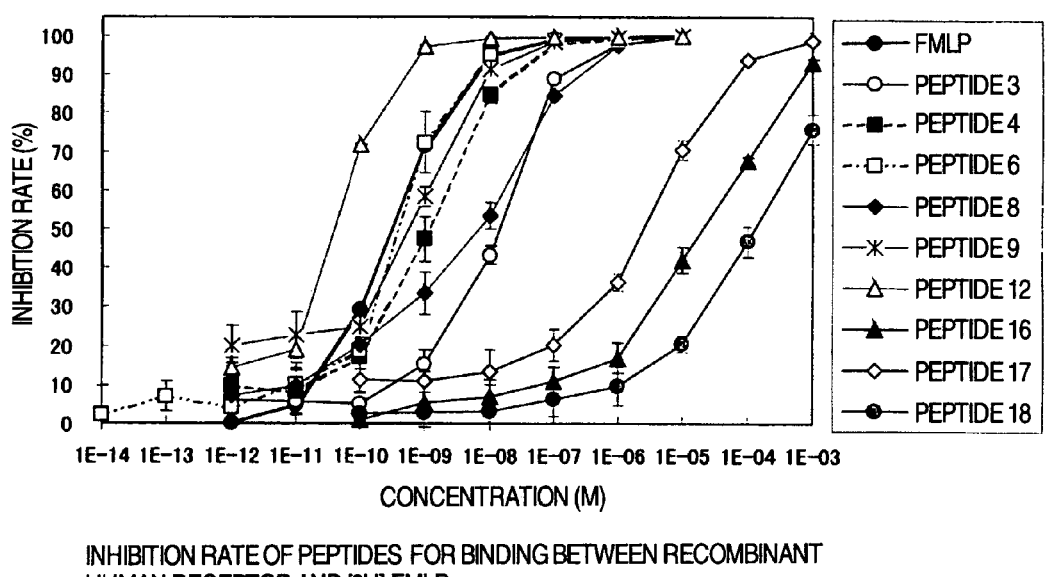
FIG. 28 shows inhibition rates of peptides for binding between recombinant human receptor and [$^3$H]-FMLP.

Results are shown in FIG. 28. Calculated IC$_{50}$ values and Ki values are shown in Table 19. The control FMLP was calculated to have a Ki value of $(2.33\pm0.45)\times10e^{-10}$ M. The Ki value of each peptide was calculated as follows: peptide 3: Ki=$(6.50\pm1.84)\times10e^{-9}$ M; peptide 4: Ki=$(8.36\pm3.74)\times10e^{-10}$ M; peptide 6: Ki=$(2.83\pm1.07)\times10e^{-10}$ M; peptide 8: Ki=$(2.33\pm0.91)\times10e^{-9}$ M; and peptide 9: Ki=$(1.28\pm0.69)\times10e^{-10}$ M. In the peptide 16, in which a formyl group was substituted by an acetyl group, the peptide 17, in which a formyl group was substituted by a carbamyl group, and the peptide 18, in which a formyl group was substituted by a methyl group, the Ki values were $(3.74\pm3.53)\times10e^{-6}$ M, $(4.24\pm3.60)\times10e^{-7}$ M and $(3.83\pm1.12)\times10e^{-5}$ M, respectively. As a result, the peptide of the present invention was proved to have affinity for the receptor FPR, and be useful for the diagnosis of inflammation mediated by the leukocyte which expresses the receptor FPR.

TABLE 19

Inhibitory concentration 50 ($IC_{50}$) and inhibition constant (Ki)
of each peptide (n = 9, mean ± standard deviation)

|  | $IC_{50}$(M) | Ki(M) |
|---|---|---|
| FMLP | (5.67 ± 1.10) × 10e−10 | (2.33 ± 0.45) × 10e−10 |
| Peptide 3 | (1.58 ± 0.45) × 10e−8 | (6.50 ± 1.84) × 10e−9 |
| Peptide 4 | (2.03 ± 0.91) × 10e−9 | (8.36 ± 3.74) × 10e−10 |
| Peptide 6 | (6.87 ± 2.59) × 10e−10 | (2.83 ± 1.07) × 10e−10 |
| Peptide 8 | (5.65 ± 2.21) × 10e−9 | (2.33 ± 0.91) × 10e−9 |
| Peptide 9 | (3.10 ± 1.69) × 10e−10 | (1.28 ± 0.69) × 10e−10 |
| Peptide 12 | (7.40 ± 5.03) × 10e−11 | (3.05 ± 2.07) × 10e−11 |
| Peptide 16 | (9.08 ± 8.58) × 10e−6 | (3.74 ± 3.53) × 10e−6 |
| Peptide 17 | (1.03 ± 0.88) × 10e−6 | (4.24 ± 3.60) × 10e−7 |
| Peptide 18 | (9.29 ± 2.71) × 10e−5 | (3.83 ± 1.12) × 10e−5 |

Example 12

Confirmation of Imaging for Inhibition of Tc-99m-Peptide 6 and Binding with Leukocyte In Vivo in Rabbit Infectious Disease Model (1) Method

*Staphylococcus aureus*, viable counts about $10^8$, was suspended in physiological saline 1 ml. The suspension 100 μl was injected intramuscularly into the right calf of New Zealand White (NZW) strain rabbits, body weight about 2 kg. After elapsing 24 hours, the model rabbits exhibiting apparent inflammation were anesthetized with pentobarbital. Tc-99m-peptide 6 obtained in Example 2, administration radioactivity of about 74 MBq, was administered to the auricular vein. After 5 minutes, 1 hour, 2 hours, 3 hours, 4 hours and 5 hours, images were recorded by using a gamma camera. A FMLP solution was prepared by dissolving FMLP 1 mg, which was corresponding to about 10,000 times of the estimated maximum quantity of the receptor 0.1 nmol/kg, in 5% DMSO/physiological saline. In the FMLP preadministration group, which was established for confirming inhibition by FMLP, the FMLP solution was administered to the auricular vein 5 minutes before the administration of Tc-99m-peptide 6. Similar to the group without administering FMLP, images were recorded by using a gamma camera after 5 minutes, 1 hour, 2 hours, 3 hours, 4 hours and 5 hours.

(2) Results

Figure 29:
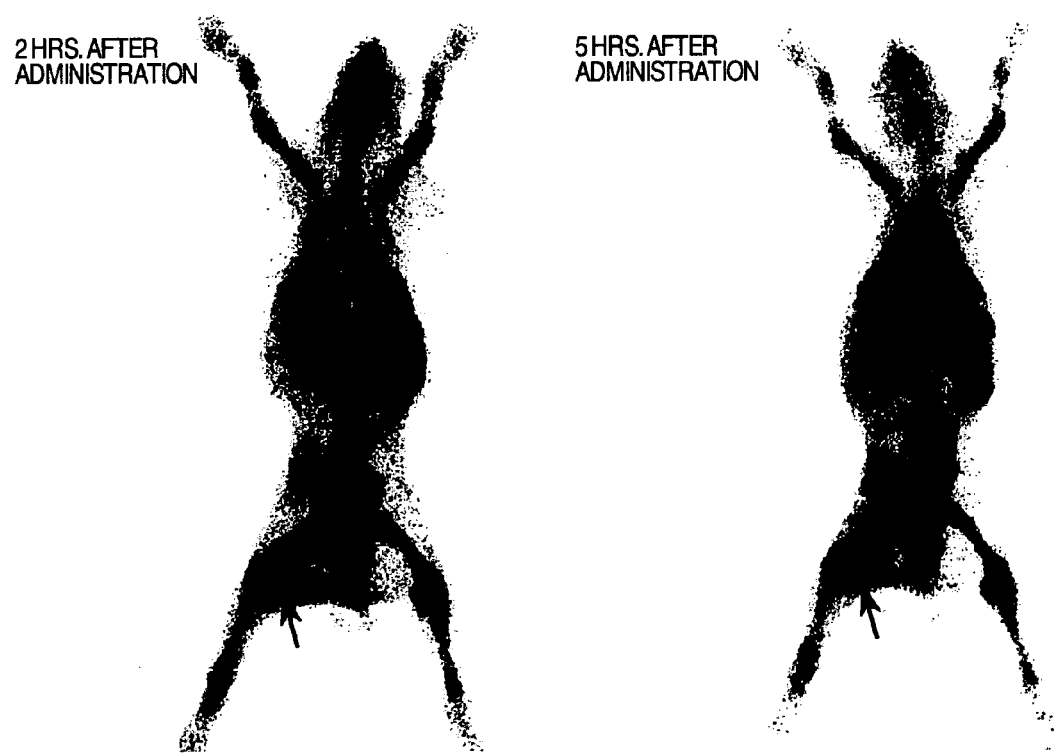
FIG. 29 shows an image of Tc-99m-labeled peptide 6 in a model rabbit with infectious disease without inhibition of FMLP. Left side is an image 2 hours after the administration; right-side is an image 5 hours after the administration.
Figure 30:
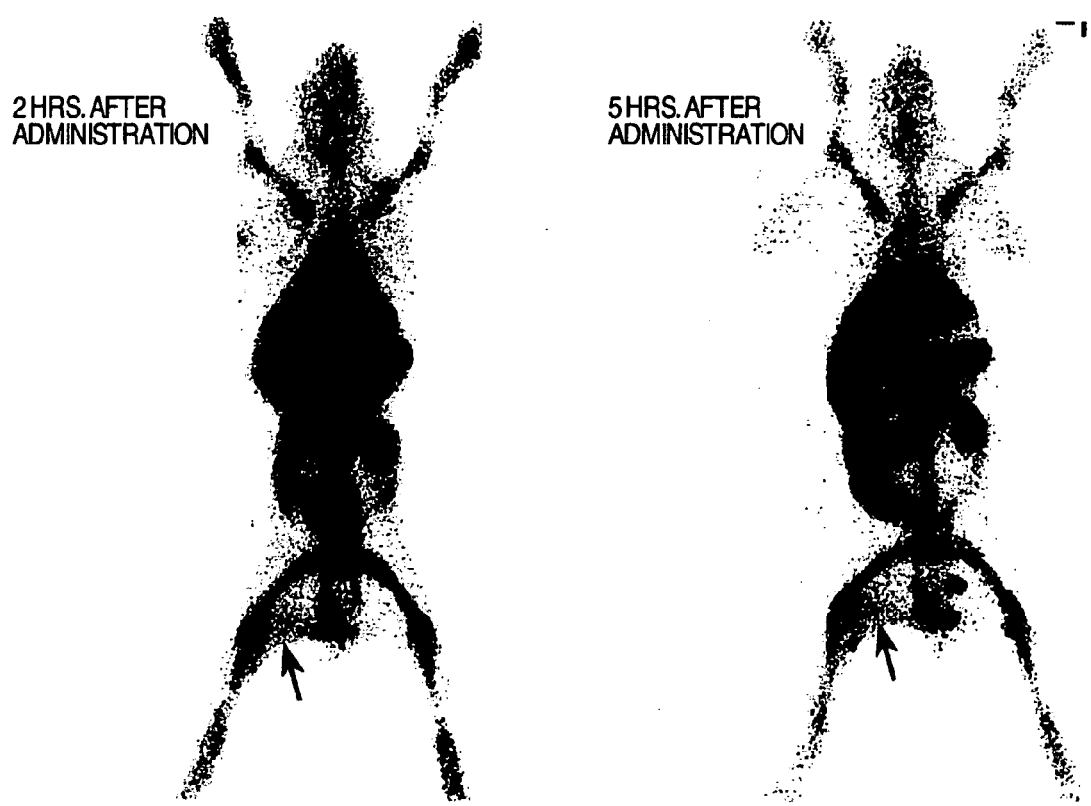
FIG. 30 shows an image of Tc-99m-labeled peptide 6 in a model rabbit with infectious disease with inhibition of FMLP.

Representative figures of the obtained results are shown in FIG. 29 and FIG. 30. Regions of interest are set on the images, and ratios of counts in the region of interest of 1000 pixel for whole body counts (% ID/K pixel) are shown in Table 20. Ratios indicating [inflammation]/[normal muscle] (ratios of [A]/[M]) determined from the above ratios are shown in Table 21. As a result, in Tc-99m-peptide 6 without inhibition of FMLP, accumulation to the inflammation region after 2 hours from the administration was 1.77±0.25% ID/Kpixel (mean±standard deviation) (n=3) and increased to 2.62±0.25% ID/Kpixel after 5 hours from the administration. The ratio of [A]/[M] also increased from 12.78±6.14 after 2 hours to 21.39±5.39 after 5 hours from the administration. Contrary to that, in Tc-99m-peptide 6 with inhibition of FMLP, the ratio of [A]/[M] after 2 hours from the administration was 3.93±0.60, which was lower as compared with the case without inhibition of FMLP, and the ratio of [A]/[M] after 5 hours from the administration increased to 9.05±3.10. However, accumulation to the inflammation region decreased from 0.41±0.10% ID/Kpixel after 2 hours from the administration to 0.30±0.04% ID/Kpixel after 5 hours from the administration.

These results indicated that the peptide 6 of the present invention was proved to depict the inflammation region by binding with the receptor FPR existing in the leukocyte. Accumulation of peptide of the present invention was thought to indicate onset of inflammation with leukocyte infiltration.

TABLE 20

Accumulation of Tc-99m-peptide 6 in inflammation (% ID/Kpixel) on rabbit infectious disease model with or without FMLP inhibition
(n = 3, mean ± standard deviation)

| | Elapse of time after administration | | | | | |
|---|---|---|---|---|---|---|
| | 5 min. | 1 hr | 2 hrs | 3 hrs | 4 hrs | 5 hrs |
| Without FMLP inhibition | 1.74 ± 0.22 | 1.59 ± 0.32 | 1.77 ± 0.25 | 2.01 ± 0.29 | 2.32 ± 0.56 | 2.62 ± 0.55 |
| With FMLP inhibition | 2.01 ± 0.43 | 0.75 ± 0.18 | 0.41 ± 0.10 | 0.31 ± 0.06 | 0.30 ± 0.03 | 0.30 ± 0.04 |

TABLE 21

Ratio of inflammation/muscle of Tc-99m-peptide 6 on rabbit infectious disease model with or without FMLP inhibition
(n = 3, mean ± standard deviation)

| | Elapse of time after administration | | | | | |
|---|---|---|---|---|---|---|
| | 5 min. | 1 hr | 2 hrs | 3 hrs | 4 hrs | 5 hrs |
| Without FMLP inhibition | 2.25 ± 0.46 | 6.18 ± 2.99 | 12.78 ± 6.14 | 14.53 ± 5.07 | 17.87 ± 5.46 | 21.39 ± 5.39 |
| With FMLP inhibition | 1.81 ± 0.19 | 2.62 ± 0.43 | 3.93 ± 0.60 | 6.42 ± 1.03 | 8.58 ± 2.60 | 9.05 ± 3.10 |

INDUSTRIAL APPLICABILITY

According to the present invention, compounds, which exhibit binding properties specific to all species of leukocytes, i.e. neutrophils, monocytes and lymphocytes both in vivo and in vitro and can be labeled with a radioactive metal or a paramagnetic metal, pharmaceutical composition containing the labeled compound as an active ingredient useful for SPECT image diagnosis, PET image diagnosis and MRI image diagnosis, can be provided, and the image diagnosis can be performed by imaging a site with vigorous leukocyte infiltration accompanied by an immune reaction in an individual.

The invention claimed is:

1. A compound that binds to leukocytes, wherein said compound is represented by the formula (1):

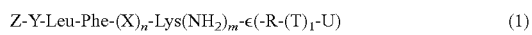    (1)

wherein, in the formula (1),

Z represents a protecting group for an amino group;

Y represents Met or Nle;

X represents a spacer consisting of one or more of amino acids and/or synthetic organic compounds;

n represents 1 or 0;

$NH_2$ represents an amide group as a protecting group for a carboxyl group in the α position of Lys;

m represents 1 or 0;

R represents Ser or Thr binding to an ε-amino group of Lys through an amide bond;

T represents a spacer consisting of one or more of amino acids and/or synthetic organic compounds;

l represents 1 or 0; and

U represents a group which can be labeled with a metal;

with the proviso that said X and T may be the same or different from each other.

2. The compound according to claim 1, wherein U in the formula (1) is a group consisting of a peptide represented by -Cys-A1-A2 (A1 and A2 are each an amino acid except for Cys and Pro), nitrogen-containing cyclic compounds with 8 to 20 carbon atoms, nitrogen-containing cyclic carboxylic acid compounds with 8 to 20 carbon atoms, derivatives of nitrogen-containing cyclic carboxylic acid compounds with 8 to 20 carbon atoms or alkylenamine carboxylic acids with 4 to 10 carbon atoms, which can be labeled with a metal.

3. The compound according to claim 1, wherein said compound represented by the formula (1) is one selected from the group consisting of:

formyl-Nle-Leu-Phe-Nle-Tyr-Lys($NH_2$)-ε-(-Ser-Cys-Gly-Asn);

formyl-Nle-Leu-Phe-Nle-Tyr-Lys($NH_2$)-ε-(-Ser-Cys-Gly-Asn);

formyl-Nle-Leu-Phe-Nle-Tyr-Lys($NH_2$)-ε-(-Ser-Cys-Gly-Asn);

formyl-Nle-Leu-Phe-Nle-Tyr-Lys($NH_2$)-ε-(-Ser-D-Arg-Asp-Cys-Asp-Asp);

formyl-Nle-Leu-Phe-Nle-Tyr-Lys($NH_2$)-ε-(-Ser-1,4,8,11-tetraazacyclotetradecane-1,4,8,11-tetraacetic acid);

formyl-Nle-Leu-Phe-Lys($NH_2$)-ε-(-Ser-D-Ser-Asn-D-Arg-Cys-Asp-Asp);

formyl-Nle-Leu-Phe-Nle-Tyr-Lys($NH_2$)-ε-(-Ser-D-Arg-diethylenetriamine pentaacetic acid);

formyl-Nle-Leu-Phe-Nle-Tyr-Lys($NH_2$)-ε-(-Ser-1,4,8,11-tetraazacyclotetradecane-butyric acid);

formyl-Nle-Leu-Phe-Nle-Tyr-Lys($NH_2$)-ε-(-Ser-D-Arg-Asp-1,4,8,11-tetraazacyclotetradecane-butyric acid);

formyl-Nle-Leu-Phe-Nle-Tyr-Lys($NH_2$)-ε-(-Ser-D-Arg-Asp-1,4,8,11-tetraazacyclotetradecane-butyric acid);

acetyl-Nle-Leu-Phe-Nle-Tyr-Lys($NH_2$)-ε-(-Ser-D-Arg-Asp-Cys-Asp-Asp);

carbamyl-Nle-Leu-Phe-Nle-Tyr-Lys($NH_2$)-ε-(-Ser-D-Arg-Asp-Cys-Asp-Asp); and methyl-Nle-Leu-Phe-Nle-Tyr-Lys($NH_2$)-ε-(-Ser-D-Arg-Asp-Cys-Asp-Asp).

4. A composition comprising a complex formed between a compound of formula (1) and a metal ion or a metal oxide of a radioactive metal or a paramagnetic metal, and a pharmaceutically acceptable carrier: wherein the compound is represented by the formula (1):

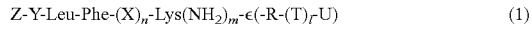    (1)

wherein, in the formula (1),

Z represents a protecting group for an amino group;

Y represents Met or Nle;

X represents a spacer consisting of one or more of amino acids and/or synthetic organic compounds;

n represents 1 or 0;

$NH_2$ represents an amide group as a protecting group for a carboxyl group in the α position of Lys;

m represents 1 or 0;

R represents Ser or Thr binding to an ε-amino group of Lys through an amide bond;

T represents a spacer consisting of one or more of amino acids and/or synthetic organic compounds;

l represents 1 or 0; and U represents a group which can be labeled with a metal;

with the proviso that said X and T may be the same or different from each other.

5. The composition according to claim 4, wherein said radioactive metal is Tc-99m, In-111, Ga-67, Cu-64 or Ga-68.

6. A method for imaging a site of vigorous leukocyte infiltration accompanied by immune reaction in an individual, said method comprising administering to an individual an effective amount of the composition according to claim 5 and conducting SPECT (single photon emission computed technology) or PET (positron emission tomography) imaging on the individual.

7. The composition according to claim 4, wherein said paramagnetic metal is Gd, Fe, Mn or Cu.

8. A method for imaging a site of vigorous leukocyte infiltration accompanied by immune reaction in an individual, said method comprising administering to said individual an effective amount of the composition according to claim 7 and conducting MRI (magnetic resonance imaging) on the individual.

9. The composition according to claim 4, wherein said radioactive metal is Y-90, Sn-117m, Sm-153, Re-186 or Re-188.

10. The compound according to claim 2, wherein said compound represented by the formula (1) is one selected from the group consisting of:

- formyl-Nle-Leu-Phe-Nle-Tyr-Lys(NH$_2$)-ϵ-(-Ser-Cys-Gly-Asn);
- formyl-Nle-Leu-Phe-Nle-Tyr-Lys(NH$_2$)-ϵ-(-Ser-Cys-Gly-Asn);
- formyl-Nle-Leu-Phe-Nle-Tyr-Lys(NH$_2$)-ϵ-(-Ser-Cys-Gly-Asn);
- formyl-Nle-Leu-Phe-Nle-Tyr-Lys(NH$_2$)-ϵ-(-Ser-D-Arg-Asp-Cys-Asp-Asp);
- formyl-Nle-Leu-Phe-Nle-Tyr-Lys(NH$_2$)-ϵ-(-Ser-1,4,8,11-tetraazacyclotetradecane-1,4,8,11-tetraacetic acid);
- formyl-Nle-Leu-Phe-Lys(NH$_2$)-ϵ-(-Ser-D-Ser-Asn-D-Arg-Cys-Asp-Asp);
- formyl-Nle-Leu-Phe-Nle-Tyr-Lys(NH$_2$)-ϵ-(-Ser-D-Arg-diethylenetriamine pentaacetic acid);
- formyl-Nle-Leu-Phe-Nle-Tyr-Lys(NH$_2$)-ϵ-(-Ser-1,4,8,11-tetraazacyclotetradecane-butyric acid);
- formyl-Nle-Leu-Phe-Nle-Tyr-Lys(NH$_2$)-ϵ-(-Ser-D-Arg-Asp-1,4,8,11-tetraazacyclotetradecane-butyric acid);
- formyl-Nle-Leu-Phe-Nle-Tyr-Lys(NH$_2$)-ϵ-(-Ser-D-Arg-Asp-1,4,8,11-tetraazacyclotetradecane-butyric acid);
- acetyl-Nle-Leu-Phe-Nle-Tyr-Lys(NH$_2$)-ϵ-(-Ser-D-Arg-Asp-Cys-Asp-Asp);
- carbamyl-Nle-Leu-Phe-Nle-Tyr-Lys(NH$_2$)-ϵ-(-Ser-D-Arg-Asp-Cys-Asp-Asp); and
- methyl-Nle-Leu-Phe-Nle-Tyr-Lys(NH$_2$)-ϵ-(-Ser-D-Arg-Asp-Cys-Asp-Asp).

11. A composition comprising the compound of any one of claims 1, 2, or 3, and a pharmaceutically acceptable carrier.

* * * * *